(12) United States Patent
Dollings et al.

(10) Patent No.: US 7,256,198 B2
(45) Date of Patent: Aug. 14, 2007

(54) PYRIMIDOINDOLONES AND METHODS FOR USING SAME

(75) Inventors: Paul Jeffrey Dollings, Newtown, PA (US); Arlene Joan Dietrich, Delran, NJ (US); Lisa Marie Havran, Florence, NJ (US); Chae-Koo Dan Chong, Plainsboro, NJ (US); Donna Mary Huryn, Allentown, NJ (US); Albert Jean Robichaud, Ringoes, NJ (US); Boyd Lynn Harrison, Princeton Junction, NJ (US); Wayne Everett Childers, New Hope, PA (US); Alexander A. Greenfield, West Windsor, NJ (US); James Jacob Bicksler, Titusville, NJ (US); Vasilios Marathias, Pennington, NJ (US)

(73) Assignee: Wyeth, Madison, NJ (US)

( * ) Notice: Subject to any disclaimer, the term of this patent is extended or adjusted under 35 U.S.C. 154(b) by 180 days.

(21) Appl. No.: 11/061,144

(22) Filed: Feb. 18, 2005

(65) Prior Publication Data

US 2005/0250798 A1 Nov. 10, 2005

Related U.S. Application Data

(60) Provisional application No. 60/546,084, filed on Feb. 18, 2004.

(51) Int. Cl.
*A01N 43/54* (2006.01)
*A61K 31/505* (2006.01)
*C07D 239/00* (2006.01)
*C07D 239/70* (2006.01)
*C07D 471/00* (2006.01)
*C07D 487/00* (2006.01)

(52) U.S. Cl. .................. 514/267; 544/252
(58) Field of Classification Search ......... 544/252; 514/267
See application file for complete search history.

(56) References Cited

U.S. PATENT DOCUMENTS 3,891,644 A * 6/1975 White .................... 544/252
4,784,996 A * 11/1988 White et al. ............. 514/267

FOREIGN PATENT DOCUMENTS

| EP | 0 987 027 A1 | 3/2000 |
|---|---|---|
| GB | 1 520 611 | 8/1978 |
| GB | 2 187 738 A | 9/1987 |
| GB | 2 187 739 A | 9/1987 |
| WO | 95/13807 A1 | 5/1995 |
| WO | 99/06042 A1 | 2/1999 |
| WO | 99/06367 A1 | 2/1999 |
| WO | 00/18769 A2 | 4/2000 |
| WO | 00/18769 A3 | 4/2000 |
| WO | 00/61159 A1 | 10/2000 |

OTHER PUBLICATIONS

Banker, Gilbert S. et al., Modem Pharmaceutics, Marcel Dekker, New York, 1996.*
Wolff, Manfred E., Burger's Medicinal Chemistry and Drug Discovery, Fifth Ed., vol. 1: Principles and Practice, John Wiley & Sons, 1995, 975.*
Gaur, Upasna, et al., Regulation of Proliferation, Survival and Apoptosis by Members fo the TNF Superfamily, Biochemical Pharmacology 66, 2003, 1403-1408.*
Supuran, Claudiu T. Supuran, Protease Inhibitors of the Sulfonamide Type: Anticancer, Antiinflammatory, and Antiviral Agents, Medicinal Research Reviews, vol. 23, No. 5, 535-558, 2003.*
Portnov, et al., Mosk. Gos. Univ. im. Lomonosova, Moscow, USSR Khimiya Geterotsiklicheskikh Soedinenii (1973), (5), 647-52.*
Chen, J. et al., "Induction of Caspase-3-Like Protease May Mediate Delayed Neuronal Death in the Hippocampus after Transient Cerebral Ischemia," *J. Neuroscience*, 18(13): 4914-4928 (1998).
Krupinski, J. et al., "Expression of Caspases and Their Substrates in the Rat Model of Focal Cerebral Ischemia," *Neurobiol. Dis.* 7: 332-342 (2000).
Benchoua, A et al., "Specific Caspase Pathways Are Activated in the Two Stages of Cerebral Infarction," *J. Neuroscience* 21(18): 7127-7134 (2001).
Namura, S. et al., "Activation and Cleavage of Caspase-3 in Apoptosis Induced by Experimental Cerebral Ischemia," *J. Neuroscience*. 18(10): 3659-3668 (1998).
Yaoita, H. et al., "Attenuation of Ischemia/Reperfusion Injury in Rats by a Caspase Inhibitor," *Circulation*, 97: 276-281 (1998).
Endres, M. et al., "Attenuation of Delayed Neuronal Death After Mild Focal Ischemia in Mice by Inhibition of the Caspase Family," *J. Cerebral Blood Flow and Metabolism*, 18: 238-247 (1998).
Cheng, Y. et al., "Caspase Inhibitor Affords Neuroprotection with Delayed Administration in a Rat Model of Neonatal Hypoxic-Ischemic Brain Injury," *J. Clin. Invest.*, 101(9):1992-1999 (May 1998).
Yakovlev, A. G. et al., Activation of CPP32-Like Caspases Contributes to Neuronal Apoptosis and Neurological Dysfunction after Traumatic Brain Injury, *J. Neuroscience*, 17(19): 7415-7424 (1997).
Rodriquez, I. et al., "Systemic Injection of a Tripeptide Inhibits the Intracellular Activation of CPP32-like Proteases in Vivo and Fully Protects Mice against Fas-mediated Fulminant Liver Destruction and Death," *J. Exp. Med.*, 184: 2067-2072 (1996).
Grobmyer, S. R. et al., "Peptidomimetic Fluoromethylketone Rescues Mice from Lethal Endotoxic Shock," *Mol. Med.*, 5: 585-594 (1999).
Pelletier, J-P. et al., "Selective Inhibition of Inducible Nitric Oxide Synthase Reduces Progression of Experimental Osteoarthritis in Vivo," *Arthritis & Rheumatism*, 43(6):1290-1299 (2000).

(Continued)

*Primary Examiner*—Zachary C. Tucker
*Assistant Examiner*—Erich A. Leeser
(74) *Attorney, Agent, or Firm*—Woodcock Washburn LLP

(57) ABSTRACT

Novel pyrimidoindolone compounds are disclosed. Methods of using the pyrimidoindolone compounds and compositions containing the compounds in the treatment and/or prevention of disease and other conditions related to inflammation, neurodegeneration, osteoarthritis and apoptosis are also disclosed.

29 Claims, No Drawings

OTHER PUBLICATIONS

Chan, H. K., "Application of polarography to the development of a stability-indicating assay method for a new indole derivative and its tablet formulations," *J. Pharmacy and Pharmacology* 1974, 26, Suppl:37P-40P.

Cliffe, I. A. et al., "Oral Hypoglycemic Agents. Pyrimido[1,2-a]indoles and Related Compounds," *J. Med Chem.*, Apr. 3, 1992, 35(7): 1169-1175.

Portnov, Y. N. et al., "Chemistry of Indole XXXVI. Rearrangement of 1-Phynyl-2-Acetylhydrazines and 1-Phenyl-2-Acetylpyrazolidines," *Chemistry of Heterocyclic Compounds*, 1973, 9:598-602.

Brown, D. G. et al., "Microwave-Assisted Synthesis of Heterocycles for Expedient Drug Discovery: Applications in Hit-to-Lead Discovery," Mid-Atlantic Symposium on Microwave Assisted Organic Synthesis, AstraZeneca Pharmaceuticals, 2003.

Lee, D. et al., "Potent and Selective Nonpeptide Inhibitors of Caspases 3 and 7," *J Med Chem*, 2001, 44:2015-2026.

Lee, D. et al., "Potent and Selective Nonpeptide Inhibitors of Caspases 3 and 7 Inhibit Apoptosis and Maintain Cell Functionality," *J Bio Chem*, 2000, 275(21): 16007-16014.

Popp, F. D., *Advances in Heterocyclic Chemistry*, 1975, 18: 1-58.

Sandmeyer, T., *Helvetica. Chim. Acta*, 1919, 2: 234-242.

T.W. Greene and P.G.M. Wuts, "Protective Groups in Organic Synthesis," 2$^{nd}$ ed. John Wiley and Sons, New York, NY, Chapter 4.

Cliffe, I. A., "Synthesis of 2,2-Dialkyl-3-Halopropanenitriles from 2,2-Dialkylethanenitriles and Dihalomethanes," *Syn Comm.*, 20(12) 1757-1767, 1990.

Mitsunobu, O., "The Use of Diethyl Azodicarboxylate and Triphenylphosphine in Synthesis and Transformation of Natural Products," *Synthesis*, 1981, 1-27.

Hewawasam, P. et al., "A General Method for the Synthesis of Isatins: Preparation of Regiospecifically Functionalized Isatins from Anilines," *Tetrahedron Letters*, 1994, 35(40): 7303-7306.

Thornbery, N.A., et al., "A Combinatorial Approach Defines Specificities of Members of the Caspase Family and Granzyme B," *J. Biol. Chem.* 1997 272(29) 17907-17911.

Stennicke, H. R. et al., "Biochemical Characteristics of Caspases-3, -6, and -8," *J. Biol. Chem.* 1997 272(41) 25719-25723.

Bundgaard, H. (ed.), *Design of Prodrugs*, Elsevier (1985), Ch. 1 (pp. 1-92), Ch. 4 (pp. 157-176), Ch. 5 (pp. 177-198), and Ch. 6 (pp. 199-241).

Widder, et al. (ed.), *Methods in Enzymology*, vol. 112, Academic Press (1985), pp. 309-396.

Krogsgaard-Larsen, et al. (ed.), "Design and Application of Prodrugs", Textbook of Drug Design and Development, Chapter 5, 113-191 (1991).

Bundgaard, H., "Means to enhance penetration; Prodrugs as a means to improve the delivery of peptide drugs," *Advanced Drug Deliver Reviews*, 1992, 8, 1-38.

Bundgaard, H. et al., "Glycolamide Esters as Biolabile Prodrugs of Carboxylic Acid Agents: Synthesis, Stability, Bioconversion, and Physicochemical Properties," *J. of Pharmaceutical Sciences*, Apr. 1988, 77(4):285-298.

Higuchi and Stella (eds.), *Prodrugs as Novel Drug Delivery Systems*, American Chemical Society (1975), pp. 1-115 and 196-223.

Fujita, S., "A Convenient Preparation of Arenesulfonyl Chlorides from the Sodium Sulfonates and Phosphoryl Chloride/Sulfolane," *Synthesis*, May 1982, pp. 423-424.

Kravchenko, D. V. et al., "Synthesis and Structure-Activity Relationship of 4-Substituted 2-(2-Acetyloxyethyl)-8 (morpholine-4-sulfonyl)pyrrolo[3,4-c]quinoline-1,3-diones as Potent Caspase-3 Inhibitors," *J Med Chem*, 2005, 48(11):3680-3683.

Kravchenko, D. V. et al., "1,3-Dioxo-4-methyl-2,3-dihydro-1 H-pyrrolo[3,4-c]quinolines as potent caspase-3 inhibitors," *Bioorganic & Medicinal Chemistry Letters*, 2005, 15(7):1841-1845.

* cited by examiner

PYRIMIDOINDOLONES AND METHODS FOR USING SAME

CROSS REFERENCE TO RELATED APPLICATIONS

The present application claims benefit of Provisional Application Ser. No. 60/546,084 filed Feb. 18, 2004, the complete disclosure of which is hereby incorporated by reference in its entirety.

FIELD OF THE INVENTION

The present invention relates to pyrimidoindolone compounds and, in certain embodiments, to their use as caspase inhibitors and for, inter alia, the treatment and/or prevention of disease and other conditions related to inflammation, neurodegeneration, osteoarthritis and apoptosis.

BACKGROUND OF THE INVENTION

Cell death is generally classified into one of two forms, necrosis or apoptosis. Necrosis typically occurs in response to severe physiological or environmental insult. Cells dying by necrosis show a distinct pattern of cellular breakdown, which eventually results in cell autolysis. The resulting release of cellular contents can cause inflammation in the surrounding tissues, furthering cell injury. Apoptosis on the other hand is a controlled or programmed series of cellular events ultimately leading to cell death. It is a mechanism for an organism to remove unwanted cells and is an important part of normal physiology. The two most often cited examples of apoptosis are in fetal development and in immune cell development. However, excessive or insufficient apoptosis can play a role in disease. Diseases in which there is an excessive accumulation of cells and insufficient apoptosis include cancer, inflammatory disorders and autoimmune diseases. Disorders in which excessive apoptotic cell death has been observed include neurodegenerative conditions such as Alzheimer's and Parkinson's diseases and ischemic stroke, brain or myocardial diseases. Tissue damage following stroke or myocardial infarction is largely apoptotic and there is growing evidence that the inhibition of apoptosis following ischemic injury can lessen the tissue damage.

One of the most specific molecular markers for apoptosis is the activation of the family of cysteine-dependent aspartate proteases, which are known as caspases. At least 11 human caspases have been characterized and these can be subdivided into three groups based on homology and substrate specificity. Group I caspases including 1, 4, 5, appear to be predominately involved in inflammation. Group II caspases including 6, 8, 9 and 10, are initiators of apoptotic signaling and further caspase activation. Group III caspases, including 3 and 7, are predominantly effector enzymes responsible for degrading cellular substrates in a highly specific manner. Although the precise repertoire of caspases involved in ischemic neuronal cell death have not been fully elucidated, histochemical and biochemical data combine to show the presence of activated caspases from each class in adult ischemic brain (Chen et al., *J. Neuroscience,* 18: 4914-4928 (1998), Krupinski et al., *Neurobiol. Dis.* 7: 332-342 (2000), Benchoua et al., *J. Neuroscience* 21: 7127-7134 (2001), Namura et al., *J. Neuroscience.* 18: 3659-3668 (1998)).

The utility of a caspase inhibitor for the treatment of a number of mammalian diseases associated with an increase in cellular apoptosis has been demonstrated using peptidic caspase inhibitors. For example, in rodent models caspase inhibitors have been shown to reduce infart size and inhibit cardiomyocyte apoptosis after myocardial infarction, to reduce brain lesion volume and neurological deficit resulting from stroke, to reduce post traumatic apoptosis and neurological deficit in traumatic brain injury, to be effective in treating fulminant liver destruction and to improve survival after endotoxic shock. (Yaoita, et al., *Circulation,* 97: 276 (1998), Endres et al., *J. Cerebral Blood Flow and Metabolism,* 18: 238 (1998), Cheng, et al., *J. Clin. Invest.,* 101: 1992 (1998); Yakovlev, et al., *J. Neuroscience,* 17: 7415 (1997), Rodriquez, et al., *J. Exp. Med.,* 184: 2067 (1996), Grobmyer, et al., *Mol. Med.,* 5: 585 (1999)).

A caspase inhibitor may provide utility for the treatment of osteoarthritis. A recent study demonstrated an increase in the level of the active form of caspase 3 in osteoarthritis chondrocytes. (Pelletier, et al., *Arthritis & Rheumatism,* 43 (6): 1290 (2000)). In osteoarthritis chondrocytes, the distribution of cells staining for caspase 3 was superimposable to that of cells undergoing apoptosis. The strong correlation between caspase 3 and apoptosis supports the notion that caspase 3 plays a role in chondrocyte apoptosis.

A chemical agent that can regulate the activity of the caspases in either a broad or a selective manner may be a useful therapeutic agent to treat diseases where an excessive or an insufficient level apoptosis is apparent. Of particular interest is treating ischemic diseases resulting in cerebral or myocardial injury such as stroke or as in the case of myocardial infarction. Since caspases are also implicated in the inflammatory process, a caspase modulator may be of therapeutic utility to treat inflammatory diseases, such as arthritis, cholangitis, colitis, encephalitis, endocerolitis, hepatitis and pancreatitis.

SUMMARY OF THE INVENTION

In one embodiment, the present invention relates to novel pyrimidoindolone compounds. It has been found in accordance with the present invention that pyrimidoindolones can be used as caspase inhibitors in, for example, the treatment and/or prevention of disease and other conditions related to inflammation, neurodegeneration, osteoarthritis and apoptosis. The compounds of this invention preferably are used for the treatment of ischemic injury associated with stroke or myocardial infarction.

In one aspect, compounds according to the present invention are those of Formula I:

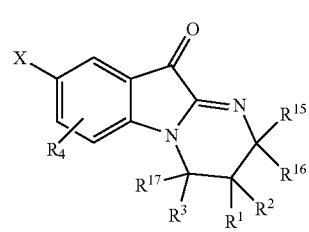

or a prodrug, stereoisomer, or pharmaceutically-acceptable salt thereof;

wherein:

$R^1$ and $R^2$ are independently hydrogen, halogen, alkyl, aryl, heteroaryl, or $R^1$ and $R^2$ together with the carbon atom to which they are attached, form a $C_3$-$C_7$ carbocyclyl or a $C_3$-$C_7$ heterocycle;

$R^3$ and $R^{17}$ are independently, hydrogen and alkyl;

$R^{15}$, $R^{16}$ are independently hydrogen, alkyl, or aryl, provided that $R^{15}$ and $R^{16}$ are not both aryl;

$R^4$ is hydrogen, halogen, alkyl, nitro, nitrile, carboxyl, hydroxy, amino, $R^7R^8N$—, alkoxy, or perfluoroalkoxy;

X is nitro, cyano, alkyl, perfluoroalkoxy, halogen,

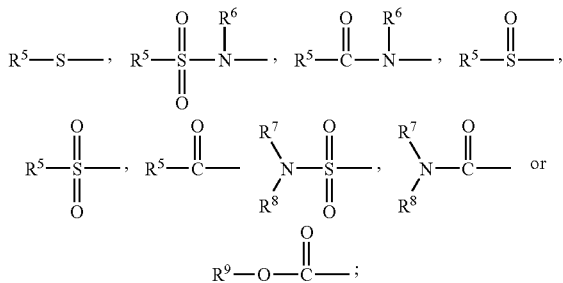

$R^5$ is alkyl, aryl, heteroaryl, heterocycle, or carbocyclyl;

$R^6$ is hydrogen or $C_1$-$C_3$ alkyl;

$R^7$ and $R^8$ are independently hydrogen, alkyl, aryl, heteroaryl, aralkyl, heteroaralkyl, alkanoyl, perfluoroalkanoyl, aroyl, heteroaroyl, aralkanoyl, heteroaralkanoyl, or $R^7$ and $R^8$ together with the nitrogen to which they are attached form a 5 to 10 member optionally substituted monocyclic or bicyclic ring system, which may further contain heteroatoms selected from oxygen, nitrogen or sulfur, provided that no ring may contain more than 3 heteroatoms; and $R^9$ is hydrogen, alkyl, aryl, heteroaryl, aralkyl, $C_4$-$C_{12}$ heteroaralkyl, or $C_3$-$C_{12}$ carbocyclyl.

In another aspect, the present invention is directed to compositions comprising one or more a compounds of formula I and one or more pharmaceutically acceptable carriers.

The present invention also provides in vitro and in vivo methods in which one or more compounds of formula I are contacted with at least one caspase. Preferred methods of this type are ones in which the activity of the caspase is determined before or after such contacting and, optionally, the determination is used to assess the extent to which the compound modulates the activity of the enzyme.

This invention also provides methods for treating and/or preventing disease or injury. In preferred embodiments, the methods of the invention are directed to inflammatory diseases (including, but not limited to arthritis, colitis, encephalitis, hepatitis, and pancreatitis), neurodegenerative disease (including, but not limited to Alzheimer's disease, Parkinson's disease traumatic brain injury, spinal cord injury, multiple sclerosis, and amyotrophic lateral sclerosis), ischemic injuries, including myocardial infarction and stroke, osteoarthritis-related diseases characterized by erosion of articular cartilage, and other related illnesses. Such methods generally involve administering to a patient suspected of suffering from or being susceptible to the disease or injury an effective amount of a compound of formula I.

The present invention further embodies administering to a patient a compound of formula I. Additionally, one skilled in the art will appreciate that the present invention also includes the treatment and/or prevention of apoptosis in patients suspected of suffering from apoptosis, in addition to the treatment and/or prevention inflammatory diseases (including, but not limited to arthritis, colitis, encephalitis, hepatitis, and pancreatitis), neurodegenerative disease (including, but not limited to Alzheimer's disease, Parkinson's disease traumatic brain injury, spinal cord injury, multiple sclerosis, and amyotrophic lateral sclerosis), ischemic injuries, including myocardial infarction and stroke, osteoarthritis-related diseases characterized by erosion of articular cartilage, and other related illnesses.

DETAILED DESCRIPTION OF ILLUSTRATIVE EMBODIMENTS

The term "alkyl", as used herein, whether used alone or as part of another group, refers to an aliphatic hydrocarbon chain and includes, but is not limited to, straight and branched chains having 1 to 6 carbon atoms unless otherwise specified. Specifically included within the definition of "alkyl" are those alkyl moieties that are optionally substituted with fluorine, such as perfluoroalkyl.

The carbon number, as used in the definitions herein, refers to carbon backbone and carbon branching, but does not include carbon atoms of substituents, such as alkoxy substitutions and the like.

The term "alkoxy", as used herein, whether used alone or as part of another group, refers the group R—O—, where R is an alkyl group having 1 to 3 carbon atoms as defined above.

The term "alkanoyl", as used herein, whether used alone or as part of another group, refers to a substituted or unsubstituted R—C(=O)— group having 2 to 7 carbon atoms, where R is an alkyl group as defined above.

The terms "halogen" or "halo", as used herein, refers to bromine, chlorine, fluorine, and iodine.

The term "carbocyclyl", as used herein, whether used alone or as part of another group, refers to a substituted or unsubstituted, saturated or unsaturated aliphatic ring system containing 3 to 14 carbon atoms, unless otherwise specified. Specifically included within the definition of "carbocyclyl" are those carbocyclyl moieties that are optionally substituted. Suitable substituents on the unsaturated carbon atom of a carbocyclyl include a halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), -nitro, —CN, —N(R°)$_2$, —NR°C(O)R°, —NR°C(O)N(R°)$_2$, —NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)N(R°)$_2$, —(CH$_2$)$_m$NHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph), and m is 0-3.

The term "heterocycle", as used herein, whether used alone or as part of another group, refers to a substituted or unsubstituted, saturated or unsaturated aliphatic ring system containing 3 to 12 carbon atoms, and 1 to 3 heteroatoms. Specifically included within the definition of "heterocycle" are those heterocycle moieties that are optionally substituted. Suitable substituents on the unsaturated carbon atom of a heterocycle include a halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), -nitro, —CN, —N(R°)₂, —NR°C(O)R°, —NR°C(O)N(R°)₂, —NR°CO₂R°, —C(O)C(O)R°, —C(O)CH₂C(O)R°, —CO₂R°, —C(O)R°, —C(O)N(R°)₂, —OC(O)N(R°)₂, —S(O)₂R°, —SO₂N(R°)₂, —S(O)R°, —NR°SO₂N(R°)₂, —NR°SO₂R°, —C(=S)N(R°)₂, —C(=NH)N(R°)₂, —(CH₂)ₘNHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH₂(Ph), or substituted —CH₂(Ph), and m is 0-3.

The term "aryl", as used herein, whether used alone or as part of another group, refers to a substituted or unsubstituted aromatic hydrocarbon ring group containing 6 to 12 carbon atoms, and includes, but is not limited to phenyl, naphthyl and anthracyl. Also included within the scope of the term "aryl", as used herein, is a group in which an aromatic ring is fused to one or more non-aromatic rings, such as in an indanyl, phenanthridinyl or tetrahydronaphthyl, where the radical or point of attachment is on the aromatic ring. Specifically included within the definition of "aryl" are those aromatic ring hydrocarbon chains that are optionally substituted. Suitable substitutions on the unsaturated carbon atom of an aryl include, but are not limited to, halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH₂(Ph), substituted —CH₂(Ph), —CH₂CH₂(Ph), substituted —CH₂CH₂(Ph), -nitro, —CN, —N(R°)₂, —NR°C(O)R°, —NR°C(O)N(R°)₂, —NR°CO₂R°, —C(O)C(O)R°, —C(O)CH₂C(O)R°, —CO₂R°, —C(O)R°, —C(O)N(R°)₂, —OC(O)N(R°)₂, —S(O)₂R°, —SO₂N(R°)₂, —S(O)R°, —NR°SO₂N(R°)₂, —NR°SO₂R°, —C(=S)N(R°)₂, —C(=NH)N(R°)₂, —(CH₂)ₘNHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH₂(Ph), or substituted —CH₂(Ph), and m is 0-3.

The term "aralkyl", as used herein, whether used alone or as part of another group, refers to a substituted or unsubstituted R'—R— group containing 7 to 13 carbon atoms, where R' is an aryl group as defined above, and R is an alkyl group as defined above. Specifically included within the definition of "aralkyl" are those aromatic ring hydrocarbon chains that are optionally substituted. Preferably, the aromatic ring of an aralkyl moiety includes, but is not limited to, phenyl, naphthyl or anthracyl. Suitable substitutions on the unsaturated carbon atom of an aralkyl include, but are not limited to, halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH₂(Ph), substituted —CH₂(Ph), —CH₂CH₂(Ph), substituted —CH₂CH₂(Ph), -nitro, —CN, —N(R°)₂, —NR°C(O)R°, —NR°C(O)N(R°)₂, —NR°CO₂R°, —C(O)C(O)R°, —C(O)CH₂C(O)R°, —CO₂R°, —C(O)R°, —C(O)N(R°)₂, —OC(O)N(R°)₂, —S(O)₂R°, —SO₂N(R°)₂, —S(O)R°, —NR°SO₂N(R°)₂, —NR°SO₂R°, —C(=S)N(R°)₂, —C(=NH)N(R°)₂, —(CH₂)ₘNHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH₂(Ph), or substituted —CH₂(Ph), and m is 0-3.

The term "aralkoxy", as used herein, whether used alone or as part of another group, refers to a substituted or unsubstituted R'—R—O— group, where R' is an aryl group and R is an alkyl group, as defined above. Specifically included within the definition of "aralkoxy" are those aromatic ring hydrocarbon chains that are optionally substituted. Preferably, the aromatic ring of an aralkoxy moiety includes, but is not limited to, phenyl, naphthyl or anthracyl. Suitable substitutions on the unsaturated carbon atom of an aralkoxy include, but are not limited to, halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH₂(Ph), substituted —CH₂(Ph), —CH₂CH₂(Ph), substituted —CH₂CH₂(Ph), -nitro, —CN, —N(R°)₂, —NR°C(O)R°, —NR°C(O)N(R°)₂, —NR°CO₂R°, —C(O)C(O)R°, —C(O)CH₂C(O)R°, —CO₂R°, —C(O)R°, —C(O)N(°)₂, —OC(O)N(R°)₂, —S(O)₂R°, —SO₂N(R°)₂, —S(O)R°, —NR°SO₂N(R°)₂, —NR°SO₂R°, —C(=S)N(R°)₂, —C(=NH)N(RO)₂, —(CH₂)ₘNHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH₂(Ph), or substituted —CH₂(Ph), and m is 0-3.

The term "aryloxyalkyl", as used herein, whether used alone or as part of another group, refers to a substituted or unsubstituted R'—O—R— group, where R' is an aryl group and R is an alkyl group as defined above. Specifically included within the definition of "aryloxyalkyl" are those aromatic ring hydrocarbon chains that are optionally substituted. Suitable substitutions on the unsaturated carbon atom of an aryloxyalkyl include, but are not limited to, halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH₂(Ph), substituted —CH₂(Ph), —CH₂CH₂(Ph), substituted —CH₂CH₂(Ph), -nitro, —CN, —N(R°)₂, —NR°C(O)R°, —NR°C(O)N(R°)₂, —NR°CO₂R°, —C(O)C(O)R°, —C(O)CH₂C(O)R°, —CO₂R°, —C(O)R°, —C(O)N(R°)₂, —OC(O)N(R°)₂, —S(O)₂R°, —SO₂N(R°)₂, —S(O)R°, —NR°SO₂N(R°)₂, —NR°SO₂R°, —C(=S)N(R°)₂, —C(=NH)N(R°)₂, —(CH₂)ₘNHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH₂(Ph), or substituted —CH₂(Ph), and m is 0-3.

The term "heteroaryl", as used herein, whether used alone or as part of another group, refers to a stable 5 to 10 member, substituted or unsubstituted aromatic heterocyclic ring system (monocyclic or bicyclic) containing 3 to 12 carbon atoms, and from 1 to 3 heteroatoms selected from N, O and S. The term "heteroaryl" includes, but is not limited to, benzimidazole, benzisoxazole, benzofuran, benzothiophene, benzoxadiazole, benzoxazole, benzpyrazzole, cinnoline, furan, imidazole, indazole, indole, indolizine, isobenzofuran, isobenzothiophene, isoindole, isoquinoline, isothiazole, isoxazole, naphthyridine, oxazine, oxazole, phthalazine, pteridine, purine, pyran, pyrazine, pyrazole, pyridazine, pyridine, pyrimidine, pyrrole, pyrrolidinone, quinoxaline, quinazoline, quinoline, quinolizine, thiadiazole, thiazole, thiophene and triazole. Specifically included within the definition of "heteroaryl" are those heteroaryl moieties that are optionally substituted. Suitable substituents on the unsaturated carbon atom of a heteroaryl include a halogen, —R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH₂(Ph), substituted —CH₂(Ph), —CH₂CH₂(Ph), substituted —CH₂CH₂(Ph), -nitro, —CN, —N(R°)₂, —NR°C(O)R°, —NR°C(O)N(R°)₂, —NR°CO₂R°, —C(O)C(O)R°, —C(O)CH₂C(O)R°, —CO₂R°, —C(O)R°, —C(O)N(R°)₂, —OC(O)N(R°)₂, —S(O)₂R°, —SO₂N(R°)₂, —S(O)R°, —NR°SO₂N(R°)₂, —NR°SO₂R°, —C(=S)N(R°)₂, —C(=NH)N(R°)₂, —(CH$_2$)$_m$NHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph), and m is 0-3.

The term "heteroaralkyl", as used herein, whether used alone or as part of another group, refers to a substituted or unsubstituted R''—R— group containing 4-13 carbons, unless otherwise indicated, where R'' is a heteroaryl group and R is an alkyl group as defined above. Specifically included within the definition of "heteroaralkyl" are those heteroaralkyl moieties that are optionally substituted. Suitable substituents on the unsaturated carbon atom of a heteroaralkyl include a halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), -nitro, —CN, —N(R°)$_2$, —NR°C(O)R°, —NR°C(O)N(R°)$_2$, —NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)N(R°)$_2$, —(CH$_2$)$_m$NHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph), and m is 0-3.

The term "heteroaralkanoyl" as used herein, whether used alone or as part of another group, refers to a substituted or unsubstituted R''—R—C(=O)— group containing 5 to 14 carbon atoms, where R'' is a heteroaryl group and R is an alkyl group as defined above. Specifically included within the definition of "heteroaralkanoyl" are those heteroaralkanoyl moieties that are optionally substituted. Suitable substituents on the unsaturated carbon atom of a heteroaralkanoyl include a halogen, R°, —OR°, —SR°, 1,2-methylene-dioxy, 1,2-ethylenedioxy, protected OH (such as acyloxy), phenyl (Ph), substituted Ph, —O(Ph), substituted —O(Ph), —CH$_2$(Ph), substituted —CH$_2$(Ph), —CH$_2$CH$_2$(Ph), substituted —CH$_2$CH$_2$(Ph), -nitro, —CN, —N(R°)$_2$, —NR°C(O)R°, —NR°C(O)N(R°)$_2$, —NR°CO$_2$R°, —C(O)C(O)R°, —C(O)CH$_2$C(O)R°, —CO$_2$R°, —C(O)R°, —C(O)N(R°)$_2$, —OC(O)N(R°)$_2$, —S(O)$_2$R°, —SO$_2$N(R°)$_2$, —S(O)R°, —NR°SO$_2$N(R°)$_2$, —NR°SO$_2$R°, —C(=S)N(R°)$_2$, —C(=NH)N(R°)$_2$, —(CH$_2$)$_m$NHC(O)R°; wherein R° is hydrogen, a substituted or unsubstituted aliphatic group, an unsubstituted heteroaryl or heterocyclic ring, phenyl (Ph), substituted Ph, —O(Ph), substituted —O(Ph), —CH$_2$(Ph), or substituted —CH$_2$(Ph), and m is 0-3.

The term "heteroaroyl", as used herein, whether used alone or as part of another group, refers to a substituted or unsubstituted R''—C(=O)— group containing 4 to 13 carbons, where R'' is a heteroaryl group as defined above.

The term "aroyl", as used herein, whether used alone or as part of another group, refers to a substituted or unsubstituted R'—C(=O)— group containing 7 to 13 carbon atoms, where R' is an aryl group as defined above.

The term "aralkanoyl", as used herein, whether used alone or as part of another group, refers to a substituted or unsubstituted R'—R—C(=O)— group containing 7 to 13 carbon atoms, where R' is an aryl group and R is an alkyl group as defined above.

The term "perfluoroalkyl", as used herein, whether used alone or as part of another group, refers to a saturated aliphatic hydrocarbon having 1 to 6 carbon atoms (unless explicitly specified otherwise) and two or more fluorine atoms and includes, but is not limited to, straight or branched chains, such as —CF$_3$, —CH$_2$CF$_3$, —CF$_2$CF$_3$ and —CH(CF$_3$)$_2$.

The term "perfluoroalkoxy", as used herein, whether used alone or as part of another group, refers to the group R$_a$—O—, where R$_a$ is a saturated aliphatic hydrocarbon having 1 to 3 carbon atoms and two or more fluorine atoms and includes, but is not limited to, straight or branched chains, such as —OCF$_3$, —OCH$_2$CF$_3$, —OCF$_2$CF$_3$ and —OCH(CF$_3$)$_2$.

The term "perfluoroalkanoyl", as used herein, whether used alone or as part of another group, refers to the group R—C(=O)— containing 2 to 7 carbon atoms and two or more fluorine atoms.

The term "pharmaceutically acceptable salt", as used herein, refers to salts derived form organic and inorganic acids such as, for example, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known acceptable acids when a compound of this invention contains a basic moiety. Salts may also be formed from organic and inorganic bases, preferably alkali metal salts, for example, sodium, lithium, or potassium, when a compound of this invention contains a carboxylate or phenolic moiety, or similar moiety capable of forming base addition salts.

The term "patient", as used herein, refers to a mammal, preferably a human.

The terms "administer", "administering", or "administration", as used herein, refer to either directly administering a compound or composition to a patient, or administering a prodrug derivative or analog of the compound to the patient, which will form an equivalent amount of the active compound or substance within the patient's body.

The term "carrier", as used herein, shall encompass carriers, excipients, and diluents.

The term "prodrug", as used herein, means a compound which is convertible in vivo by metabolic means (e.g. by hydrolysis) to a compound of formula I.

The compounds of this invention may contain an asymmetric carbon atom and some of the compounds of this invention may contain one or more asymmetric centers and may thus give rise to optical isomers and diastereomers. While shown without respect to stereochemistry in formula I, the present invention includes such optical isomers and diastereomers; as well as the racemic and resolved, enantiomerically pure R and S stereoisomers; as well as other mixtures of the R and S stereoisomers and pharmaceutically acceptable salts thereof.

Where a stereoisomer is preferred, it may in some embodiments be provided substantially free of the corresponding enantiomer. Thus, an enantiomer substantially free of the corresponding enantiomer refers to a compound that is isolated or separated via separation techniques or prepared free of the corresponding enantiomer. "Substantially free", as used herein, means that the compound is made up of a significantly greater proportion of one steriosomer, preferably less than about 50%, more preferably less than about 75%, and even more preferably less than about 90%.

The compounds of this invention may be atropisomers by virtue of possible restricted or slow rotation about the aryl-tricyclicycle single bond. This restricted rotation creates additional chirality and leads to enantiomeric forms. If there is an additional chiral center in the molecule, diastereomers exist and can be seen in the NMR and via other analytical techniques. While shown without respect to atropisomer stereochemistry in Formula I, the present invention includes such atoropisomers (enantiomers and diastereomers; as well as the racemic, resolved, pure diastereomers and mixtures of diastereomers) and pharmaceutically acceptable salts thereof.

Preferred among the above noted $R^1$ groups in formula I are hydrogen, halogen, alkyl and perfluoroalkyl.

Preferred among the above noted $R^2$ groups in formula I are hydrogen, halogen, alkyl and perfluoroalkyl.

Also preferred among the above noted $R^1$ and $R^2$ groups in formula I are $R^1$ and $R^2$, together with the atom to which they are attached, forming a $C_3$-$C_7$ carbocyclyl.

Preferred among the above noted $R^3$ and $R^{17}$ groups in formula I are hydrogen, methyl, and perfluoroalkyl.

Preferred among the above noted $R^4$ groups in formula I are hydrogen, halogen, $C_1$-$C_3$ alkyl, nitro, nitrile, carboxyl, hydroxy, amino, $R^7R^8N$—, and alkoxy.

Preferred among the above noted X groups in formula I are X is nitro, cyano,

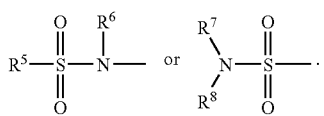

Preferred among the above noted $R^5$ groups in formula I are alkyl, perfluoroalkyl, aryl, heteroaryl, heterocycle, and carbocyclyl.

Preferred among the above noted $R^6$ groups in formula I are hydrogen, $C_1$-$C_3$ alkyl and $C_1$-$C_3$ perfluoroalkyl.

Preferred among the above noted $R^7$ groups in formula I are hydrogen, alkyl, perfluoroalkyl, aryl, heteroaryl, aralkyl, and heteroaralkyl.

Preferred among the above noted $R^8$ groups in formula I are hydrogen, alkyl, perfluoroalkyl, aryl, heteroaryl, aralkyl, and heteroaralkyl.

Also preferred among the above noted $R^7$ and $R^8$ groups are those in which $R^7$ and $R^8$ together have one of the following structures:

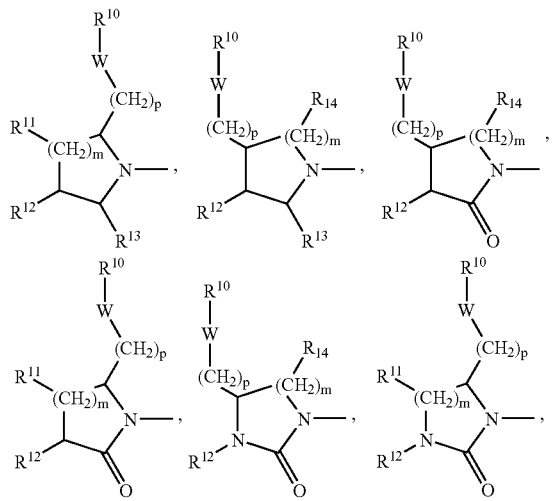

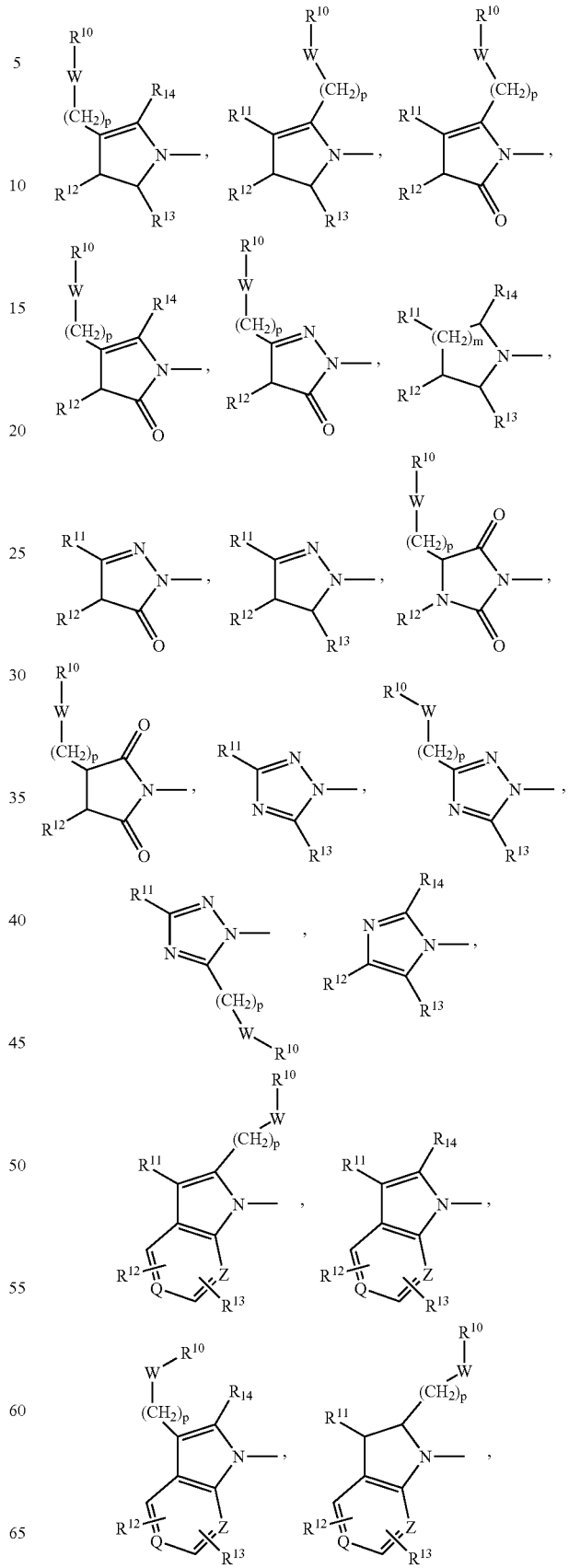

-continued

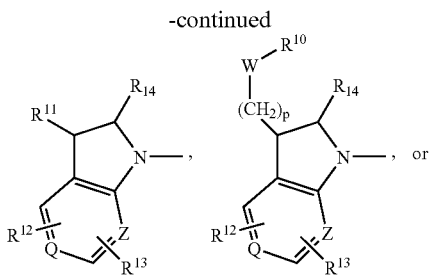

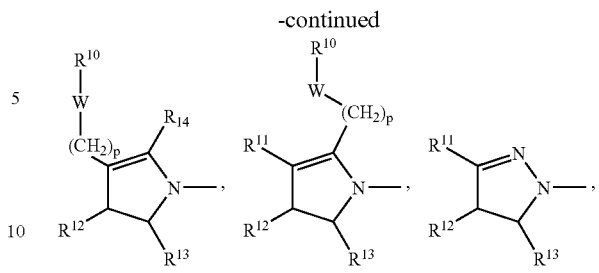

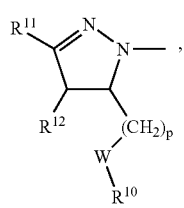

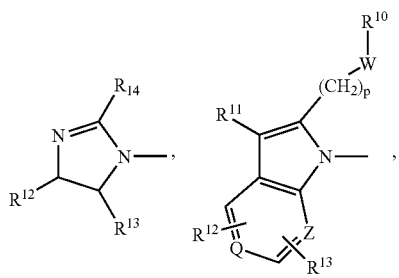

wherein
W is sulfur, oxygen, —NR$^6$—, —CH$_2$—, —C(=O)O—, —C(=O)NR$^6$—, —NR$^6$C(=O)O—,

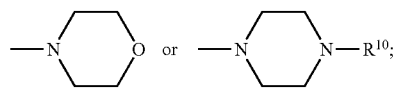

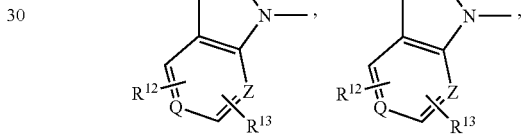

Q and Z can be the same or different, and are independently carbon or nitrogen;

R$^{10}$ is hydrogen, alkyl, aryl, heteroaryl, aralkyl, heteroaralkyl, alkanoyl, perfluoroalkanoyl, aroyl, heteroaroyl, aralkanoyl, carbocycl, or heteroaralkanoyl;

R$^{11}$, R$^{12}$, R$^{13}$ and R$^{14}$ can be the same or different, and are independently hydrogen, halogen, hydroxyl, nitrile, nitro, R$^7$R$^8$N—, R$^7$R$^8$NC(O)—, —NR$^6$C(O)R$^9$, —C(O)$_2$R$^9$, —C(O)H, —C(O)R$^9$, alkyl, alkanoyl, perfluoroalkanoyl, aroyl, heteroaroyl, aralkanoyl, heteroaralkanoyl, or R$^{11}$ and R$^{12}$ together form an optionally substituted ring comprising 5 to 7 atoms selected from C, N, S and O, or R$^{12}$ and R$^{13}$ together form an optionally substituted ring comprising 5 to 7 atoms selected from C, N, S and O; and each of m and p are, independently, an integer of 0 to 2.

Particularly preferred R$^7$ and R$^8$ groups are those having formula:

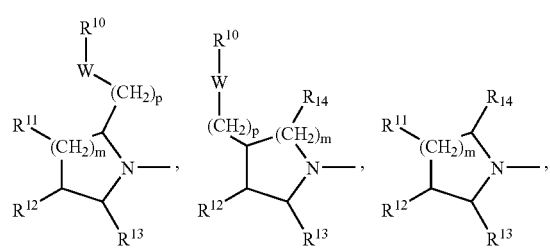

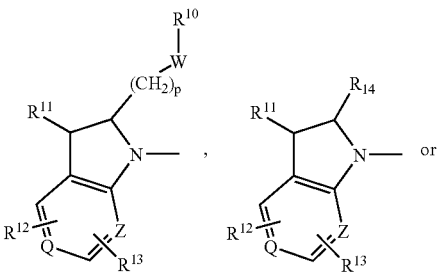

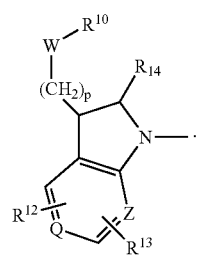

Preferred among the above noted R$^9$ groups in formula I are hydrogen, alkyl, perfluoroalkyl, aryl, heteroaryl, aralkyl, heteroaralkyl, and C$_3$-C$_{12}$ carbocyclyl.

Preferred among the above noted R$^{10}$ groups in formula I are hydrogen, alkyl, aryl, heteroaryl, aralkyl, heteroaralkyl, alkanoyl, aroyl, heteroaroyl, aralkanoyl, and heteroaralkanoyl.

Preferred among the above noted $R^{11}$, $R^{12}$, $R^{13}$ and $R^{14}$ groups in formula I are independently hydrogen, halogen, hydroxyl, nitrile, nitro, $R^7R^8N$—, $R^7R^8NC(O)$—, —$NR^6C(O)R^9$, —$C(O)_2R^9$, —$C(O)H$, —$C(O)R^9$, alkyl, perfluoroalkyl, alkanoyl, aroyl, heteroaroyl, aralkanoyl, heteroaralkanoyl, $R^{11}$ and $R^{12}$ when taken together form an optionally substituted ring comprising 5 to 7 atoms selected from C, N, S and O, and $R^{12}$ and $R^{13}$ when taken together form an optionally substituted ring comprising 5 to 7 atoms selected from C, N, S and O.

Preferred among the above noted W groups in formula I are oxygen, —$NR^6$—, —$CH_2$—, —$C(=O)O$—, —$C(=O)NR^6$—, and —$NR^6C(=O)O$—.

Preferred among the above noted Q groups in formula I are carbon and nitrogen.

Preferred among the above noted Z groups in formula I are carbon and nitrogen.

Preferably, n is 1.

Preferred among the above noted $R^{16}$ and $R^{17}$ groups in formula I are hydrogen and methyl.

In one embodiment, the present invention is also directed to compounds of formula II that are useful in the preparation of compounds of formula I:

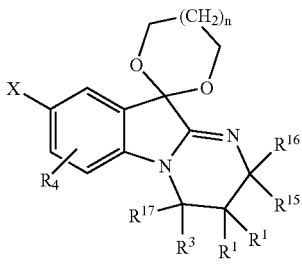

II or a prodrug, stereoisomer, or pharmaceutically-acceptable salt thereof;

wherein:
$R^1$ and $R^2$ are independently hydrogen, halogen, alkyl, aryl, heteroaryl, or $R^1$ and $R^2$ together with the carbon atom to which they are attached, form a $C_3$-$C_7$ carbocyclyl;

$R^3$ and $R^{17}$ are independently hydrogen or alkyl;

$R^{15}$ and $R^{16}$ are independently, hydrogen, alkyl, or aryl, provided that $R^{15}$ and $R^{16}$ are not both aryl;

$R^4$ is hydrogen, halogen, alkyl, nitro, nitrile, carboxyl, hydroxy, amino, $R^7R^8N$—, alkoxy, or perfluoroalkoxy;

X is nitro, cyano, alkyl, perfluoroalkoxy, halogen,

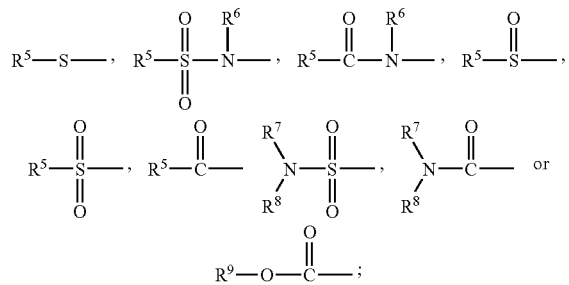

$R^5$ is alkyl, aryl, heteroaryl, heterocycle, or carbocyclyl;
$R^6$ is hydrogen or $C_1$-$C_3$ alkyl;

$R^7$ and $R^8$ are independently hydrogen, alkyl, aryl, heteroaryl, aralkyl, heteroaralkyl, alkanoyl, perfluoroalkanoyl, aroyl, heteroaroyl, aralkanoyl, heteroaralkanoyl, or $R^7$ and $R^8$ together with the nitrogen to which they are attached form a 5 to 10 member optionally substituted monocyclic or bicyclic ring system, which may further contain heteroatoms selected from oxygen, nitrogen or sulfur, provided that no ring may contain more than 3 heteroatoms;

$R^9$ is hydrogen, alkyl, aryl, heteroaryl, aralkyl, $C_4$-$C_{12}$ heteroaralkyl, or $C_3$-$C_{12}$ carbocyclyl; and n is an integer of 0 or 1.

The following compounds are particularly preferred:
8-{[(2S)-2-(Methoxymethyl)pyrrolidin-1-yl]sulfonyl}-3,4-dihydropyrimido[1,2-a]indol-10(2H)-one;
8-{[(2S)-2-(Methoxymethyl)pyrrolidin-1-yl]sulfonyl}-3,3-dimethyl-3,4-dihydropyrimido[1,2-a]indol-10(2H)-one;
8-{[(2S)-2-(Phenoxymethyl)pyrrolidin-1-yl]sulfonyl}-3,4-dihydropyrimido[1,2-a]indol-10(2H)-one;
3,3-Dimethyl-8-{[(2S)-2-(phenoxymethyl)pyrrolidin-1-yl]sulfonyl}-3,4-dihydropyrimido[1,2-a]indol-10(2H)-one;
7-Chloro-8-{[(2S)-2-(methoxymethyl)pyrrolidin-1-yl-]sulfonyl}-3,4-dihydropyrimido[1,2-a]indol-10(2H)-one;
8-{[(2R)-2-(Methoxymethyl)pyrrolidin-1-yl]sulfonyl}-3,3-dimethyl-3,4-dihydropyrimido[1,2-a]indol-10(2H)-one;
N-Methyl-10-oxo-2,3,4,10-tetrahydropyrimido[1,2-a]indole-8-sulfonamide;
8-{[(2S)-2-(Hydroxymethyl)pyrrolidin-1-yl]sulfonyl}-3,3-dimethyl-3,4-dihydropyrimido[1,2-a]indol-10(2H)-one;
3,3-Dimethyl-8-(pyrrolidin-1-ylsulfonyl)-3,4-dihydropyrimido[1,2-a]indol-10(2H)-one;
7-Chloro-8-nitro-3,4-dihydropyrimido[1,2-a]indol-10(2H)-one;
N-(10-Oxo-2,3,4,10-tetrahydropyrimido[1,2-a]indol-8-yl)benzamide;
3,3-Dimethyl-10-oxo-2,3,4,10-tetrahydropyrimido[1,2-a]indole-8-carbonitrile;
8-({(2S)-2-[(4-Methoxyphenoxy)methyl]pyrrolidin-1-yl}sulfonyl)-3,3-dimethyl-3,4-dihydropyrimido[1,2-a]indol-10(2H)-one;
8-({(2S)-2-[(4-Fluorophenoxy)methyl]pyrrolidin-1-yl}sulfonyl)-3,3-dimethyl-3,4-dihydropyrimido[1,2-a]indol-10(2H)-one;
8-({(2S)-2-[(4-Chlorophenoxy)methyl]pyrrolidin-1-yl}sulfonyl)-3,3-dimethyl-3,4-dihydropyrimido[1,2-a]indol-10(2H)-one;
3,3-Dimethyl-8-({(2S)-2-[(4-methylphenoxy)methyl]pyrrolidin-1-yl}sulfonyl)-3,3-dimethyl-3,4-dihydropyrimido[1,2-a]indol-10(2H)-one;
8-({(2S)-2-[(2-Chloro-4-methoxyphenoxy)methyl]pyrrolidin-1-yl}sulfonyl)-3,3-dimethyl-3,4-dihydropyrimido[1,2-a]indol-10(2H)-one;
8-({(2S)-2-[(2-Chloro-4-methylphenoxy)methyl]pyrrolidin-1-yl}sulfonyl)-3,3-dimethyl-3,4-dihydropyrimido[1,2-a]indol-10(2H)-one;
8-({(2S)-2-[(4-Acetyl-2-methylphenoxy)methyl]pyrrolidin-1-yl}sulfonyl)-3,3-dimethyl-3,4-dihydropyrimido[1,2-a]indol-10(2H)-one;
8-({(2S)-2-[(4-tert-Butylphenoxy)methyl]pyrrolidin-1-yl}sulfonyl)-3,3-dimethyl-3,4-dihydropyrimido[1,2-a]indol-10(2H)-one;
8-({(2S)-2-[(4-Acetylphenoxy)methyl]pyrrolidin-1-yl}sulfonyl)-3,3-dimethyl-3,4-dihydropyrimido[1,2-a]indol-10(2H)-one;
8-({(2S)-2-[(4-Fluoro-3-methylphenoxy)methyl]pyrrolidin-1-yl}sulfonyl)-3,3-dimethyl-3,4-dihydropyrimido[1,2-a]indol-10(2H)-one;

3,3-Dimethyl-8-({(2S)-2-[(3-(trifluoromethyl)phenoxy)methyl]pyrrolidin-1-yl}sulfonyl)-3,4-dihydropyrimido[1,2-a]indol-10(2H)-one;
8-(2,3-Dihydro-1H-indol-1-ylsulfonyl)-3,3-dimethyl-3,4-dihydropyrimido[1,2-a]indol-10(2H)-one;
8-{[(2S)-2-(Methoxymethyl)-2,3-dihydro-1H-indol-1-yl]sulfonyl}-3,3-dimethyl-3,4-dihydropyrimido[1,2-a]indol-10(2H)-one;
3,3-Dimethyl-8-{[(2S)-2-(phenoxymethyl)-2,3-dihydro-1H-indol-1-yl]sulfonyl}-3,4-dihydropyrimido[1,2-a]indol-10(2H)-one;
8-[((2S)-2-{[(2-Bromopyridin-3-yl)oxy]methyl}pyrrolidin-1-yl)sulfonyl]-3,3-dimethyl-3,4-dihydropyrimido[1,2-a]indol-10(2H)-one;
8-({(2S)-2-[(Cyclohexylamino)methyl]pyrrolidin-1-yl}sulfonyl)-3,3-dimethyl-3,4-dihydropyrimido[1,2-a]indol-10(2H)-one;
N-(3,3-Dimethyl-10-oxo-2,3,4,10-tetrahydropyrimido[1,2-a]indol-8-yl)benzenesulfonamide;
3,3-Dimethyl-8-({(2S)-2-[(pyridin-2-yloxy)methyl]pyrrolidin-1-yl}sulfonyl)-3,4-dihydropyrimido[1,2-a]indol-10(2H)-one;
8-[((2S)-2-{[(5-Chloropyridin-2-yl)oxy]methyl}pyrrolidin-1-yl)sulfonyl]-3,3-dimethyl-3,4-dihydropyrimido[1,2-a]indol-10(2H)-one;
8-[((2S)-2-{[(6-Chloropyridin-2-yl)oxy]methyl}pyrrolidin-1-yl)sulfonyl]-3,3-dimethyl-3,4-dihydropyrimido[1,2-a]indol-10(2H)-one;
3,3-Dimethyl-8-[((2S)-2-{[(6-methylpyridin-2-yl)oxy]methyl}pyrrolidin-1-yl)sulfonyl]-3,4-dihydropyrimido[1,2-a]indol-10(2H)-one;
3,3-Dimethyl-8-{[(2S)-2-({[5-(trifluoromethyl)pyridin-2-yl]oxy}methyl)pyrrolidin-1-yl]sulfonyl}-3,4-dihydropyrimido[1,2-a]indol-10(2H)-one;
8-[((2S)-2-{[(2-chloropyridin-3-yl)oxy]methyl}pyrrolidin-1-yl)sulfonyl]-3,3-dimethyl-3,4-dihydropyrimido[1,2-a]indol-10(2H)-one;
3,3-Dimethyl-8-[((2S)-2-{[(6-methylpyridin-3-yl)oxy]methyl}pyrrolidin-1-yl)sulfonyl]-3,4-dihydropyrimido[1,2-a]indol-10(2H)-one;
Methyl 5-({(2S)-1-[(3,3-dimethyl-10-oxo-2,3,4,10-tetrahydropyrimido[1,2-a]indol-8-yl)sulfonyl]pyrrolidin-2-yl}methoxy)nicotinate;
8-[((2S)-2-{[(2-Iodo-6-methylpyridin-3-yl)oxy]methyl}pyrrolidin-1-yl)sulfonyl]-3,3-dimethyl-3,4-dihydropyrimido[1,2-a]indol-10(2H)-one;
3,3-Dimethyl-8-({(2S)-2-[(pyridin-3-yloxy)methyl]pyrrolidin-1-yl}sulfonyl)-3,4-dihydropyrimido[1,2-a]indol-10(2H)-one;
8-[((2S)-2-{[(5-Chloropyridin-3-yl)oxy]methyl}pyrrolidin-1-yl)sulfonyl]-3,3-dimethyl-3,4-dihydropyrimido[1,2-a]indol-10(2H)-one;
3,3-Dimethyl-8-[((2S)-2-{[(2-methylpyridin-3-yl)oxy]methyl}pyrrolidin-1-yl)sulfonyl]-3,4-dihydropyrimido[1,2-a]indol-10(2H)-one;
3-Bromo-N-(3,3-dimethyl-10-oxo-2,3,4,10-tetrahydropyrimido[1,2-a]indol-8-yl)benzenesulfonamide;
N-(3,3-Dimethyl-10-oxo-2,3,4,10-tetrahydropyrimido[1,2-a]indol-8-yl)-4-methylbenzenesulfonamide;
3-Chloro-N-(3,3-dimethyl-10-oxo-2,3,4,10-tetrahydropyrimido[1,2-a]indol-8-yl)-4-fluorobenzenesulfonamide;
3,4-Dichloro-N-(3,3-dimethyl-10-oxo-2,3,4,10-tetrahydropyrimido[1,2-a]indol-8-yl)benzenesulfonamide;
N-(3,3-Dimethyl-10-oxo-2,3,4,10-tetrahydropyrimido[1,2-a]indol-8-yl)-3-(trifluoromethyl)benzenesulfonamide;
N-(3,3-Dimethyl-10-oxo-2,3,4,10-tetrahydropyrimido[1,2-a]indol-8-yl)-2-fluorobenzenesulfonamide;
N-(3,3-Dimethyl-10-oxo-2,3,4,10-tetrahydropyrimido[1,2-a]indol-8-yl)-4-methoxybenzenesulfonamide;
N-(3,3-Dimethyl-10-oxo-2,3,4,10-tetrahydropyrimido[1,2-a]indol-8-yl)-4-fluorobenzenesulfonamide;
4-Chloro-N-(3,3-dimethyl-10-oxo-2,3,4,10-tetrahydropyrimido[1,2-a]indol-8-yl)benzenesulfonamide;
2-Bromo-N-(3,3-dimethyl-10-oxo-2,3,4,10-tetrahydropyrimido[1,2-a]indol-8-yl)benzenesulfonamide;
N-(3,3-Dimethyl-10-oxo-2,3,4,10-tetrahydropyrimido[1,2-a]indol-8-yl)-3-methoxybenzenesulfonamide;
N-(3,3-Dimethyl-10-oxo-2,3,4,10-tetrahydropyrimido[1,2-a]indol-8-yl)-4-(trifluoromethoxy)benzenesulfonamide;
N-(3,3-Dimethyl-10-oxo-2,3,4,10-tetrahydropyrimido[1,2-a]indol-8-yl)-3,5-bis(trifluoromethyl)benzenesulfonamide;
3,3-Dimethyl-8-{[(2S)-2-(morpholin-4-ylmethyl)pyrrolidin-1-yl]sulfonyl}-3,4-dihydropyrimido[1,2-a]indol-10(2H)-one;
Ethyl 4-({(2S)-1-[(3,3-dimethyl-10-oxo-2,3,4,10-tetrahydropyrimido[1,2-a]indol-8-yl)sulfonyl]pyrrolidin-2-yl}methyl)piperazine-1-carboxylate;
8-({(2S)-2-[(Cyclopentylamino)methyl]pyrrolidin-1-yl}sulfonyl)-3,3-dimethyl-3,4-dihydropyrimido[1,2-a]indol-10(2H)-one;
3,3-Dimethyl-8-{[(2S)-2-(phenoxymethyl)pyrrolidin-1-yl]carbonyl}-3,4-dihydropyrimido[1,2-a]indol-10(2H)-one;
8-({(2S)-2-[(4-Methoxyphenoxy)methyl]pyrrolidin-1-yl}sulfonyl)-3,3-dimethyl-3,4-dihydropyrimido[1,2-a]indol-10(2H)-one;
8-({(2S)-2-[(4-Fluorophenoxy)methyl]pyrrolidin-1-yl}sulfonyl)-3,3-dimethyl-3,4-dihydropyrimido[1,2-a]indol-10(2H)-one;
8-({(2S)-2-[(4-Chlorophenoxy)methyl]pyrrolidin-1-yl}sulfonyl)-3,3-dimethyl-3,4-dihydropyrimido[1,2-a]indol-10(2H)-one;
3,3-Dimethyl-8-({(2S)-2-[(4-methylphenoxy)methyl]pyrrolidin-1-yl}sulfonyl)-3,4-dihydropyrimido[1,2-a]indol-10(2H)-one;
8-({(2S)-2-[(2-Chloro-4-methoxyphenoxy)methyl]pyrrolidin-1-yl}sulfonyl)-3,3-dimethyl-3,4-dihydropyrimido[1,2-a]indol-10(2H)-one;
8-({(2S)-2-[(2-Chloro-4-methylphenoxy)methyl]pyrrolidin-1-yl}sulfonyl)-3,3-dimethyl-3,4-dihydropyrimido[1,2-a]indol-10(2H)-one;
8-({(2S)-2-[(4-Acetyl-2-methylphenoxy)methyl]pyrrolidin-1-yl}sulfonyl)-3,3-dimethyl-3,4-dihydropyrimido[1,2-a]indol-10(2H)-one;
8-({(2S)-2-[(4-Tert-butylphenoxy)methyl]pyrrolidin-1-yl}sulfonyl)-3,3-dimethyl-3,4-dihydropyrimido[1,2-a]indol-10(2H)-one;
8-({(2S)-2-[(4-Acetylphenoxy)methyl]pyrrolidin-1-yl}sulfonyl)-3,3-dimethyl-3,4-dihydropyrimido[1,2-a]indol-10(2H)-one;
8-({(2S)-2-[(4-Fluoro-3-methylphenoxy)methyl]pyrrolidin-1-yl}sulfonyl)-3,3-dimethyl-3,4-dihydropyrimido[1,2-a]indol-10(2H)-one;
3,3-Dimethyl-8-[((2S)-2-{[3-(trifluoromethyl)phenoxy]methyl}pyrrolidin-1-yl)sulfonyl]-3,4-dihydropyrimido[1,2-a]indol-10(2H)-one;
8-(2,3-Dihydro-1H-indol-1-ylsulfonyl)-3,3-dimethyl-3,4-dihydropyrimido[1,2-a]indol-10(2H)-one;
8-{[(2S)-2-(Methoxymethyl)-2,3-dihydro-1H-indol-1-yl]sulfonyl}-3,3-dimethyl-3,4-dihydropyrimido[1,2-a]indol-10(2H)-one;
3,3-Dimethyl-8-{[(2S)-2-(phenoxymethyl)-2,3-dihydro-1H-indol-1-yl]sulfonyl}-3,4-dihydropyrimido[1,2-a]indol-10(2H)-one;

8-[((2S)-2-{[(2-Bromopyridin-3-yl)oxy]methyl}pyrrolidin-1-yl)sulfonyl]-3,3-dimethyl-3,4-dihydropyrimido[1,2-a]indol-10(2H)-one;

3,3-Dimethyl-8-({(2S)-2-[(pyridin-2-yloxy)methyl]pyrrolidin-1-yl}sulfonyl)-3,4-dihydropyrimido[1,2-a]indol-10(2H)-one;

8-[((2S)-2-{[(5-Chloropyridin-2-yl)oxy]methyl}pyrrolidin-1-yl)sulfonyl]-3,3-dimethyl-3,4-dihydropyrimido[1,2-a]indol-10(2H)-one;

8-[((2S)-2-{[(6-Chloropyridin-2-yl)oxy]methyl}pyrrolidin-1-yl)sulfonyl]-3,3-dimethyl-3,4-dihydropyrimido[1,2-a]indol-10(2H)-one;

3,3-Dimethyl-8-[((2S)-2-{[(6-methylpyridin-2-yl)oxy]methyl}pyrrolidin-1-yl)sulfonyl]-3,4-dihydropyrimido[1,2-a]indol-10(2H)-one;

3,3-Dimethyl-8-{[(2S)-2-({[5-(trifluoromethyl)pyridin-2-yl]oxy}methyl)pyrrolidin-1-yl]sulfonyl}-3,4-dihydropyrimido[1,2-a]indol-10(2H1)-one;

8-[((2S)-2-{[(2-Chloropyridin-3-yl)oxy]methyl}pyrrolidin-1-yl)sulfonyl]-3,3-dimethyl-3,4-dihydropyrimido[1,2-a]indol-10(2H)-one;

3,3-Dimethyl-8-[((2S)-2-{[(6-methylpyridin-3-yl)oxy]methyl}pyrrolidin-1-yl)sulfonyl]-3,4-dihydropyrimido[1,2-a]indol-10(2H)-one;

Methyl 5-({(2S)-1-[(3,3-dimethyl-10-oxo-2,3,4,10-tetrahydropyrimido[1,2-a]indol-8-yl)sulfonyl]pyrrolidin-2-yl}methoxy)nicotinate;

8-[((2S)-2-{[(2-Iodo-6-methylpyridin-3-yl)oxy]methyl}pyrrolidin-1-yl)sulfonyl]-3,3-dimethyl-3,4-dihydropyrimido[1,2-a]indol-10(2H)-one;

3,3-Dimethyl-8-({(2S)-2-[(pyridin-3-yloxy)methyl]pyrrolidin-1-yl}sulfonyl)-3,4-dihydropyrimido[1,2-a]indol-10(2H)-one;

8-[((2S)-2-{[(5-Chloropyridin-3-yl)oxy]methyl}pyrrolidin-1-yl)sulfonyl]-3,3-dimethyl-3,4-dihydropyrimido[1,2-a]indol-10(2H)-one;

3,3-Dimethyl-8-[((2S)-2-{[(2-methylpyridin-3-yl)oxy]methyl}pyrrolidin-1-yl)sulfonyl]-3,4-dihydropyrimido[1,2-a]indol-10(2H)-one;

3,3-Dimethyl-8-({(2S)-2-[(pyridin-2-yloxy)methyl]pyrrolidin-1-yl}sulfonyl)-3,4-dihydropyrimido[1,2-a]indol-10(2H)-one;

8-({(2S)-2-[(Cyclohexylamino)methyl]pyrrolidin-1-yl}sulfonyl)-3,3-dimethyl-3,4-dihydropyrimido[1,2-a]indol-10(2H)-one;

3,3-Dimethyl-8-{[(2S)-2-(morpholin-4-ylmethyl)pyrrolidin-1-yl]sulfonyl}-3,4-dihydropyrimido[1,2-a]indol-10(2H)-one;

Ethyl 4-({(2S)-1-[(3,3-dimethyl-10-oxo-2,3,4,10-tetrahydropyrimido[1,2-a]indol-8-yl)sulfonyl]pyrrolidin-2-yl}methyl)piperazine-1-carboxylate;

8-({(2S)-2-[(Cyclopentylamino)methyl]pyrrolidin-1-yl}sulfonyl)-3,3-dimethyl-3,4-dihydropyrimido[1,2-a]indol-10(2H)-one;

3,3-Dimethyl-8-({(2S)-2-[(4-methylpiperazin-1-yl)methyl]pyrrolidin-1yl}sulfonyl)-3,4-dihydropyrimido[1,2-a]indol-10(2H)-one;

N-(3,3-Dimethyl-10-oxo-2,3,4,10-tetrahydropyrimido[1,2-a]indol-8-yl)benzenesulfonamide;

3-Bromo-N-(3,3-dimethyl-10-oxo-2,3,4,10-tetrahydropyrimido[1,2-a]indol-8-yl)benzenesulfonamide;

N-(3,3-Dimethyl-10-oxo-2,3,4,10-tetrahydropyrimido[1,2-a]indol-8-yl)-4-methylbenzenesulfonamide;

3-Chloro-N-(3,3-dimethyl-10-oxo-2,3,4,10-tetrahydropyrimido[1,2-a]indol-8-yl)-4-fluorobenzenesulfonamide;

3,3-Dimethyl-8-{[(2S)-2-(phenoxymethyl)pyrrolidin-1-yl]carbonyl}-3,4-dihydropyrimido[1,2-a]indol-10(2H)-one;

N-(3,3-Dimethyl-10-oxo-2,3,4,10-tetrahydropyrimido[1,2-a]indol-8-yl)-3-(trifluoromethyl)benzenesulfonamide;

8-{[(2S)-2-(Methoxymethyl)pyrrolidin-1-yl]carbonyl}-3,3-dimethyl-3,4-dihydropyrimido[1,2-a]indol-10(2H)-one;

3,3-Dimethyl-10-oxo-N-phenyl-2,3,4,10-tetrahydropyrimido[1,2-a]indole-8-carboxamide;

N-Cyclopentyl-3,3-dimethyl-10-oxo-2,3,4,10-tetrahydropyrimido[1,2-a]indole-8-carboxamide;

3,3-Dimethyl-8-(pyrrolidin-1-ylcarbonyl)-3,4-dihydropyrimido[1,2-a]indol-10(2H)-one;

3,3-Dimethyl-8-(piperidin-1-ylcarbonyl)-3,4-dihydropyrimido[1,2-a]indol-10(2H)-one;

8-(2,3-Dihydro-1H-indol-1-ylcarbonyl)-3,3-dimethyl-3,4-dihydropyrimido[1,2-a]indol-10(2H)-one;

3,3-Dimethyl-8-[(4-methylpiperazin-1-yl)carbonyl]-3,4-dihydropyrimido[1,2-a]indol-10(2H)-one;

8-[(4-Acetylpiperazin-1-yl)carbonyl]-3,3-dimethyl-3,4-dihydropyrimido[1,2-a]indol-10(2H)-one;

8'-{[(2S)-2-(Methoxymethyl)pyrrolidin-1-yl]sulfonyl}spiro[cyclopentane-1,3'-pyrimido[1,2-a]indol]-10'(2'H)-one;

8'-{[(2S)-2-(Methoxymethyl)pyrrolidin-1-yl]sulfonyl}spiro[cyclohexane-1,3'-pyrimido[1,2-a]indol]-10'(2'H)-one;

8'-{[(2S)-2-(Methoxymethyl)pyrrolidin-1-yl]sulfonyl}spiro[cyclobutane-1,3'-pyrimido[1,2-a]indol]-10'(2'H)-one;

8'-{[(2S)-2-(Phenoxymethyl)pyrrolidin-1-yl]sulfonyl}spiro[cyclopentane-1,3'-pyrimido[1,2-a]indol]-10'(2'H)-one;

8'-{[(2S)-2-(Phenoxymethyl)pyrrolidin-1-yl]sulfonyl}spiro[cyclohexane-1,3'-pyrimido[1,2-a]indol]-10'(2'H)-one;

8'-{[(2S)-2-(Phenoxymethyl)pyrrolidin-1-yl]sulfonyl}spiro[cyclobutane-1,3'-pyrimido[1,2-a]indol]-10'(2'H)-one;

8'-{[(2S)-2-(morpholin-4-ylmethyl)pyrrolidin-1-yl]sulfonyl}spiro[cyclopentane-1,3'-pyrimido[1,2-a]indol]-10'(2'H)-one;

8'-({(2S)-2-[(4-Methylpiperazin-1-yl)methyl]pyrrolidin-1-yl}sulfonyl)spiro[cyclopentane-1,3'-pyrimido[1,2-a]indol]-10'(2'H)-one;

8'-{[(2S)-2-(methoxymethyl)pyrrolidin-1-yl]sulfonyl}spiro[cycloheptane-1,3'-pyrimido[1,2-a]indol]-10'(2'H)-one;

2-Methyl-8-(pyrrolidin-1-ylsulfonyl)-3,4-dihydropyrimido[1,2-a'indol-10 (2H)-one;

8'-{[(2S)-2-(Methoxymethyl)pyrrolidinyl]sulfonyl}-3',4'-dihydrospiro(1,3-dioxane-2,10'(2'H)-pyrimido(1,2-a)indole)

8'-{[(2S)-2-(Phenoxymethyl)pyrrolidin-1-yl]sulfonyl}-3',4'-dihydro-2'H-spiro[1,3-dioxane-2,10'-pyrimido[1,2-a]indole]

3',3'-Dimethyl-8'-{[(2S)-2-(phenoxymethyl)pyrrolidin-1-yl]sulfonyl}-3',4'-dihydro-2'H-spiro[1,3-dioxane-2,10'-pyrimido[1,2-a]indole];

8'-{[(2R)-2-(Methoxymethyl)pyrrolidin-1-yl]sulfonyl}-3',3'-dimethyl-3',4'-dihydro-2'H-spiro[1,3-dioxane-2,10'pyrimido[1,2-a]indole];

N-Benzyl-N-methyl-3',4'-dihydrospiro[1,3-dioxane-2,10'(2'H)-pyrimido[1,2-alpha]-indole]-8'-sulfonamide;

8'-({(2S)-2-[(Benzyloxy)methyl]pyrrolidin-1-yl}sulfonyl)-3',3'-dimethyl-3',4'-dihydro-2'H-spiro[1,3-dioxane-2,10'-pyrimido[1,2-a]indole];

3',3'-Dimethyl-8'-(pyrrolidin-1-ylsulfonyl)-3',4'-dihydro-2'H-spiro[1,3-dioxane-2,10'-pyrimido[1,2-a]indole];

3',4'-Dihydro-2'H-spiro[1,3-dioxane-2,10'-pyrimido[1,2-a]indol]-8'-amine;

N-3',4'-Dihydro-2'H-spiro[1,3-dioxane-2,10'-pyrimido[1,2-a]indol]-8'-ylbenzamide;

3',3'-dimethyl-3',4'-dihydro-2'H-spiro[1,3-dioxane-2,10'-pyrimido[1,2-a]indole-8'-carbonitrile;

{(2S)-1-[(3',3'-Dimethyl-3',4'-dihydro-2'H-spiro[1,3-dioxane-2,10'-pyrimido[1,2a]indol]-8'-yl)sulfonyl]pyrrolidin-2-yl}methanol;

{(2S)-1-[(3',3'-Dimethyl-3',4'-dihydro-2'H-spiro[1,3-dioxane-2,10'-pyrimido[1,2-a]indol]-8'-yl)sulfonyl]pyrrolidin-2-yl}methyl 4-methylbenzenesulfonate;

3',3'-Dimethyl-3',4'-dihydro-2'H-spiro[1,3-dioxane-2,10'-pyrimido[1,2-a]indol]-8'amine;

N-(3',3'-Dimethyl-3',4'-dihydro-2'H-spiro[1,3-dioxane-2,10'-pyrimido[1,2-a]indol]-8'-yl)benzenesulfonamide;

8'-Bromo-3',3'-dimethyl-3',4'-dihydro-2'H-spiro[1,3-dioxane-2,10'-pyrimido[1,2-a]indole];

3',3'-Dimethyl-8'-vinyl-3',4'-dihydro-2'H-spiro 1,3-dioxane-2,10'-pyrimido[1,2-a]indole];

Methyl 3',3'-dimethyl-3',4'-dihydro-2'H-spiro[1,3-dioxane-2,10'-pyrimido[1,2-a]indole]-8'-carboxylate;

3',3'-Dimethyl-3',4'-dihydro-2'H-spiro[1,3-dioxane-2,10'-pyrimido[1,2-a]indole]-carboxylic acid;

2'-Methyl-8'-(pyrrolidin-1-ylsulfonyl)-3',4'-dihydro-2'H-spiro[1,3-dioxane-2,10'-pyrimido[1,2-a]indole];

8'-{[(2S)-2-(methoxymethyl)pyrrolidin-1-yl]sulfonyl}spiro[cycloheptane-1,3'-pyrimido[1,2-a]indol]-10'(2'H)-one;

or pharmaceutically acceptable salts thereof.

Scheme 1

General scheme for the preparation of compounds of formula I:

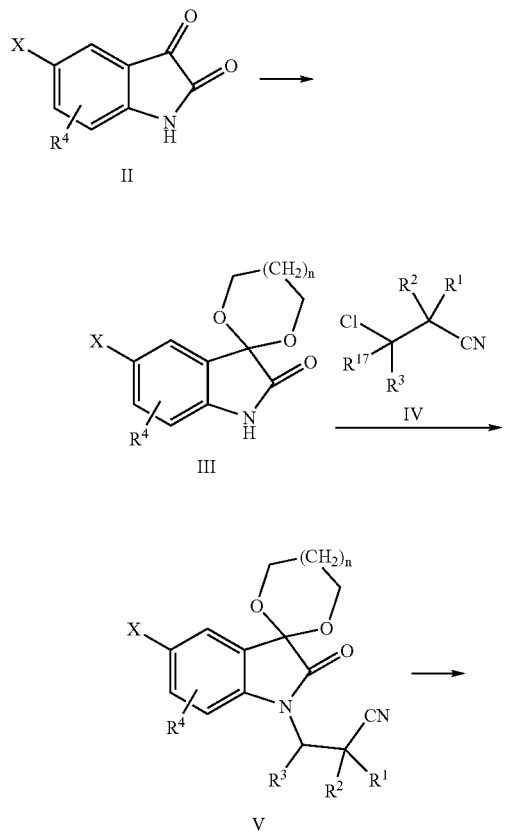

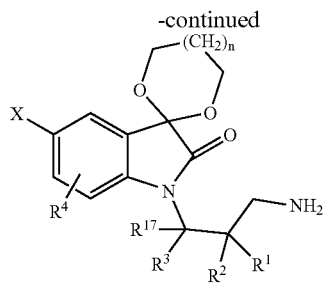

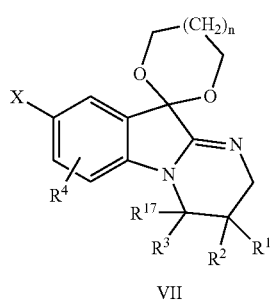

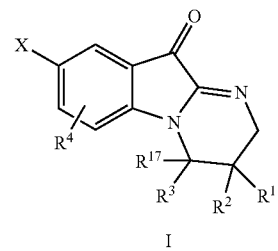

Pyrimidoindolones of formula I where X, $R^1$, $R^2$, $R^3$, $R^4$, $R^{17}$, and n are defined above can be prepared from isatins of compound II where X and $R^4$ are defined as above. The starting isatin of compound II may be either commercially available or can be prepared using standard synthetic methodology as described in Schemes 2, 5 and 6 below, or as described by Popp, F. D., *Advances in Heterocyclic Chemistry*, 1975, 18: 1-58, or as described by Sandmeyer, T., *Helvetica. Chim. Acta*, 1919, 2: 234-242. The ketone in compound II can be protected to prevent unwanted side reactions by using a suitable protecting group such as an acyclic (dimethyl or diisopropyl) or cyclic (dioxolane, dioxane) ketal. In this scheme, protection of the isatin ketone II is accomplished using a suitable protecting agent such as 1,3-propanediol in the presence of an acid such as $H_2SO_4$ or p-toluenesulfonic acid under refluxing conditions in benzene or toluene while azeotropically removing $H_2O$ with a Dean-Stark trap to give ketal of compound III. The species of the ketone protecting group employed is not critical so long as the derivatized ketone is stable to the conditions of subsequent reaction(s) and can be removed at the appropriated point without disrupting the remainder of the molecule. Further examples of these groups are found in T. W. Greene and P. G. M. Wuts, "Protective Groups in Organic Synthesis," $2^{nd}$ ed. John Wiley and Sons, New York, N.Y., Chapter 4, incorporated herein by reference. Alkylating the protected isatin III utilizing the desired alkylating reagent of compound IV where $R^1$, $R^2$ and $R^3$ are defined above is accomplished using a suitable base such as NaH or $K_2CO_3$ in a nonprotic solvent such as THF at temperatures ranging from 0° C. to reflux. The alkylating reagent is either commercially available or is prepared using standard synthetic methodology as described by Cliffe, I. A., Syn. Comm. 20(12) 1757, 1990. The reduction of nitrile V can be accomplished by catalytic hydrogenation using a suitable nickel or palladium catalyst in an organic solvent such as ethanol, methanol or THF containing ammonia to prevent dimerization to give the amine of compound VI. Compound VI can be subjected to cyclodehydration conditions by heating at 100° C. in a suitable solvent such as ethanol in a pressurized reaction vessel to give compound VII. The ketal in compound VII can be removed by acidic hydrolysis utilizing an acid such as $H_2SO_4$ or $CH_3SO_4$ either neat or utilizing a suitable organic solvent such $CH_2Cl_2$ at temperatures ranging from 0° C. to 80° C. to provide compounds of formula I.

Functional groups defined within X can be protected to prevent unwanted side reactions by using a suitable protecting group as long as it is stable to the conditions of subsequent reaction(s) and can be removed at the appropriate point without disrupting the remainder of the molecule. Further examples of protecting group chemistry are found in T. W. Greene and P. G. M. Wuts, "Protective Groups in Organic Synthesis".

The groups $R^4$, $R^{11}$, $R^{12}$, $R^{13}$, and $R^{14}$ can be further derivatized. For example, when $R^4$, $R^{11}$, $R^{12}$, $R^{13}$ or $R^{14}$ is an ester of a carboxylic acid or alcohol the compound can be transformed into the respective carboxylic acid or alcohol analog using standard conditions. The conditions to effect these transformations include aqueous base in which one or more molar equivalents of alkali metal hydroxide such as sodium hydroxide is used in water with a co-solvent such as THF, dioxane or a lower alcohol such as methanol or mixtures of THF and a lower alcohol at temperatures ranging from 0° C. to 40° C. Acidic conditions to effect the ester to acid conversion include using trifluoroacetic acid in a suitable solvent such as dichloromethane.

When $R^4$, $R^{11}$, $R^{12}$, $R^{13}$ or $R^{14}$ is a carboxylic acid or ester the compound can be reduced to the respective primary alcohol analog using standard conditions such as lithium aluminum hydride in ethyl ether. When $R^4$, $R^{11}$, $R^{12}$, $R^{13}$ or $R^{14}$ is an aldehyde or ketone the compound can be reduced to the respective alcohol analog using a metal catalyst, by sodium in alcohol, sodium borohydride and by lithium aluminum hydride.

When $R^4$, $R^{11}$, $R^{12}$, $R^{13}$ or $R^{14}$ is an ether, the compound can be transformed to the free alcohol by using one to ten molar equivalents of a strong Lewis acid such as a trihaloborane, most conveniently tribromoborane in a halocarbon solvent such as dichloromethane.

When $R^4$, $R^{11}$, $R^{12}$, $R^{13}$ or $R^{14}$ is an alcohol the compound can be oxidized to the respective aldehyde, carboxylic acid or ketone analog using a transition metal oxidant (chromium trioxide-pyridine, pyridinium chlorochromate, manganese dioxide) in an inert solvent such as ether, dichloromethane. Alcohols can also be oxidized using DMSO with a number of electrophilic molecules (dicyclohexylcarbodiimide, acetic anhydride, trifluoro acetic anhydride, oxalyl chloride and sulfur dioxide).

When $R^4$, $R^{11}$, $R^{12}$, $R^{13}$ or $R^{14}$ is a carboxylic acid the compound can be transformed into a carboxylic acid amide analog. This transformation can be accomplished using standard methods to effect carboxylic acid to carboxylic acid amide transformations.

These methods include converting the acid to an activated acid and reacting with one or more molar equivalents of the desired amine. Amines in this category include ammonia in the form of ammonium hydroxide, hydroxyl amine and 2-aminopropionitrile. Methods to activate the carboxylic acid include reacting said acid with one or more molar equivalents of oxalyl chloride or thionyl chloride to afford the carboxylic acid chloride in a suitable solvent such as dichloromethane, chloroform or diethyl ether. This reaction is often catalyzed by adding small amounts (0.01 to 0.1 molar equivalents) of dimethylformamide. Other methods to activate the carboxylic acid include reacting said acid with one or more molar equivalents of dicyclohexylcarbodiimide with or without one or more molar equivalents of hydroxybenzotriazole in a suitable solvent such as dichloromethane or dimethylformamide at temperatures ranging from 0° C. to 60° C.

When $R^4$, $R^{11}$, $R^{12}$, $R^{13}$ or $R^{14}$ is a carboxylic acid, the compound can be esterified utilizing an alkyl or aryl trichloroacetimidate with or without a catalyst such as $BF_3.Et_2O$ or methanesulfonic acid in a suitable solvent such as dichloromethane, ethyl acetate or cyclohexane.

When $R^4$, $R^{11}$, $R^{12}$, $R^{13}$ or $R^{14}$ is nitro, the compound can be reduced to the respective amino compound most readily using tin dichloride in ethyl acetate at 40° C. to 100° C. or with hydrazine and Montmorillinite clay in ethanol at 40 to 100° C. or by catalytic hydrogenation in the presence of a catalyst such as palladium on carbon.

When $R^4$, $R^{11}$, $R^{12}$, $R^{13}$ or $R^{14}$ is an amino or an alcohol, the compound can be acylated using one or more molar equivalents of suitable acylating agent. The acylating agent is generally a lower alkyl or aryl carboxylic acid anhydride or a lower alkyl or aryl carboxylic acid chloride. The reaction is run under standard conditions, for example the use of pyridine as solvent with or without a co-solvent such as dichloromethane at 0° C. to room temperature.

When $R^4$, $R^{11}$, $R^{12}$, $R^{13}$ or $R^{14}$ is an alcohol it can be acylated with a lower alkyl or aryl carboxylic acid anhydride in the presence of magnesium iodide in diethyl ether at ambient temperature of reflux.

When $R^4$, $R^{11}$, $R^{12}$, $R^{13}$ or $R^{14}$ is an alcohol, the compound can be alkylated under the conditions of the Mitsunobu Reaction (for a review see Oyo Mitsunobu Synthesis, 1981, 1-27).

When $R^4$, $R^{11}$, $R^{12}$, $R^{13}$ or $R^{14}$ is an alcohol can be alkylated with a suitable alkylating agent such as one or more molar equivalents of alkyl halide in the presence a base such as potassium carbonate or sodium hydroxide in a suitable solvent such as THF, DMF or DMSO at temperatures ranging from 0° C. to 60° C. The other co-reagents necessary to effect the Mitsunobu Reaction include one or more molar equivalents of a lower alkyl azodicarboxylate diester such as diethyl azodicarboxylate and one or more molar equivalents of triarylphosphine such as triphenylphosphine in a suitable solvent such as diethyl ether, THF, benzene or toluene at temperature ranging from −20° C. to 120° C.

When $R^4$, $R^{11}$, $R^{12}$, $R^{13}$ or $R^{14}$ is a nitrile it can be reduced to the aminoalkyl compound by tin (II) chloride in refluxing ethyl acetate or by catalytic hydrogenation in the presence of a catalyst such as Raney nickel or by lithium aluminum hydride in an inert solvent such as ether.

When $R^4$, $R^{11}$, $R^{12}$, $R^{13}$ or $R^{14}$ is a nitrile it can be converted to a carboxylic acid amide using standard conditions such as $HCl/H_2O$ at ambient temperatures to reflux or a milder procedure that involves the reaction of the nitrile with an alkaline solution of hydrogen peroxide.

Scheme 2

Preparation of compounds of formula II where $R^4$ is defined above and

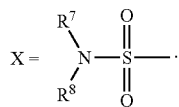

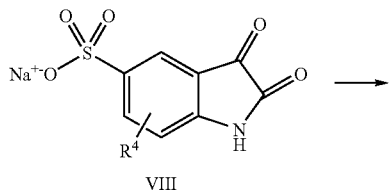

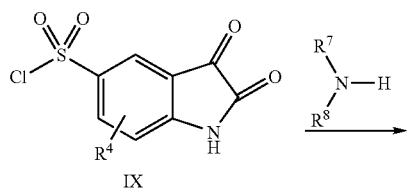

where X = 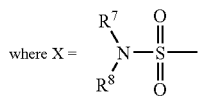

In Scheme 2, the sulfonic acid of compound VIII can be converted to the sulfonyl chloride of compound IX utilizing phosphorous oxychloride in a suitable organic solvent such as tetramethylene sulfone at 60° C. The starting sulfonic acids VIII can be obtained commercially or prepared by known procedures. Sulfonamides of formula II where $X=R^7R^8NS(O)_2$— and $R^7$ and $R^8$ are defined above can be obtained with sulfonyl chloride IX and $R^7R^8N$—H in the presence of a suitable base such as sodium hydride or pyridine in a solvent such as $CH_2Cl_2$ or THF. The amino groups defined by $R^7R^8N$—H are commercially available or can be easily prepared by known procedures. The compounds prepared in Scheme 2 of formula II ($X=R^7R^8NS(O)_2$—) can be utilized in Scheme 1 to prepare compounds of formula I where ($X=R^7R^8NS(O)_2$—) and $R^1$, $R^2$, $R^3$ and $R^4$ are defined above.

Scheme 3

Alternative preparation of compounds of formula I where $R^1$, $R^2$, $R^3$, $R^4$, $R^{15}$, $R^{16}$, and $R^{17}$ are defined above and

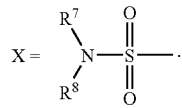

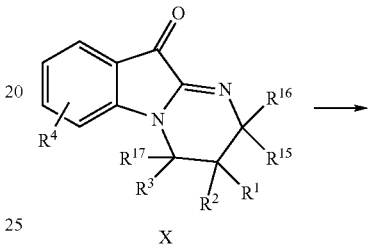

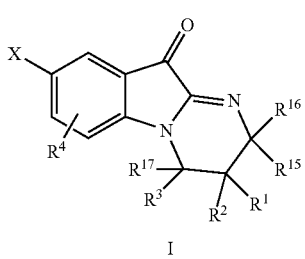

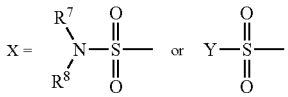

In Scheme 3, compounds of formula I where $X=R^7R^8NS(O)_2$— and $R^1$, $R^2$, $R^3$, $R^4$, $R^7$, $R^8$, $R^{15}$, $R^{16}$, and $R^{17}$ are defined above can be obtained by chlorosulfonylating X (prepared in Scheme 1) with chlorosulfonic acid neat to give sulfonyl chloride XI at temperatures ranging from 0° to 80° C. The sulfonamides of formula I where $X=R^7R^8NS(O)_2$— and $R^1$, $R^2$, $R^3$, $R^4$, $R^7$, $R^8$, $R^{15}$, $R^{16}$, and $R^{17}$ are defined above can be obtained by treating sulfonyl chloride XI with $R^7R^8N$—H in the presence of a suitable base such as sodium hydride or pyridine in a solvent such as $CH_2Cl_2$ or THF. The amino groups defined by $R^7R^8N$—H are commercially available or can be easily prepared by known procedures.

Scheme 4

Preparation of compounds of formula I where $R^1$, $R^2$, $R^3$, $R^4$, $R^{R15}$, $R^{16}$, and $R^{17}$ are defined above and

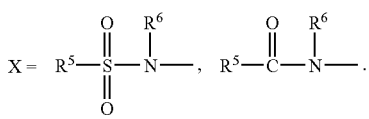

Scheme 4

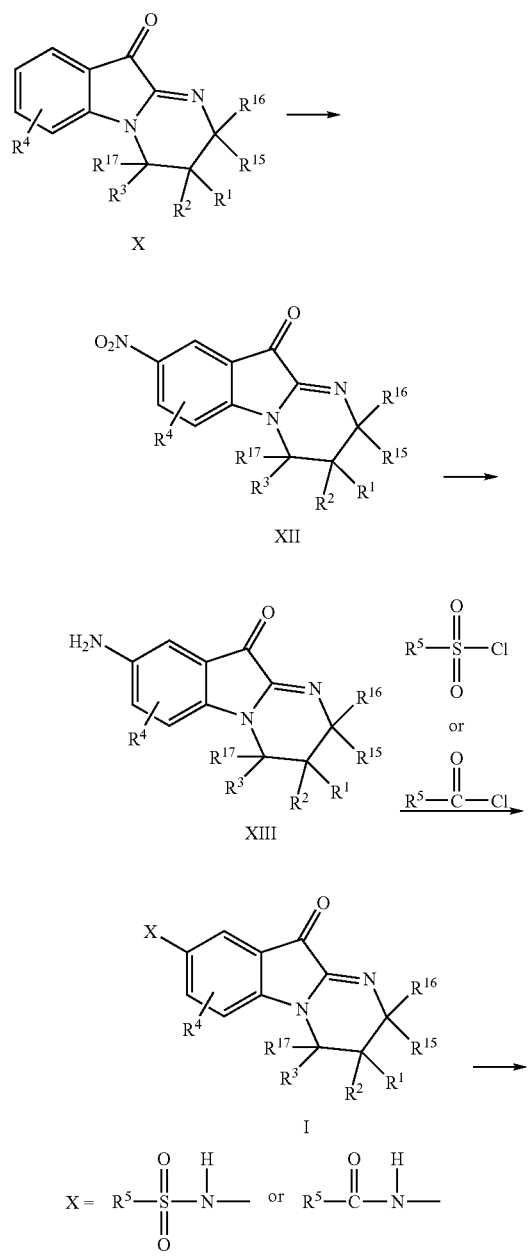

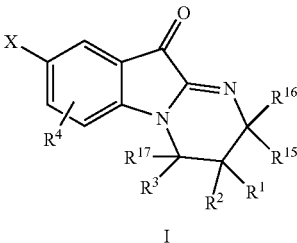

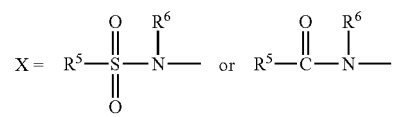

In Scheme 4, compounds of formula I where $X=R^5S(O)_2NR^6$— or $R^5C(O)NR^6$— and $R^1$, $R^2$, $R^3$, $R^4$, $R^5$, $R^6$, $R^{15}$, $R^{16}$, and $R^{17}$ are defined above can be obtained by nitration of compound X (prepared in Scheme 1) to give compound XII. Reduction of the nitro group in compound XII with tin (II) chloride dihydrate in a suitable solvent such as ethyl acetate at temperatures ranging room temperature to reflux provides the aniline of compound XIII. Compounds of formula I where $X=R^5S(O)_2NH$— or $R^5C(O)NH$— can be obtained by sulfonylation or acetylation with a sulfonyl chloride or acyl chloride respectively in the presence of a suitable base such as pyridine or triethylamine in an organic solvent such as dichloromethane or tetrahydrofuran at temperatures ranging from 0° C. to room temperature. The sulfonylating or acylating agent is commercially available or can be easily prepared by known procedures. The sulfonyl or acylating agent can be prepared by reaction of a sulfonic acid or a carboxylic acid with one or more equivalents of oxalyl chloride or thionyl chloride in a suitable solvent such as dichloromethane, chloroform or diethyl ether to afford the sulfonyl chloride or acid chloride. Compounds of formula I where $X=R^5S(O)_2NR^6$— or $R^5C(O)NR^6$— can be obtained by alkylation with an alkyl halide in the presence of a suitable base such as pryidine in an organic solvent such as THF or N,N-DMF at temperatures ranging from room temperature to reflux.

Scheme 5

Preparation of compounds of formula III where $R^4$, $R^7$, $R^8$, Y are defined above and

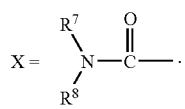

Scheme 5

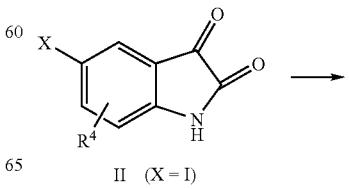

II (X = I)

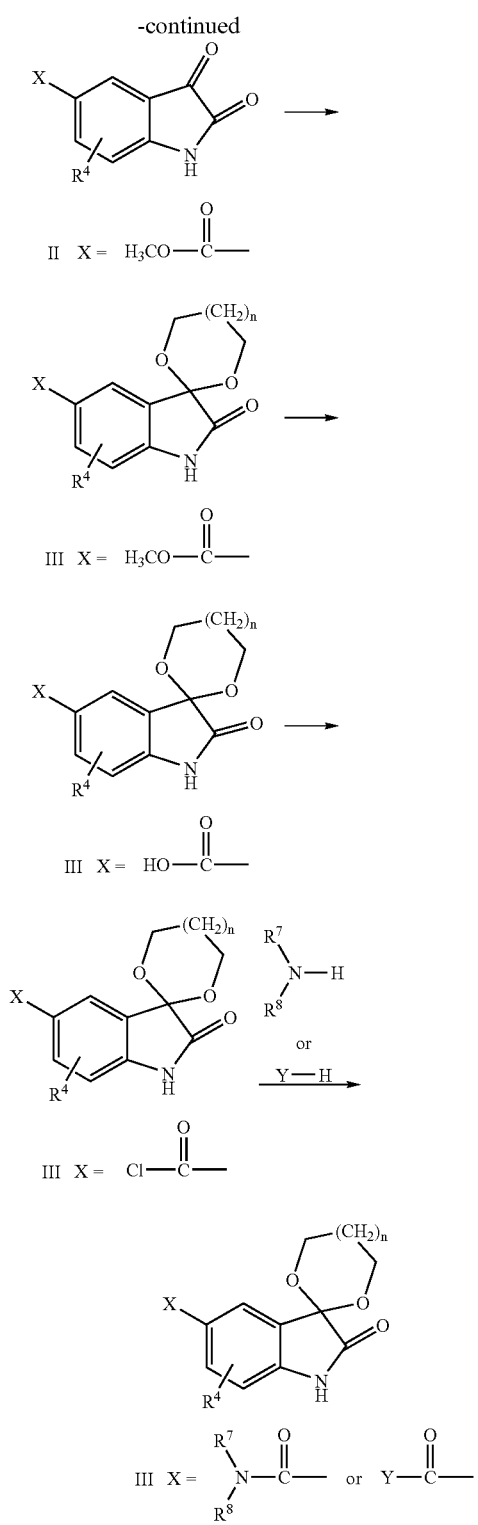

as described by Popp, F. D. *Advances in Heterocyclic Chemistry*, 1975, 18: 1-58 or as described by Sandmeyer, T. *Helvetica. Chim. Acta*, 1919, 2: 234-242. The iodoisatin of formula II can be converted to the methyl carboxylic acid ester of formula II $X=CH_3C(O)$— with the use of a suitable palladium catalyst such as dichlorobis(triphenylphosphine) palladium (II) in the presence of carbon monoxide, triethylamine and methanol in a suitable solvent such as N,N-dimethylformamide at 60° C. The ketone in formula II $X=CH_3C(O)$— can be protected to prevent unwanted side reactions by using a suitable protecting group such as an acyclic (dimethyl or diisopropyl) or cyclic (dioxolane, dioxane) ketal. In this scheme protection of the ketone is accomplished using a suitable protecting agent such as 1,3-propanediol in the presence of an acid such as $H_2SO_4$ or p-toluenesulfonic acid under refluxing conditions in benzene or toluene while azeotropically removing $H_2O$ with a Dean-Stark trap. The species of the ketone protecting group employed is not critical so long as the derivatized ketone is stable to the conditions of subsequent reaction(s) and can be removed at the appropriated point without disrupting the remainder of the molecule. Further examples of these groups are found in T. W. Greene and P. G. M. Wuts, "Protective Groups in Organic Synthesis," $2^{nd}$ ed. John Wiley and Sons, New York, N.Y., Chapter 4. Hydrolysis of the ester of formula III ($X=$—$CO_2CH_3$) to provide the carboxcylic acid of formula III ($X=$—$CO_2H$) can be accomplished with an aqueous solution of a suitable base such as sodium hydroxide or lithium hydroxide at temperatures ranging from 0° C. to reflux with or without a co-solvent such as tetrahydrofuran. The acyl chloride of formula III ($X=$—$C(O)Cl$) can be generated by treating the carboxylic acid of formula III ($X=$—$CO_2H$) with one or more equivalents of oxalyl chloride or thionyl chloride in a suitable solvent such as dichloromethane, chloroform or diethyl ether to afford the acid chloride. This reaction is often catalyzed by adding small amounts (0.01 to 0.1 molar equivalents) of dimethylformamide. The amide of formula III $X=R^7R^8NC(O)$—, where $R^4$, $R^7$, and $R^8$ are defined above can be obtained by treating the acid chloride of formula III ($X=$—$C(O)Cl$) with $R^7R^8N$—H in the presence of a suitable base such as sodium hydride or pyridine in a solvent such as $CH_2Cl_2$ or THF at temperatures ranging from 0° C. to 50° C. Other methods to prepare compounds of formula III where $R^4$, $R^7$, and $R^8$ are defined above and $X=R^7R^8NC(O)$—, include reacting the acid with one or more molar equivalents dicyclohexylcarbodiimide with or without one or more molar equivalents of hydroxybenzotriazole in a suitable solvent such as dichloromethane or dimethylformamide at temperatures ranging from 0° C. to 60° C. in the presence of $R^7R^8N$—H. The compounds of formula III where $R^4$, $R^7$, and $R^8$ are defined above and $X=R^7R^8NC(O)$—, can be utilized in Scheme 1 to prepare compounds of formula I where $X=R^7R^8NC(O)$—, and $R^1$, $R^2$, $R^3$ and $R^4$ are defined above.

Scheme 6

Preparation of compounds of formula II where $R^4$ and $R^5$ are defined above and

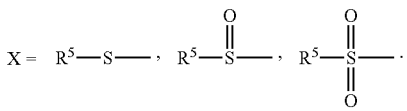

In Scheme 5, compounds of formula III where $R^4$, $R^7$, $R^8$, and n are defined above and $X=R^7R^8NC(O)$—, can be prepared from the 5-iodo isatin analog of formula II where $X=I$ and $R^4$ are defined above. The starting 5-iodoisatin can be either commercially available or can be prepared using standard synthetic methodology as described in Scheme 2 or

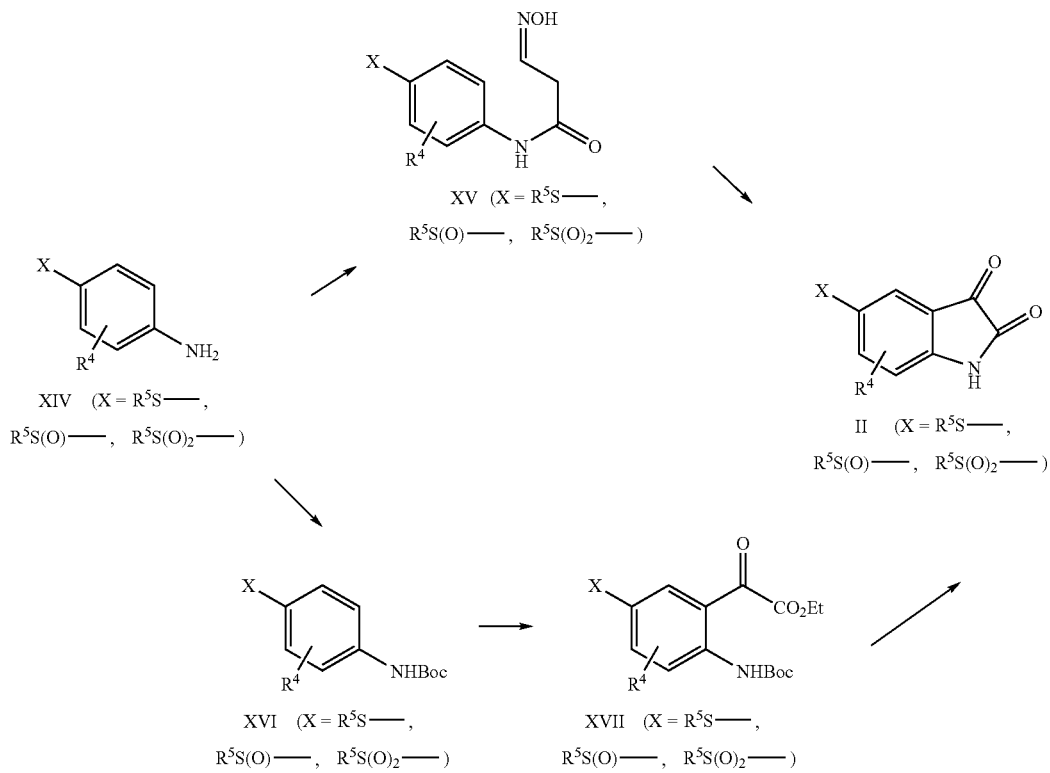

Scheme 6

Compounds of formula II where $R^4$ and $R^5$ are defined above and X=$R^5$S—, $R^5$S(O)—, $R^5$S(O)$_2$—, can be obtained from compound XIV were X=$R^5$S—, $R^5$S(O)—, $R^5$S(O)$_2$— via standard synthetic methodology as described by Sandmeyer, T. *Helvetica. Chim. Acta,* 1919, 2: 234-242. The desired substituted aniline is converted to the intermediate isonitrosoacetanilide of compound XV with hydroxylamine and chloral hydrate in an acidic aqueous solution at temperatures ranging from 50° C. to reflux. The starting anilines can either be obtained commercially or can be easily prepared by known procedures. The isonitrosoacetanilide of compound XV can be cyclized in either concentrated sulfuric acid or boron trifluoride etherate at temperatures ranging from 50° C. to 100° C. to give the isatin of formula II where $R^4$ and $R^5$ are defined above and X=$R^5$S—, $R^5$S(O)—, $R^5$S(O)$_2$—. Alternatively the aniline of compound XIV where X=$R^5$S—, $R^5$S(O)—, $R^5$S(O)$_2$— can be prepared by standard synthetic methodology as described by Hewawasam, P., *Tetrahedron Letters,* 1994, 35(40): 7303-7306. Herein the aniline is converted to the tert-butylcarbonate of compound XVI with di-tert-butyl dicarbonate in a suitable solvent such as THF at temperatures ranging from room temperature to reflux. The tert-butylcarbonate of compound XVI is ortho lithiated with tert-butyllithium at temperatures ranging from −20° C. to −78° C. in a suitable dry solvent such as THF or hexane. The lithiated species can be ortho acylated with diethyl oxalate to provide the intermediate of compound XVII. Treating XVII with hydrochloric acid in suitable solvent such as tetrahydrofuran, ethylene glycol dimethyl ether or ethanol at temperatures ranging form 70° C. to reflux in one step effects cyclization and deprotection of the tert-butylcarbonate group to provide the isatin of formula II where $R^4$ and $R^5$ are defined above and X=$R^5$S—, $R^5$S(O)—, $R^5$S(O)$_2$—. The isatins of formula II where $R^4$ and $R^5$ are defined above and X=$R^5$S(O)—, $R^5$S(O)$_2$— can be utilized in Scheme I to prepared compounds of formula I where X=$R^5$S—, $R^5$S(O)—, $R_5$S(O)$_2$ and $R^1$, $R^2$, $R^3$ and $R^4$ are defined above.

Compound of formula I where $R^{15}$ and $R^{16}$ are other than hydrogen, can be prepared as described in Scheme 7.

Scheme 7

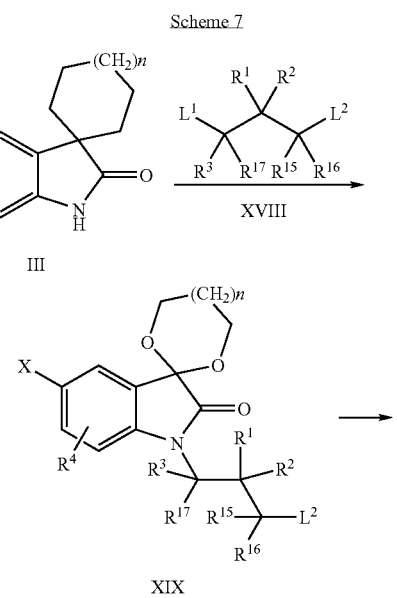

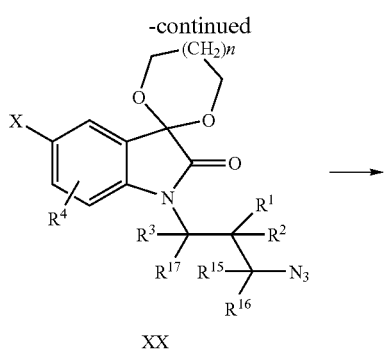

XX

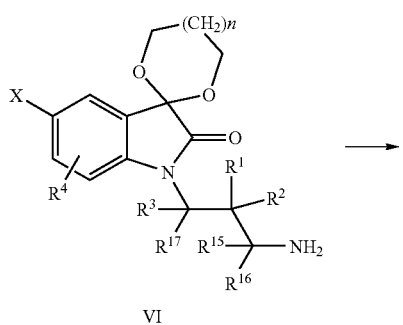

VI

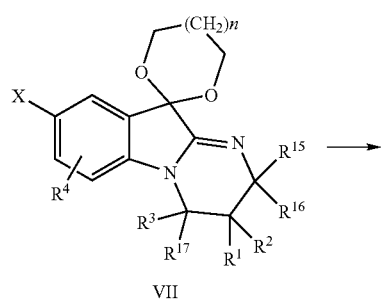

VII

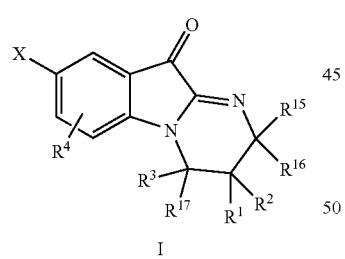

I

Pyrimidoindolones of formula I where $R^5$ and $R^{16}$ are other than hydrogen and n, X, $R^1$, $R^2$, $R^3$, $R^4$, $R^{15}$, $R^{16}$ and $R^{17}$ are defined above can be prepared from protected isatins of compound III where X and $R^4$ are defined as above. Alkylating the protected isatin III utilizing the desired alkylating reagent of compound XVIII where $R^1$, $R^2$, $R^3$, $R^{15}$, $R^{16}$ and $R^{17}$ are defined above is accomplished using a suitable base such as potassium t-butoxide in a nonprotic solvent such as DMSO at temperatures ranging from 0° C. to reflux. The substituents $L^1$ and $L^2$ are defined as a groups that can serve as leaving groups in the alkylation of compound III and in the subsequent reaction with sodium azide anion. Examples of suitable leaving groups include but are not restricted to bromide, chloride, iodide and suitable sulfonate esters such as tosylate, brosylate and mesylate. Compound XIX can be converted to the azide XX by treatment with sodium azide in a nonprotic solvent such as DMSO at temperatures ranging from 0° C. to reflux. Conversion of XX to the amine VI can be accomplished by catalytic hydrogenation using a suitable nickel or palladium catalyst in an organic solvent such as ethanol, methanol or THF containing ammonia to prevent dimerization. This amine can then be converted to compound I using the procedures described in Scheme 1.

Alternatively, compounds of formula I can also be prepared according to Scheme 8.

Scheme 8

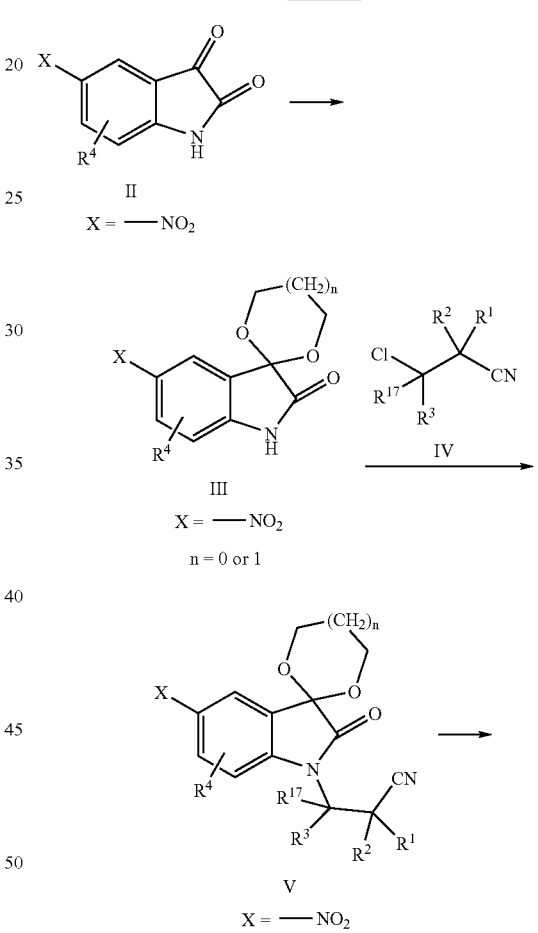

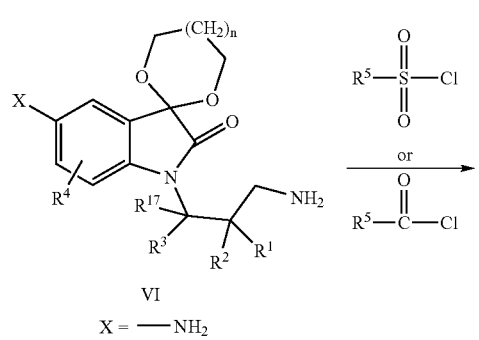

-continued

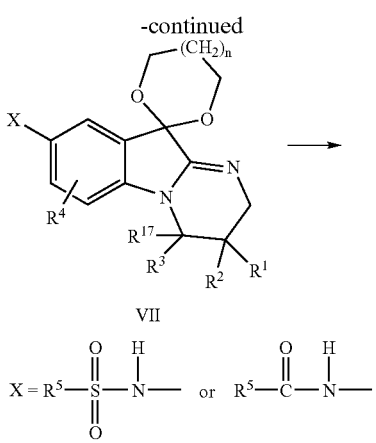

VII $$X = R^5-\overset{\overset{O}{\|}}{\underset{\overset{\|}{O}}{S}}-\overset{H}{\underset{|}{N}}- \quad \text{or} \quad R^5-\overset{\overset{O}{\|}}{C}-\overset{H}{\underset{|}{N}}-$$

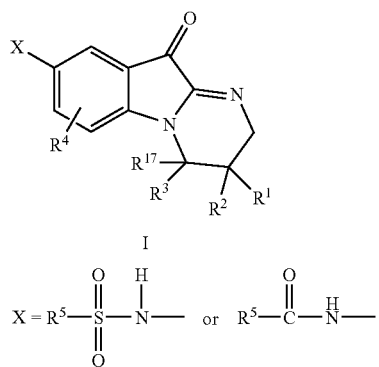

I $$X = R^5-\overset{\overset{O}{\|}}{\underset{\overset{\|}{O}}{S}}-\overset{H}{\underset{|}{N}}- \quad \text{or} \quad R^5-\overset{O}{\overset{\|}{C}}-\overset{H}{N}-$$

In Scheme 8, compounds of formula I where $X=R^5S(O)_2NH-$ or $R^5C(O)NH-$ and $R^1$, $R^2$, $R^3$, $R^4$, and $R^5$ are defined above can be obtained by a modification of Schemes 1 and 4. 5-Nitroisatin can be protected with a suitable protecting agent such as 1,3-propanediol or ethylene glycol in the presence of an acid such as $H_2SO_4$ or p-toluenesulfonic acid under refluxing conditions in benzene or toluene while azeotropically removing $H_2O$ with a Dean-Stark trap to give compound III. Alkylating the protected isatin III utilizing the desired alkylating reagent of compound IV where $R^1$, $R^2$, $R^3$, and $R^{17}$ are defined above is accomplished using a suitable base such as NaH or $K_2CO_3$ in a nonprotic solvent such as THF at temperatures ranging from 0° C. to reflux. The reduction of both the nitrile and nitro of V can be accomplished by catalytic hydrogenation using a suitable nickel or palladium catalyst in an organic solvent such as ethanol, methanol or THF containing ammonia to prevent dimerization to give compound VI. Compound VI can be subjected to cyclodehydration conditions by heating at 100° C. in a suitable solvent such as ethanol in a pressurized reaction vessel to give compound VII. Compounds of formula VII where $X=R^5S(O)_2NH-$ or $R^5C(O)NH-$ can be obtained by sulfonylation or acetylation with a sulfonyl chloride or acyl chloride respectively in the presence of a suitable base such as pyridine or triethylamine in an organic solvent such as dichloromethane or tetrahydrofuran at temperatures ranging from 0° C. to room temperature. The ketal in compound VII can be removed by acidic hydrolysis utilizing an acid such as $H_2SO_4$ or $CH_3SO_4$ either neat or utilizing a suitable organic solvent such CH$_2$Cl$_2$ at temperatures ranging from 0° C. to 80° C. to provide compounds of formula I.

The terms "effective amount", "therapeutically effective amount" and "effective dosage" as used herein, refer to the amount of a compound of formula I, that, when administered to a patient, is effective to at least partially ameliorate (and, in preferred embodiments, cure) a condition form which the patient is suspected to suffer. Such conditions include, but are not including inflammatory diseases (including, but not limited to arthritis, colitis, encephalitis, hepatitis, and pancreatitis) neurodegenerative disease (including, but not limited to Alzheimer's disease, Parkinson's disease traumatic brain injury, spinal cord injury, multiple sclerosis, and amyotrophic lateral sclerosis), ischemic injuries, including myocardial infarction and stroke, osteoarthritis-related diseases characterized by erosion of articular cartilage, and other related illnesses.

Compounds of formula I have been found to act as caspase inhibitors. They are therefore useful in the treatment of including inflammatory diseases (including, but not limited to arthritis, colitis, encephalitis, hepatitis, and pancreatitis), neurodegenerative disease (including, but not limited to Alzheimer's disease, Parkinson's disease, traumatic brain injury, spinal cord injury, multiple sclerosis, and amyotrophic lateral sclerosis) ischemic injuries, including myocardial infarction and stroke, osteoarthritis-related diseases characterized by erosion of articular cartilage, and other related illnesses. The present invention thus provides pharmaceutical compositions comprising at least one compound of formula I; and optionally one or more pharmaceutically acceptable carriers, excipients, or diluents.

Examples of such carriers are well known to those skilled in the art and are prepared in accordance with acceptable pharmaceutical procedures, such as, for example, those described in *Remington's Pharmaceutical Sciences,* 17th edition, ed. Alfonoso R. Gennaro, Mack Publishing Company, Easton, Pa. (1985), which is incorporated herein by reference in its entirety. Pharmaceutically acceptable carriers are those that are compatible with the other ingredients in the formulation and biologically acceptable.

The compounds of this invention may be administered orally or parenterally, neat or in combination with conventional pharmaceutical carriers. Applicable solid carriers can include one or more substances which may also act as flavoring agents, lubricants, solubilizers, suspending agents, fillers, glidants, compression aids, binders or tablet-disintegrating agents or encapsulating materials. They are formulated in conventional manner, for example, in a manner similar to that used for known antihypertensive agents, diuretics and β-blocking agents. Oral formulations containing the active compounds of this invention may comprise any conventionally used oral forms, including tablets, capsules, buccal forms, troches, lozenges and oral liquids, suspensions or solutions. In powders, the carrier is a finely divided solid, which is an admixture with the finely divided active ingredient. In tablets, the active ingredient is mixed with a carrier having the necessary compression properties in suitable proportions and compacted in the shape and size desired. The powders and tablets preferably contain up to 99% of the active ingredient.

Capsules may contain mixtures of the active compound(s) with inert fillers and/or diluents such as the pharmaceutically acceptable starches (e.g. corn, potato or tapioca starch), sugars, artificial sweetening agents, powdered celluloses, such as crystalline and microcrystalline celluloses, flours, gelatins, gums, etc.

Useful tablet formulations may be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes and ion exchange resins. Preferred surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colliodol silicon dioxide, phosphates, sodium dodecylsulfate, magnesium aluminum silicate, and triethanolamine. Oral formulations herein may utilize standard delay or time release formulations to alter the absorption of the active compound(s). The oral formulation may also consist of administering the active ingredient in water or fruit juice, containing appropriate solubilizers or emulisifiers as needed.

Liquid carriers may be used in preparing solutions, suspensions, emulsions, syrups and elixirs. The active ingredient of this invention can be dissolved or suspended in a pharmaceutically acceptable liquid carrier such as water, an organic solvent, a mixture of both or pharmaceutically acceptable oils or fat. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (particularly containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration the carrier can also be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellant.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration may be in either liquid or solid form.

Preferably the pharmaceutical composition is in unit dosage form, e.g. as tablets, capsules, powders, solutions, suspensions, emulsions, granules, or suppositories. In such form, the composition is sub-divided in unit dose containing appropriate quantities of the active ingredient; the unit dosage forms can be packaged compositions, for example, packeted powders, vials, ampoules, prefilled syringes or sachets containing liquids. The unit dosage form can be, for example, a capsule or tablet itself, or it can be the appropriate number of any such compositions in package form. Such unit dosage form may contain from about 1 mg/kg to about 250 mg/kg, preferably from 10 to 25 mg, and may be given in a single dose or in two or more divided doses. Such doses may be administered in any manner useful in directing the active compounds herein to the recipient's bloodstream, including orally, via implants, parenterally (including intravenous, intraperitoneal and subcutaneous injections), rectally, vaginally, and transdermally. Such administrations may be carried out using the present compounds, or pharmaceutically acceptable salts thereof, in lotions, creams, foams, patches, suspensions, solutions, and suppositories (rectal and vaginal).

When administered for the treatment or inhibition of a particular disease state or disorder, it is understood that the effective dosage may vary depending upon the particular compound utilized, the mode of administration, the condition, and severity thereof, of the condition being treated, as well as the various physical factors related to the individual being treated. In therapeutic application, compounds of the present invention are provided to a patient already suffering from a disease in an amount sufficient to cure or at least partially ameliorate the symptoms of the disease and its complications. An amount adequate to accomplish this is defined as a "therapeutically effective amount". The dosage to be used in the treatment of a specific case must be subjectively determined by the attending physician. The variables involved include the specific condition and the size, age and response pattern of the patient.

In some cases it may be desirable to administer the compounds directly to the airways in the form of an aerosol. For administration by intranasal or intrabrochial inhalation, the compounds of this invention may be formulated into an aqueous or partially aqueous solution.

The compounds of this invention may be administered parenterally or intraperitoneally. Solutions or suspensions of these active compounds as a free base or pharmaceutically acceptable salt may be prepared in water suitably mixed with a surfactant such as hydroxyl-propylcellulose. Dispersions may also be prepared in glycerol, liquid polyethylene glycols and mixtures thereof in oils. Under ordinary conditions of storage and use, these preparations contain a preservative to inhibit the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

The compounds of this invention can be administered transdermally through the use of a transdermal patch. For the purposes of this disclosure, transdermal administrations are understood to include all administrations across the surface of the body and the inner linings of bodily passages including epithelial and mucosal tissues. Such administrations may be carried out using the present compounds, or pharmaceutically acceptable salts thereof, in lotions, creams, foams, patches, suspensions, solutions, and suppositories (rectal and vaginal).

Transdermal administration may be accomplished through the use of a transdermal patch containing the active compound and a carrier that is inert to the active compound, is non-toxic to the skin, and allows delivery of the agent for systemic absorption into the blood stream via the skin. The carrier may take any number of forms such as creams and ointments, pastes, gels and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream, such as a semi-permeable membrane covering a reservoir containing the active ingredient with or without a carrier, or a matrix containing the active ingredient. Other occlusive devices are known in the literature.

The compounds of this invention may be administered rectally or vaginally in the form of a conventional suppository. Suppository formulations may be made from traditional materials, including cocoa butter, with or without the addition of waxes to alter the suppository's melting point, and glycerin. Water soluble suppository bases, such as polyethylene glycols of various molecular weights, may also be used.

In certain embodiments, the present invention is directed to prodrugs of compounds of formula I. Various forms of prodrugs are known in the art, for example, as discussed in, for example, Bundgaard, (ed.), Design of Prodrugs, Elsevier (1985); Widder, et al. (ed.), Methods in Enzymology, vol. 4, Academic Press (1985); Krogsgaard-Larsen, et al. (ed.), "Design and Application of Prodrugs", Textbook of Drug Design and Development, Chapter 5, 113-191 (1991), Bundgaard, et al., Journal of Drug Deliver reviews, 8:1-38 (1992), Bundgaard, J. of Pharmaceutical Sciences, 77:285 et seq. (1988); and Higuchi and Stella (eds.) Prodrugs as Novel Drug Delivery Systems, American Chemical Society (1975), each of which is incorporated by reference in its entirety.

It is understood that the dosage, regimen and mode of administration of these compounds will vary according to the malady and the individual being treated and will be subject to the judgment of the medical practitioner involved. It is preferred that the administration of one or more of the compounds herein begin at a low dose and be increased until the desired effects are achieved.

The present invention further provides a compound of the invention for use as an active therapeutic substance. Compounds of the invention are of particular use in the treatment of diseases including inflammatory diseases (including but not limited to, arthritis, colitis, encephalitis, hepatitis, and pancreatitis), neurodegenerative disease (including, but not limited to Alzheimer's disease, Parkinson's disease, traumatic brain injury, spinal cord injury, multiple sclerosis, and amyotrophic lateral sclerosis) ischemic injuries, including myocardial infarction and stroke, osteoarthritis-related diseases characterized by erosion of articular cartilage, and other related illnesses.

The present invention further provides a method for treating inflammatory diseases, (including, but not limited to arthritis, colitis, encephalitis, hepatitis, and pancreatitis), neurodegenerative disease (including, but not limited to Alzheimer's disease, Parkinson's disease, traumatic brain injury, spinal cord injury, multiple sclerosis, and amyotrophic lateral sclerosis) ischemic injuries, including myocardial infarction and stroke, osteoarthritis-related diseases characterized by erosion of articular cartilage, and other related illnesses, which comprises administering to the afflicted mammal an effective amount of a compound or pharmaceutical composition if the invention.

EXAMPLES

Example 1

8-{[(2S)-2-(Methoxymethyl)pyrrolidin-1-yl]sulfonyl}-3,4-dihydropyrimido[1,2-a]indol-10(2H)-one Step 1:
2,3-Dioxo-2,3-dihydro-1H-indole-5-sulfonylchloride

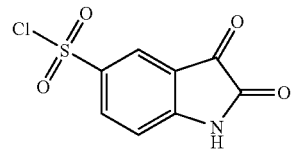

A mixture of isatinsulfonic acid sodium salt hydrate (10.00 g, 39.7 mmol ) and phosphorous oxychloride (18.5 mL, 199 mmol, 5 eq) in tetramethylene sulfone (50 mL) was heated at 60° C. for 3 hours under a dry $N_2$ atmosphere. The reaction was cooled in an ice bath to 0 C. and water was cautiously added drop-wise, keeping the internal temperature below 6° C. The resulting green solid was collected by filtration and was washed well with water. The solid was dissolved in ethyl acetate (200 mL) and washed again with water (3×50 mL), dried over magnesium sulfate, filtered and concentrated to give the crude product in 85% yield. The solid was recrystallized from ethyl acetate: hexanes with hot filtration to give the title compound (5.81 g, 66% yield). NMR (400 MHz, DMSO-$d_6$): consistent.

Step 2: 5-{[(2S)-2-(Methoxymethyl)pyrrolidin-1-yl]sulfonyl}-1H-indole-2,3-dione

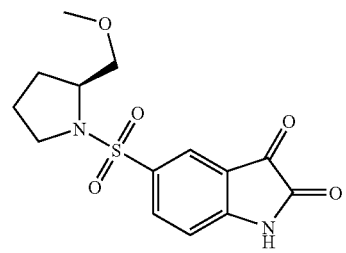

To a cold suspension of 2,3-dioxo-2,3-dihydro-1H-indole-5-sulfonylchloride (5.28 g, 21.5 mmol) in a 1:1 mixture of THF:CHCl$_3$ (254 mL) was added drop-wise via syringe pump a solution of (S)-(+)-2-(methoxymethyl)-pyrrolidine (3.45 mL, 28.0 mmol, 1.3 eq) (Aldrich) and N,N-diisopropylethylamine (7.49 mL, 43 mmol, 2 eq) in CHCl$_3$ (42 mL) over a period of 70 minutes under a dry $N_2$ atmosphere with cooling in an ice bath. After stirring an additional 20 minutes the mixture was concentrated. The residue was flash chromatographed (Biotage KP silica gel, 98/2 CH$_2$Cl$_2$/CH$_3$OH) to give the title compound as a dark greenish-yellow foam (6.48 g. 93% yield). NMR (400 MHz, DMSO-$d_6$): consistent MS: (API-ES$^-$) m/z 323 [M–H].

Step 3: 5'-{[(2S)-2-(Methoxymethyl)pyrrolidin-1-yl]sulfonyl}spiro[1,3-dioxane-2,3'-indol]-2'(1'H)-one

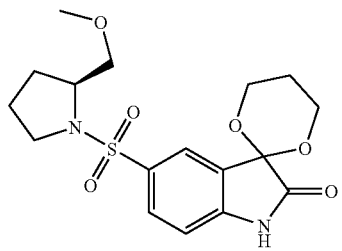

A mixture of 5-{[(2S)-2-(methoxymethyl)pyrrolidin-1-yl]sulfonyl}-1H-indole-2,3-dione (13.41 g, 41.3 mmol), 1,3 propanediol (12.1 mL, 165 mmol, 4eq) and p-tolune sulfonic acid (3.14 g, 16.5 mmol, 0.4 mole %) in benzene (800 mL) was heated to reflux under a Dean Stark Trap for 5 hours and stirred overnight at room temperature. The mixture was washed with saturated aqueous NaHCO$_3$ (3×300 mL), water (3×300 mL) and brine (3×300 mL), dried over sodium sulfate, filtered, and concentrated to give 10.7 g of crude product that was flash chromatographed (Biotage KP silica gel, step gradient 60/40-50/50 Pet Ether/EtOAc) to give the title compound as a white solid (7.1 g, 45% yield). Anal: Calc'd for C$_{17}$H$_{22}$N$_2$O$_6$S: C, 53.39; H, 5.80; N, 7.32; Found: C, 53.08; H,5.82; N, 6.92; NMR (400 MHz, DMSO-d$_6$): consistent. IR: consistent. MS: (ES$^-$) m/z 381 [M−H]. m.p: 127-128° C.

Step 4: 3-[5'-[(2S)-2-(Methoxymethyl)pyrrolidin-1-yl]sulfonyl}-2'-oxospiro[1,3-dioxane-2,3'-indol]-1' (2'H)-yl]propanenitrile

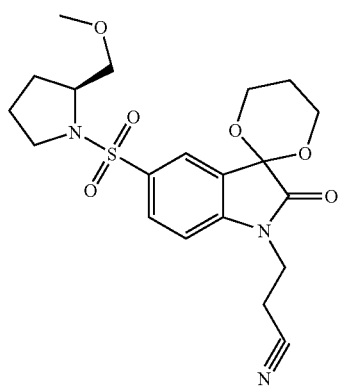

A suspension of 5'-{[(2S)-2-(methoxymethyl)pyrrolidin-1-yl]sulfonyl}spiro[1,3-dioxane-2,3'-indol]-2'(1'H)-one (6.8 g, 17.8 mmol) and benzyltrimethyl-ammonium hydroxide (40% by weight aqueous solution, 1.94 mL, 4.27 mmol, 0.25 eq) in absolute EtOH (80 mL) was heated to 59° C. and acryonitrile (2.93 mL, 44.5 mmol, 2.5 eq) was added dropwise. After heating 5 hrs at 72° C. the reaction was cooled to room temperature, poured into H$_2$O (160 mL) and extracted with EtOAc (3×150 mL). The combined organic extracts were washed with brine, dried over Na$_2$SO$_4$, filtered and concentrated. The residue was flash chromatographed (Biotage KP silica gel, 99/1 then 98/2 CH$_2$Cl$_2$/CH$_3$OH) to give the title compound as a white solid (4.5 g, 58% yield). Anal: Calc'd for C$_{20}$H$_{25}$N$_3$O$_6$S: C, 55.16; H, 5.79; N, 9.65; Found: C, 55.06, H, 5.94, N, 9.52; NMR (400 MHz, DMSO-d$_6$): consistent. MS: (ES$^+$) m/z 436[M+H] m.p.: 138-141° C.

Step 5: 8'-{[(2S)-2-(Methoxymethyl)pyrrolidinyl]sulfonyl}-3',4'-dihydrospiro(1,3-dioxane-2,10' (2'H)-pyrimido(1,2-a)indole)

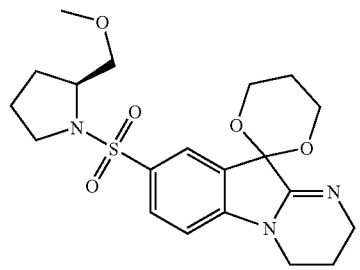

A mixture of 3-[5'-{[(2S)-2-(methoxymethyl)pyrrolidin-1-yl]sulfonyl}-2'-oxospiro[1,3-dioxane-2,3'-indol]-1' (2'H)-yl]propanenitrile (4.48 g, 10.3 mmol), and wet Raney nickel (4.1 g) in 2M EtOH.NH$_3$ (100 mL) and THF (100 mL) was hydrogenated in a Parr Hydrogenation Bottle (2L) at 45 lb/in$^2$ hydrogen for 24 hours. The Raney nickel was removed by filtration through Sulka Floc. The filtrate was poured into a steel pressure vessel and heated to 135° C. for 51 hours. The reaction was cooled and the solvents were removed. The residue was taken up in CH$_2$Cl$_2$ and combined with silica gel. The solvent was removed and the adsorbate was flash chromatographed (Biotage KP silica gel, and step gradient of CH$_2$Cl$_2$/CH$_3$OH/NH$_4$OH (98.5/1.0/0.5-98/01.5/0.5)) to give the title compound as a white solid (0.63 g, 14.5% yield). Anal: Calc'd. for C$_{20}$H$_{27}$N$_3$O$_5$S: C, 56.99; H, 6.46; N, 9.97; Found: C, 56.80, H, 6.45, N, 9.87; NMR (400 MHz, DMSO-d$_6$): consistent. MS: (ES$^+$) m/z 422 [M+H]. Opt. Rotation: 94.1(calculated) at 25° C. in CH$_3$OH (1% concentration), wavelength 589; m.p. 129-130°.

Step 6: 8-{[(2S)-2-(Methoxymethyl)pyrrolidin-1-yl]sulfonyl}-3,4-dihydropyrimido[1,2-a]indol-10(2H)-one

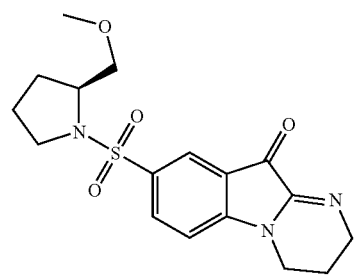

8'-{[(2S)-2-(Methoxymethyl)pyrrolidinyl]sulfonyl}-3',4'-dihydrospiro(1,3-dioxane-2,10'   (2'H)-pyrimido(1,2-a)indole) (1.30 g, 3.32 mmol) was added portion-wise to concentrated H₂SO₄ (13 mL) over a period of 15 minutes with cooling in an ice bath. The mixture was allowed to warm to room temperature, stirred for 1.25 hours, poured into ice and basified to pH 10.5 by the careful addition of concentrated NH₄OH maintaining internal ice with an external ice bath. The resulting bright yellow-orange solid was filtered, dried, and dissolved in CH₂Cl₂. After stirring for 1 hour the solution was filtered and the solid was dried in vacuo at 52° C. to give the title compound as a bright yellow solid (0.95 g, 79% yield). Anal: Calc'd. for $C_{17}H_{21}N_3O_4S$ : C, 56.18; H, 5.82; N, 11.56; Found: C, 56.38; H, 5.90; N, 11.43. NMR: consistent. MS: (ES⁻) m/z 362 [M–H]. IR: consistent. m.p.: 171-172° C. Opt. Rotation: –109.70 (calculated) at 25° C. in CHCl₃ (1%concentration), wavelength 589.

Example 2

8-{[(2S)-2-(Methoxymethyl)pyrrolidin-1-yl]sulfonyl}-3,3-dimethyl-3,4-dihydropyrimido[1,2-a]indol-10(2H)-one Step 1: 3-[5'-{[(2S)-2-(Methoxymethyl)pyrrolidin-1-yl]sulfonyl}-2'-oxospiro[1,3-dioxane-2,3'-indol]-1'1' (2'H)-yl]-2,2-dimethylpropanenitrile

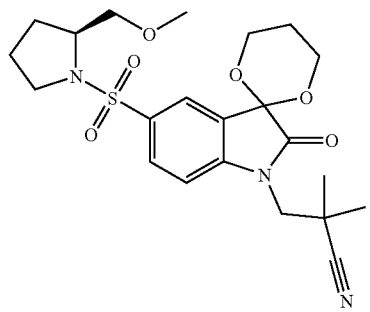

To a stirred solution of potassium t-butoxide (0.316 g, 3.22 mmol, 1.2 eq) in anhydrous DMSO (7.5 mL) was added 5'-{[(2S)-2-(methoxymethyl)pyrrolidin-1-yl]sulfonyl}spiro[1,3-dioxane-2,3'-indol]-2'(1'H)-one (1.03 g, 2.68 mmol) at room temperature under a dry N₂ atmosphere. After stirring 15 minutes, 3-chloro-2,2-dimethylpropionitrile (0.945 g, 8.04 mmol, 3 eq) (*Syn. Comm.* 20(12) 1757, 1990) was added. The reaction was heated at 130° C. for 20 hours then cooled to room temperature and additional potassium t-butoxide (0.036 g, 0.12 eq) was added. The reaction was heated an additional 24 hours, cooled to room temperature, and poured into H₂O (100 mL) and extracted with Et₂O (4×). The combined organic extracts were dried over Na₂SO₄, filtered and concentrated. The crude product was flash chromatographed (Biotage KP silica gel, and 100% CH₂Cl₂ then CH₂Cl₂/MeOH/NH₄OH (97.75/1.5/0.75)) to give the title compound as a yellow oil (1.27 g, 100% yield). The compound was used without further purification. NMR (400 MHz, D₆DMSO): consistent.

Step 2: 8'-{[(2S)-2-(Methoxymethyl)pyrrolidin-1-yl]sulfonyl}-3',3'-dimethyl-3',4'-dihydro-2'H-spiro[1,3-dioxane-2,10'-pyrimido[1,2-a]indole

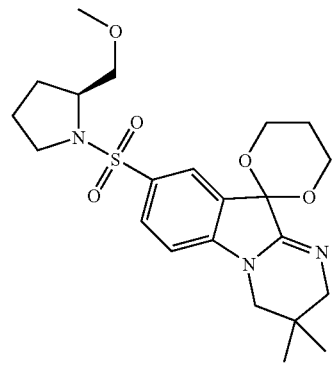

3-[5'-{[(2S)-2-(Methoxymethyl)pyrrolidin-1-yl]sulfonyl}-2'-oxospiro[1,3-dioxane-2,3'-indol]-1' (2'H)-yl]-2,2-dimethylpropanenitrile (1.92 g, 4.14 mmol), wet Raney Nickel (3.59 g), 2M EtOH.NH₃ (175 mL) were combined in a Parr Bottle (500 mL) and hydrogenated at 52 lb/in² H₂ for 18 hours. The Raney Nickel was removed by filtration through Sulka Floc and the filter pad was washed well with 2M EtOH.NH₃. The filtrate was poured into a steel pressure vessel and heated at 135° C. for 21 hours. The mixture was cooled to room temperature and the solvents were removed. The crude product was purified on Biotage KP silica gel eluting with CH₂Cl₂/CH₃OH/NH₄OH (95.5/3/1.5) to give the title compound as a white solid (1.68 g, 90% yield). Anal: Calc'd. for $C_{22}H_{31}N_3O_5S$ : C, 58.78; H, 6.95; N, 9.35; Found: C, 58.50; H, 7.02; N, 9.22. NMR: consistent. MS; (ES⁺) m/z 450 [M+H]. IR: consistent. m.p.: 167-169° C. Opt. Rotation: –80.62(calculated) at 25° C. in CH₂Cl₂ (1% concentration), wavelength 589.

Step 3: 8-{[(2S)-2-(Methoxymethyl)pyrrolidin-1-yl]sulfonyl}-3,3-dimethyl-3,4-dihydropyrimido[1,2-a]indol-10(2H)-one

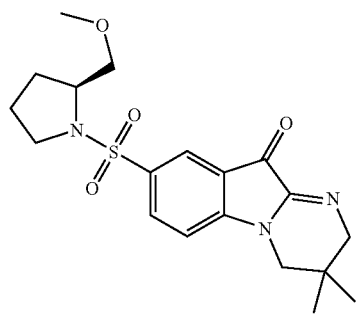

8'-{[(2S)-2-(Methoxymethyl)pyrrolidin-1-yl]sulfonyl}-3',3'-dimethyl-3',4'-dihydro-2'H-spiro[1,3-dioxane-2,10'-pyrimido[1,2-a]indole](1.12 g, 2.49 mmol) was added portion-wise to concentrated H₂SO₄ (10 mL) over a period of 0.5 hours with cooling in an ice bath. The mixture was stirred at room temperature for 1 hr then added to ice and basified to pH 10.7 by the drop-wise addition of concentrated NH₄OH all the while keeping the temperature below 5° C. The resulting yellow solid was filtered, dissolved in CH₂Cl₂, dried over Na₂SO₄ and concentrated in vacuo to give the title compound as a gold colored solid (0.902 g, 92.5% yield). NMR (400 MHz, D₆DMSO): consistent; Anal: Calc'd. for Cl₉H₂₅N₃O₄S: C, 58.29; H, 6.44; N, 10.73. Found: C, 58.14; H, 6.35; N, 10.69; NMR (400 MHz, DMSO-d₆): consistent. Opt. Rotation: −80.0 (calculated) at 25° C. in CH₂Cl₂ (1% concentration), wavelength 589. IR: consistent. MS: (ES⁻) m/z 390 [M+H]. m.p.: 163-165°.

Example 3

8-{[(2S)-2-(Phenoxymethyl)pyrrolidin-1-yl]sulfonyl}-3,4-dihydropyrimido[1,2-a]indol-10(2H)-one]

Step 1: 5-{[(2S)-2-(Phenoxymethyl)pyrrolidin-1-yl]sulfonyl}-1H-indole-2,3-dione

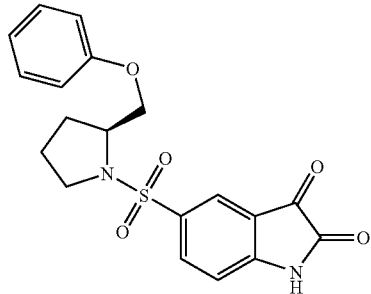

To a cold solution of 2,3-dioxo-2,3-dihydro-1-H-indole-5-sulfonylchloride (3.80 g, 15.5 mmol) in a 1:1 mixture of THF:CHCl₃ (194 mL) was added drop-wise via syringe pump a solution of (2S)-2-(phenoxymethyl)pyrrolidine (2.85 g, 16.1 mmol, 1.03 eq) (*J. Med. Chem*, 44, 2014, 2001) and N,N-diisopropylethylamine (5.61 mL, 32.2 mmol, 2 eq) in CHCl₃ (30 mL) over a period of 50 minutes under a dry N₂ atmosphere with cooling in an ice bath. After stirring at room temperature for 64 hr the reaction mixture was concentrated and the crude product was flash chromatographed twice using Biotage KP silica gel, and gradient of 98/2 CH₂Cl₂/CH₃OH as eluent on the first column and 90/10 CH₂Cl₂/CH₃OH as eluent on the second column to give the title compound as a dark green solid (5.29 g, 88% yield). NMR (400 MHz, DMSO-d₆): consistent. MS: (ES⁻) m/z 385 [M−H]. MS: (ES⁺) m/z 387 [M+H].

Step 2: 5'-{[(2S)-2-(Phenoxymethyl)pyrrolidin-1-yl]sulfonyl}spiro[1,3-dioxane-2,3'-indol]-2' (1'H)-one

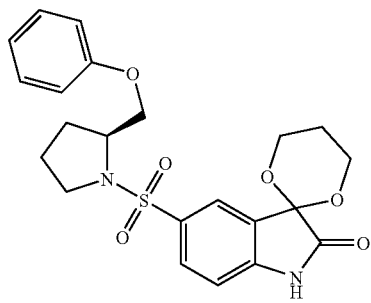

To a rapidly and efficiently stirred suspension of 5-{[(2S)-2-(phenoxymethyl)pyrrolidin-1-yl]sulfonyl}-1H-indole-2,3-dione (16.13 g, 41.7 mmol) in benzene (785 mL) was added p-toluenesulfonic acid mono-hydrate (1.58 g, 8.34 mmol, 0.2 mole %) and 1,3 propanediol (12.2 mL, 167 mmol, 4 eq) and the mixture was heated to reflux under a Dean Stark Trap for 5 hr. Additional p-toluenesulfonic acid (1.50 g, 0.2 mole %) was added and the mixture was heated for another 1.5 hr. After cooling in an ice bath, the black reaction mixture was washed with sat. aq. NaHCO₃ (3×350 mL), water (2×500 mL), brine (3×500 mL), dried over Na₂SO₄, filtered and concentrated. The crude product was purified on silica gel eluting with CH₂Cl₂ followed by 50/50 Pet ether/EtOAc to give the title compound as an orange solid (11.44 g, 61.7% yield). NMR (400 MHz, DMSO-d₆): consistent. MS: (ES⁻) m/z 443 [M−H]. MS: (ES⁺) m/z 445 [M+H].

Step 3: 3-{2'-Oxospiro[1,3-dioxane-1,3'-[3H]indol]-5'-(1-[(2S)-phenoxymethyl]-pyrrolidinylsulfonyl)}propanenitrile

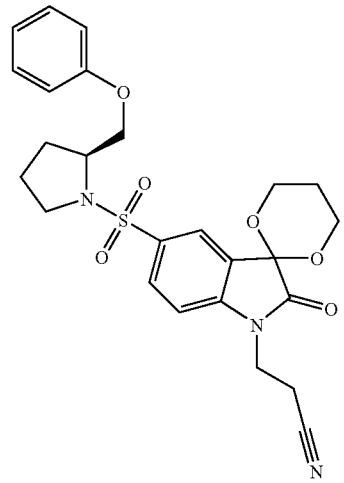

A mixture of 5'-{[(2S)-2-(phenoxymethyl)pyrrolidin-1-yl]sulfonyl}spiro[1,3-dioxane-2,3'-indol]-2'(1'H)-one (2.56 g, 5.76 mmol), and benzyltrimethylammonuim hydroxide (40% aqueous solution, 0.57 mL, 1.44 mmol, 0.25 mole %) in abs. EtOH (26 mL) was heated to 60° C. and acrylonirile (0.948 mL, 14.4 mmol, 2.5 eq) was added slowly by syringe. The reaction was heated to reflux for 4.5 hr and stirred at room temperature for 12 hours. The crude solid product was filtered, washed with abs. EtOH and flash chromatographed (Biotage KP silica gel and 70/30 -60/40 Pet ether/EtOAc) to give the title compound as an off white solid. NMR (300 MHz, DMSO-d₆): consistent. MS: (ESI+) m/z 498 [M+H].

Step 4: 1'-(3-Aminopropyl)-5'-{[(2S)-2-(phenoxymethyl)pyrrolidin-1yl]sulfonyl}spiro[1,3-dioxane-2,3'-indol]-2'(1H)-one

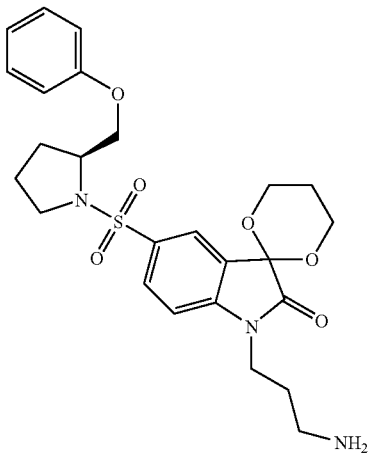

A mixture of 3-{2'-oxospiro[1,3-dioxane-1,3'-[3H]indol]-5'-(1-[(2S)-phenoxymethyl]-pyrrolidinylsulfonyl)}propanenitrile (1.00 g, 2.01 mmol), wet Raney Nickel (1.14 g) in 2M EtOH.NH$_3$ (27 mL), and THF (27 mL) was hydrogenated in a Parr Hydrogenation Bottle at 53 lb/in$^2$ H$_2$ for 18 hours. The Raney Nickel was removed by filtration through Sulka Floc. The filtrate was concentrated and the crude product purified on Biotage KP silica gel eluting with CH$_2$Cl$_2$/CH$_3$OH/NH$_4$OH (95.5/3/1.5) to give the intermediate amine (1.12 g, 89% yield) as a white oil. NMR (300 MHz, D$_6$DMSO): consistent. MS: (ES$^+$) m/z 503 [M+H].

Step 5: 8'-{[(2S)-2-(Phenoxymethyl)pyrrolidin-1-yl]sulfonyl}-3',4'-dihydro-2'H-spiro[1,3-dioxane-2,10'-pyrimido[1,2-a]indole]

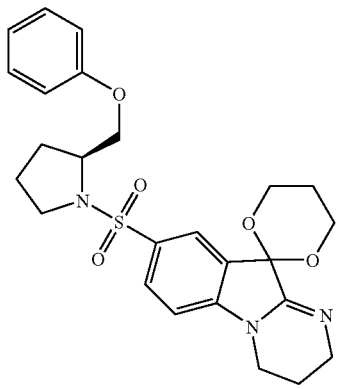

1'-(3-Aminopropyl)-5'-{[(2S)-2-(phenoxymethyl)pyrrolidin-1-yl]sulfonyl}spiro[1,3-dioxane-2,3'-indol]-2'(1'H)-one (0.98 g, 1.95 mmol) was taken up in 2M EtOH.NH$_3$ (100 mL) poured into a steel pressure bottle and heated at 135° C. for 20.5 hr. The mixture was cooled to room temperature and concentrated. The residue was washed with H$_2$O (3×), brine (2×), dried over MgSO$_4$, and filtered. The filtrate was flash chromatographed (Biotage KP silica gel, CH$_2$Cl$_2$/CH$_3$OH/NH$_4$OH (98.5/1.0/0.5)) to give the title compound as a white solid (0.73 g, 77% yield). NMR (400 MHz, DMSO-d$_6$): consistent. MS: (APCI+) m/z 483 [M+H]. Opt. Rotation: −169.0 (calculated) at 25° C. in CHCl$_3$ (1% concentration) at 589 nM.

Step 6: 8-{[(2S)-2-(Phenoxymethyl)pyrrolidin-1-yl]sulfonyl}-3,4-dihydropyrimido[1,2-a]indol-10(2H)-one]

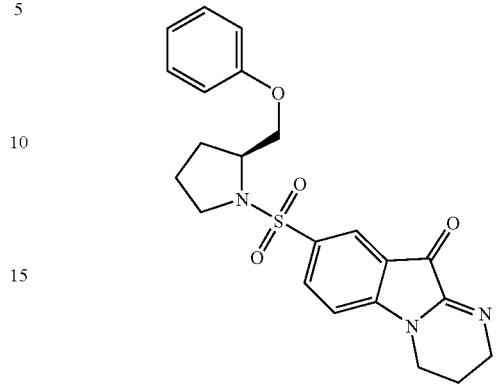

To cold concentrated HCl (8.5 mL) was added a solution of 8'-{[(2S)-2-(phenoxymethyl)pyrrolidin-1-yl]sulfonyl}-3',4'-dihydro-2'H-spiro[1,3-dioxane-2,10'-pyrimido[1,2-a]indole] (0.430 g, 0.889 mmol) in 1,4 dioxane (2 mL) dropwise over a period of 20 minutes with cooling in an ice bath. The mixture was stirred at room temperature (16 hours) then heated at 53° C. (36 hours). The mixture was cooled in an ice bath, poured into ice, and basified with concentrated NH$_4$OH to pH 11 keeping the temperature below 5° C. The organics were extracted with EtOAc (2×). The combined organic extracts were dried over MgSO$_4$, filtered and concentrated. The crude product was flash chromatographed on Biotage KP silica gel eluting with 95/5 (EtOAc/CH$_3$OH) to give the title compound which was dried in vacuo at 61° C. to give the analytically pure sample as an orange-brown solid (0.074 g, 19.5% yield). Anal. Calc'd for C$_{22}$H$_{23}$N$_3$O$_4$S: C, 62.10; H, 5.45; N, 9.88. Found: C, 61.89; H, 5.50; N, 9.65. NMR (400 MHz, DMSO-d$_6$): consistent. MS: (ES+) m/z 426 [M+H]. MS: (ES−) m/z 424 [M−H]. m.p.: 159–160° C.

Example 4

3,3-Dimethyl-8-{[(2S)-2-(phenoxymethyl)pyrrolidin-1-yl]sulfonyl}-3,4-dihydropyrimido[1,2-a]indol-10(2H)-one

Step 1: 2,2-Dimethyl-3-[2'-oxo-5'-{[(2S)-2-(phenoxymethyl)pyrrolidin-1-yl]sulfonyl}spiro[1,3-dioxane-2,3'-indol]-1'(2'H)-yl]propanenitrile

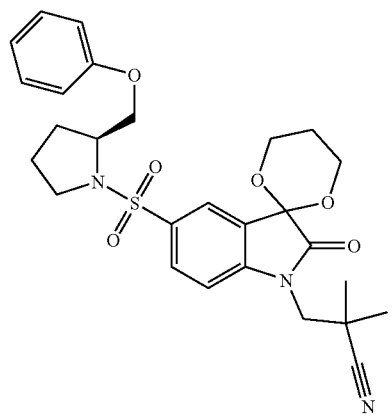

At room temperature, to a solution of potassium t-butoxide (3.45 g, 30.8 mmol, 1.2 eq) in anhyd., DMSO (70 mL) was added 5'-{[(2S)-2-(phenoxymethyl)pyrrolidin-1-yl]sulfonyl}spiro[1,3-dioxane-2,3'-indol]-2'(1'H)-one (11.39 g, 25.6 mmol) all at one time under a dry $N_2$ atmosphere. After stirring 10 minutes, to the reaction was added dropwise 3-chloro,2,2-dimethylpropionitrile (9.03 g, 76.8 mmol, 3 eq) over a 5 minute period. After stirring 1.25 hours to the reaction was added additional potassium t-butoxide (0.345 g, 3.08 mmol) and the reaction was heated to 132° C. for 29 hours. The mixture was cooled to room temperature, poured into $H_2O$ (1 L) and exhaustively extracted with $Et_2O$. The combined organic extracts were dried over $Na_2SO_4$, filtered and concentrated. The crude product was purified on silica gel using a step gradient of $CH_2Cl_2$, followed by $CH_2Cl_2$/ $CH_3OH/NH_4OH$ (98.5/1/0.5 then 97/2/1)) to give the title compound as a tan solid (11.4 g, 84.3% yield). NMR (400 MHz, DMSO-$d_6$): consistent. MS: (API-ES+) m/z 526 [M+H].

Step 2: 3',3'-Dimethyl-8'-{[(2S)-2-(phenoxymethyl) pyrrolidin-1-yl]sulfonyl}-3',4'-dihydro-2'H-spiro[1, 3-dioxane-2,10'-pyrimido[1,2-a]indole

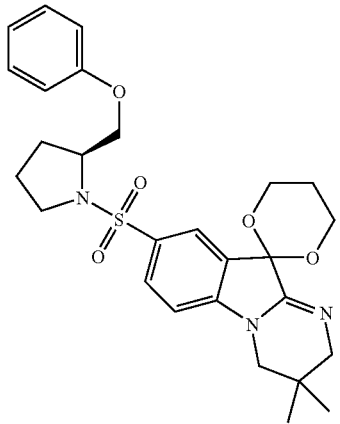

A mixture of 2,2-dimethyl-3-[2'-oxo-5'-{[(2S)-2-(phenoxymethyl)pyrrolidin-1-yl]sulfonyl}spiro[1,3-dioxane-2, 3'-indol]-1'(2'H)-yl]propanenitrile (3.48 g, 6.63 mmol), and wet Raney Nickel (3.58 g), in 2M EtOH.NH$_3$ (85 mL), and THF (85 mL) was hydrogenated in a Parr Hydrogenation Bottle (500 mL) at 56 lb/in$^2$ $H_2$ for 16.5 hours. The Raney nickel was removed by filtration through Sulka Floc. The filtrate was poured into a steel pressure bottle and heated to 135° C. for 22 hr. The reaction was cooled to room temperature and concentrated. The crude product was combined with previous runs (10.88 g total) and purified on silica gel eluting with a step gradient of $CH_2Cl_2/CH_3OH/NH_4OH$ (99.25/0.50/0.25) then (98.5/1.0/0.5) to give the title compound as a tan solid. The product was triturated with petroleum ether and dried in vacuo to give the title compound as an off white solid (2.6 g, 62% yield).

Anal: Calcd for $C_{27}H_{33}N_3O_5S$: C, 63.38; H, 6.5; N, 8.21. Found: C, 63.49; H, 6.65; N, 7.84. NMR (400 MHz, DMSO-$d_6$): consistent. IR consistent. MS: (ES$^+$) m/z 512 [M+H]. m.p.: 78° C. dec.

Step 3: 3,3-Dimethyl-8-{[(2S)-2-(phenoxymethyl) pyrrolidin-1-yl]sulfonyl}-3,4-dihydropyrimido[1,2-a]indol-10(2H)-one

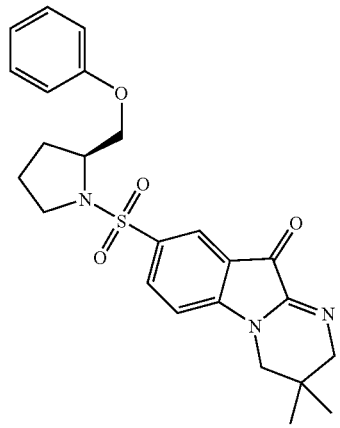

3',3'-Dimethyl-8'-{[(2S)-2-(phenoxymethyl)pyrrolidin-1-yl]sulfonyl}-3,',4'-dihydro-2'H-spiro[1,3-dioxane-2,10'-pyrimido[1,2-a]indole (1.00 g, 1.95 mmol) was added slowly to methane sulfonic acid (50 mL) with cooling in an ice bath. The ice bath was removed and the mixture was stirred at room temperature for 30 min. The reaction was heated at 54° C. for one hour. After cooling in an ice bath the reaction mixture was poured slowly onto ice with efficient stirring and basified with conc. NH$_4$H to pH 11 keeping the temperature below 5° C. The reaction was extracted with EtOAc (3×). The combined organic extracts were dried over Na$_2$SO$_4$, filtered and concentrated. The crude product was purified on Biotage KP silica gel eluting with 83/17 CH$_2$Cl$_2$/ EtOAc to give the title compound as a bright yellow film on glass (0.53 g, 59% yield). The product was combined with the products from previous runs, dissolved in a minimum amount of acetone, and added drop-wise to pet ether with stirring. The product was collected by filtration and dried in vauco to give the analytically pure sample as a bright yellow solid (0.478 g, 54% yield). Anal: Calcd for C$_{24}$H$_{27}$N$_3$O$_4$S: C, 63.56; H, 6.00; N, 9.26. Found: C, 63.41; H, 5.92; N, 8.84. NMR (400 MHz, DMSO-$d_6$): consistent. MS: (ES–) m/z 452 [M–H]. m.p.: 73-88° C. dec; Opt. Rotation: –182.02 (calculated) at 25° C. in CH$_2$Cl$_2$ (1% concentration) at 589 nM.

Example 5

7-Chloro-8-{[(2S)-2-(methoxymethyl)pyrrolidin-1-yl-]sulfonyl}-3,4-dihydropyrimido[1,2-a]indol-10 (2H)-one Step 1:
3,3-Dibromo-6-chloro-1,3-dihydro-indol-2-one

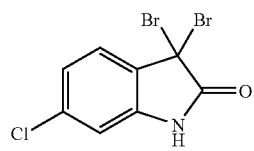

At room temperature, to a solution of 6-chlorooxindole (10.0 g, 59.7 mmol ) in t-BuOH (500 mL) and water (2.6 mL) was added pyridinium tribromide (57.25 g, 79 mmol, 3 eq) and the reaction was stirred for 3.5 hr. The reaction was diluted with water (500 mL) and extracted with EtOAc (3×). The combined organic extracts were washed with sat. aq. NaHCO$_3$ (3×), dried over MgSO$_4$, filtered and concentrated to give the title compound as a tan solid (19.66 g, 100% yield). NMR (400 MHz, DMSO-d$_6$): consistent. MS: (API-ES$^+$) m/z 325 [M+H].

Step 2: 6-Chloroisatin

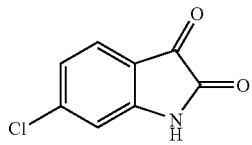

3,3-Dibromo-6-chloro-1,3-dihydro-indol-2-one (21.34 g, 59.7 mmol) was suspended in a 4:1 (v:v) mixture of MeOH (172 mL): water (43 mL) and heated at reflux for 19 hr. The reaction was cooled in an ice bath and filtered. The red solid was washed once with cold CH$_3$OH and dried to give the title compound as a red solid (10.49 g, 88% yield). NMR (400 MHz, DMSO-d$_6$): consistent. MS: (API-ES+) m/z 182/184 [M+H], 1 chlorine pattern observed.

Step 3: 6'-Chlorospiro[1,3-dioxane-2,3'-indol]-2'(1'H)-one

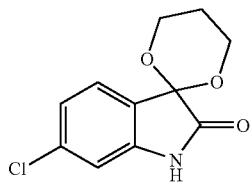

A mixture of 6-chloroisatin (10.39 g, 57.2 mmol), 1,3-propanediol (10.74 mL, 143 mmol, 2.5 eq) and p-toluenesulfonic acid monohydrate (2.18 g, 11.4 mmol, 0.2 mol %) in benzene (1 L) was heated to reflux under a Dean Stark Trap for 20 hr. Additional p-toluenesulfonic acid (5.44 g, 0.5 mol %) and 1,3-propanediol (5 mL) was added and the reaction was refluxed for an additional 4 hr then stirred at room temperature overnight. The reaction was concentrated and the residue was taken up in EtOAc, washed with sat. aq. NaHCO$_3$ (3×), water (3×), dried over Na$_2$SO$_4$, filtered, and concentrated. The crude product was purified on Biotage KP silica gel eluting with 96/4 (CH$_2$Cl$_2$/CH$_3$OH) to give an orange gummy solid (13.25 g, 97%) which was triturated with CH$_3$OH (100 mL) to give the title compound as an orange colored solid (8.85 g, 64.6% yield). NMR (400 MHz, DMSO-d$_6$): consistent. MS: (API-ES−) m/z 237/239 [M−H] 1 chlorine pattern observed.

Step 4: 3-(6'-Chloro-2'-oxospiro[1,3-dioxane-2,3'indol]-1'(2'H)-yl)propanenitrile

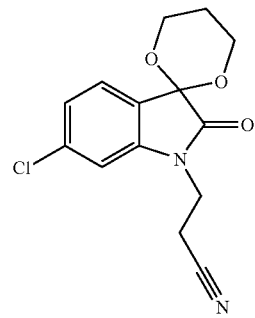

A mixture of 6'-chlorospiro[1,3-dioxane-2,3'-indol]-2'(1'H)-one (8.85 g, 36.9 mmol), and benzyltrimethylammonuim hydroxide (40% aqueous solution, 1.46 mL, 3.69 mmol, 0.1 mole %) in anhydrous DMF was heated to 65° C. Acrylonitrile (4.86 mL, 73.9 mmol, 2 eq) was added drop-wise by syringe under a dry N$_2$ atmosphere. After stirring 65 hr. the reaction was cooled to room temperature and poured into water (750 mL) and extracted with Et$_2$O (3×). The combined organic extracts were dried over Na$_2$SO$_4$ and concentrated. The crude product was purified on Biotage KP silica gel using a step gradient of 100% CH$_2$Cl$_2$ followed by CH$_2$Cl$_2$/CH$_3$OH/NH$_4$OH (99.7/0.2/0.1) to give the title compound as a white solid (7.80 g, 73% yield). Anal: Calc'd for C$_{14}$H$_{13}$ClN$_2$O$_3$: C, 57.45; H, 4.48; N, 9.59. Found: C, 56.39; H, 4.35; N, 9.35. NMR (400 MHz, DMSO-d$_6$): consistent. IR: consistent; MS: (EI$^+$) m/z 292 [M+] 1 chlorine pattern observed. m.p.163-164° C.; HRMS: consistent.

Step 5: 7'-Chloro-3',4'-dihydrospiro[1,3-dioxane-2, 10'(2'H)-pyrimido[1,2-a]indole]

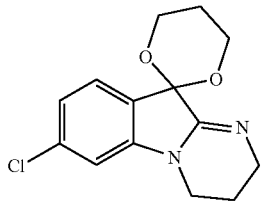

A mixture of 3-(6'-chloro-2'-oxospiro[1,3-dioxane-2,3'indol]-1'(2'H)-yl)-propanenitrile (7.45 g, 25.5 mmol) and wet Raney Nickel (3.58 g) in 2M EtOH.NH$_3$ (400 mL) and THF (50 mL) was hydrogenated in a Parr Hydrogenation Bottle (1 L) at 52 lb/in$^2$ H$_2$ for 24 hours. The Raney nickel was removed by filtration through Sulka Floc. The filtrate was concentrated and dissolved in 2MeOH.NH$_3$ (190 mL) and THF (10 mL), poured into a steel pressure bottle and heated to 135° C. for 18 hr. The reaction was cooled to room temperature and filtered to give the product as an off white solid (4.8 g, 63%). A portion was dried in vacuo at 30° C. to give the analytically pure sample. Anal: Calc'd. for C$_{14}$H$_{15}$ClN$_2$O$_2$: C, 60.33; H, 5.42; N, 10.05. Found: C, 60.41; H, 5.54; N, 10.00. NMR (400 MHz, DMSO-d$_6$): consistent. MS: (API-ES+) m/z 279/281 [M+H] 1 chlorine pattern observed. m.p.: 211-212° C. dec.

Step 6: 7-Chloro-3,4-dihydropyrimido(1,2-a)indol-10(2H)-one

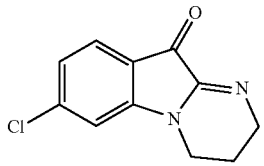

7'-Chloro-3',4'-dihydrospiro[1,3-dione-2,10'(2'H)-pyrimido[1,2-a]indole] (0.200 g, 0.718 mmol) was added portion-wise to cold concentrated $H_2SO_4$ (2.85 mL) with cooling in an ice bath. After stirring for one hour the dark red solution was added to ice and basified with concentrated $NH_4OH$ to pH 10.5 keeping the temperature cold with an external ice bath. The reaction mixture was extracted with EtOAc (2×), dried over $Na_2SO_4$, and concentrated to give the title compound as a bright orange solid (0.145 g, 94% yield). NMR (400 MHz, DMSO-$d_6$): consistent; Anal. Calc'd. for $C_{11}H_9ClN_2O$: C, 59.88; H, 4.11; N, 12.7. Found: C, 59.57; H, 3.99; N, 12.50. NMR: consistent; MS: (API-ES+) m/z 221/223 [M+H] 1 chlorine pattern observed; m.p. 164-167° C.

Step 7: 7-Chloro-10-oxo-2,3,4,10-tetrahydropyrimido[1,2-a]indole-8-sulfonyl chloride

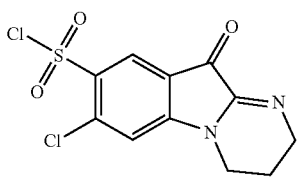

Chlorosulfonic acid (6 mL, 90.3 mmol, 12.2 eq) was added slowly to solid 7-chloro-3,4-dihydropyrimido(1,2-a)indol-10-(2H)-one (1.64 g, 7.43 mmol) with cooling in an ice bath. The ice bath was removed and the reaction mixture was heated to 65-78° C. for 2 hours. After cooling to room temperature the reaction was added drop-wise via pipette onto ice keeping the temperature cold with an external ice bath. The reaction mixture was extracted with $CHCl_3$ (3×) and $CH_2Cl_2$ (2×). The combined organic extracts were dried over $MgSO_4$ and concentrated. The crude product was purified on Biotage KP silica gel eluting with EtOAc to give the title compound as a bright yellow solid (0.142 g, 6% yield). NMR (400 MHz, DMSO-$d_6$): consistent.

Step 8: 7-Chloro-8-{[(2S)-2-(methoxymethyl)pyrrolidin-1-yl-]sulfonyl}-3,4-dihydropyrimido[1,2-a]indol-10(2H)-one

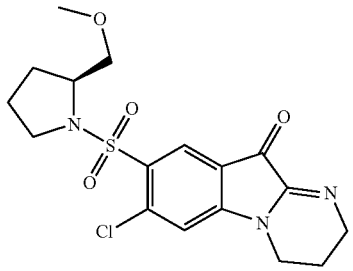

To a solution of 7-chloro-10-oxo-2,3,4,10-tetrahydropyrimido[1,2-a]indole-8-sulfonyl chloride (0.140 g, 0.439 mmol) in $CH_2Cl_2$ (10 mL) was added (S)-(+)-2-(methoxymethyl)pyrrolidine (0.119 g, 0.965 mmol, 2.2 eq) drop-wise with cooling in an ice bath under a dry $N_2$ atmosphere. After stirring at room temperature for 1.5 hr, the mixture was quenched with $H_2O$ (10 mL) and extracted with EtOAc (3×). The combined organic extracts were dried over $MgSO_4$, filtered, and concentrated to give a film on glass. The film was combined with the product of an earlier run and purified on Biotage KP silica gel eluting with a step gradient of 20/80 petroleum ether/EtOAc, followed by 100% EtOAc to give the title compound as a bright yellow solid (0.104 g, 52.3% yield). Anal. Calc'd. for $C_{17}H_{20}ClN_3O_4S \cdot 0.2H_2O$: C, 50.86; H, 5.12; N, 10.47. Found, C, 50.82; H, 5.00; N, 10.31. NMR (400 MHz, DMSO-$d_6$): consistent. MS: (ES$^-$) m/z 396/398 [M–H] 1 chlorine pattern observed. m.p.: 127-130° C. HRMS: consistent ESI Adduct [M+H] Exact 398.09358, Expt'l 398.09411, mmu 0.53, ppm 1.34, RI % 100.

Example 6

8-{[(2R)-2-(Methoxymethyl)pyrrolidin-1-yl]sulfonyl}-3,3-dimethyl-3,4-dihydropyrimido[1,2-a]indol-10(2H)-one

Step 1: 5-{[(2R)-2-(Methoxymethyl)pyrrolidin-1-yl]sulfonyl}-1H-indole-2,3-dione

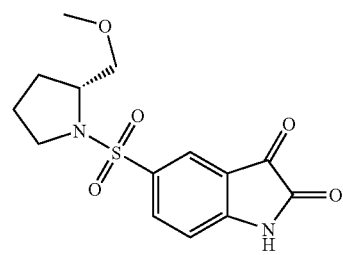

To a stirred cold suspension of 2,3-dioxo-2,3-dihydro-1H-indol-5-sulfonyl chloride (5.00 g, 20.4 mmol) in a 1:1 mixture of THF: $CHCl_3$ (140 mL) was added dropwise, via syringe pump, a solution of N,N-diisopropylethylamine (7.11 mL, 40.8 mmol, 2 eq) and (R)-2-(Methoxymethyl) pyrrolidine (3.27 mL, 26.5 mmol, 1.3 eq) in $CHCl_3$ (60 mL) over a period of 1.5 hours with cooling in an ice bath. After stirring an additional 1 h, the reaction was concentrated. The crude product was purified on Biotage KP silica gel eluting with 95/5 CH$_2$Cl$_2$/CH$_3$OH followed by a second chromatography on silica gel eluting with EtOAc to give 4.21 g (63.8%) of the title compound. NMR (400 MHz, DMSO-d$_6$): consistent.

Step 2: 5'-{[(2R)-2-(Methoxymethyl)pyrrolidin-1-yl]sulfonyl}spiro[1,3-dioxane-2,3'-indol]-2'(1'H)-one

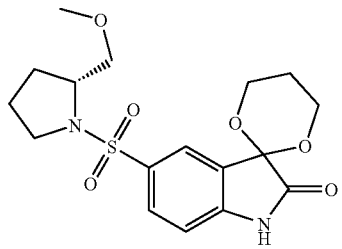

To a rapidly and efficiently stirred mixture of 5-{[(2R)-2-(methoxymethyl)pyrrolidin-1-yl]sulfonyl}-1H-indole-2,3-dione (4.21 g, 13.0 mmol) in benzene (300 mL), was added 1,3-propanediol (3.81 mL, 52 mmol, 4 eq) and p-toluenesulfonic acid (0.989 g, 5.2 mmol, 0.4 mole%) and the reaction was refluxed with a Dean Stark Trap for 4.5 hours under a dry N$_2$ atmosphere. After cooling to room temperature the reaction was washed with sat. aq. NaHCO$_3$ (3×), water (3×), brine (3×), dried over MgSO$_4$, and concentrated. The crude product was purified on Biotage KP silica gel eluting with 50/50 Pet ether/EtOAc to give the title compound as a white solid (1.34 g, 27% yield). NMR (400 MHz, DMSO-d$_6$): consistent; MS: (API-ES$^-$) m/z 381 [M−H]. MS: (API+ES$^+$) m/z 383 [M+H].

Step 3: 3-[5'-{[(2R)-2-(Methoxymethyl)pyrrolidin-1-yl]sulfonyl}2'-oxospiro[1,3'-indol]-1'(2'H)-yl]-2,2-dimethylpropanenitrile

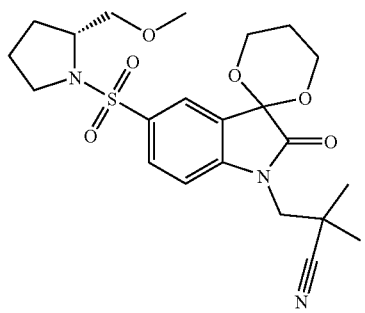

At room temperature, to a stirred solution of potassium-t-butoxide (0.465 g, 4.14 mmol, 1.2 eq) in anhydrous DMSO (11 mL) was added 5'-{[(2R)-2-(methoxymethyl)pyrrolidin-1-yl]sulfonyl]spiro[1,3-dioxane-2,3'-indol]-2'(1'H)-one (1.32 g, 3.45 mmol) all at one time under a dry N$_2$ atmosphere. After stirring 10 minutes, 3-chloro-2,2-dimethylpropionitrile (1.22 g, 10.4 mmol, 3 eq) was added and the reaction was heated at 130° C. for 72 hours. Additional potassium-t-butoxide (0.181 g, 1.61 mmol, 0.47 eq) was added to the reaction and heating continued at 130° C. for another 24 hours. After cooling to room temperature, the mixture was poured into H$_2$O (150 mL) and extracted with Et$_2$O (4×). The combined organic extracts were dried over Na$_2$SO$_4$ and concentrated. The crude product was purified on Biotage KP silica gel eluting with 50/50 Pet ether/EtOAc to give the title compound as a white solid (1.00 g, 63% yield). NMR (400 MHz, DMSO-d$_6$): consistent.

Step 4: 8'-{[(2R)-2-(Methoxymethyl)pyrrolidin-1-yl]sulfonyl}-3',3'-dimethyl-3',4'-dihydro-2'H-spiro[1,3-dioxane-2,10'pyrimido[1,2-a]indole]

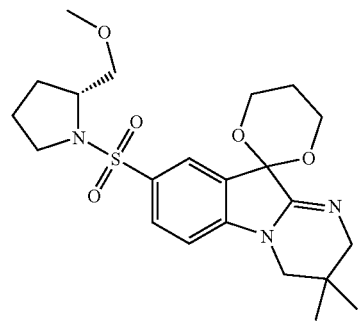

3-[5'-{[(2R)-2-(Methoxymethyl)pyrrolidin-1-yl]sulfonyl}-2'-oxospiro[1,3-dioxane-2,3'-indol]-1'(2'H)-yl]-2,2-dimethylpropanenitrile (1.00 g, 2.16 mmol), wet Raney Nickel (1.16 g) and 2M EtOH.NH$_3$ (100 mL) was hydrogenated in a Parr Bottle (500 mL) at 56 lb/in$^2$ H$_2$ for 18 hours. The Raney nickel was removed by filtration through Sulka Floc. The filtrate was poured into a steel pressure vessel and was heated at 135° C. for 20 hours. The mixture was cooled to room temperature and concentrated. The crude product was purified on Biotage KP silica gel eluting with CH$_2$Cl$_2$/CH$_3$OH/NH$_4$OH (97.75/1.5/0.75) to give the title compound as a white solid. Anal: Calc'd for C$_{22}$H$_{31}$N$_3$O$_5$S+0.2M H$_2$O: C, 58.31%; H, 6.98%; N, 9.27%. Found: C, 58.10; H, 6.96; N, 9.06. NMR (400 MHz, DMSO-d$_6$): consistent. MS: (ES+) m/z 450 [M+H]. Opt. Rotation: +75.02(calculated) at 25° C. in CH$_2$Cl$_2$ (1% concentration) at 589 wavelength; Analytical HPLC: major component=99.3% at 254 nm; m.p.: 169-171° C.

Step 5: 8-{[(2R)-2-(Methoxymethyl)pyrrolidin-1-yl]sulfonyl}-3,3-dimethyl-3,4-dihydropyrimido[1,2-a]indol-10(2H)-one

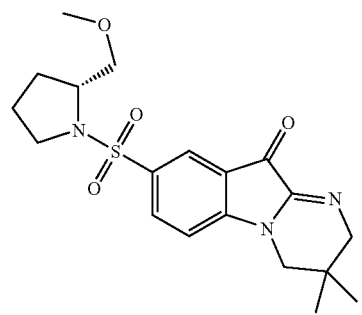

8'-{[(2R)-2-(Methoxymethyl)pyrrolidin-1-yl]sulfonyl}-3',3'-dimethyl-3',4'-dihydro-2'H-spiro[1,3-dioxane-2,10'pyrimido[1,2-a]indole] (0.765 g, 1.70 mmol) was added portion-wise to cold concentrated H₂SO₄ (10 mL) over a period of 0.5 hr. with cooling in an ice bath. The bath was removed and the reaction stirred at room temp for 1 hr. The reaction mixture was gradually added to ice over a period of 15 min. and was basified to pH 11.1 with concentrated NH₄OH keeping the temperature cold by the addition of ice and an external ice bath. The reaction was filtered and the collected solid was dissolved in CH₂Cl₂, dried over Na₂SO₄ and concentrated to give the title compound as a bright yellow solid (0.601 g, 90% yield). NMR (400 MHz, DMSO-d₆): consistent. IR: consistent. MS: (ES+) m/z 392 [M+H]. Opt. Rot: +74.84 (calculated) in CH₂Cl₂ (1% concentration) wavelength 589, 25° C.; m.p.: 161-164° C.

Example 7

N-Methyl-10-oxo-2,3,4,10-tetrahydropyrimido[1,2-a]indole-8-sulfonamide

Step 1:
N-Benzyl-N-methyl-2,3-dioxoindoline-5-sulfonamide

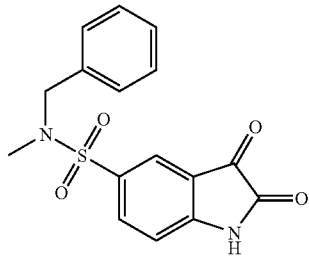

To a black solution of 2,3-Dioxo-2,3-dihydro-1H-indole-5-sulfonylchloride (4.00 g, 16.3 mmol) in 1:1 THF:CHCl₃ was added, drop-wise via syringe pump, a solution of N-benzylmethylamine (2.73 mL, 21.2 mmol, 1.3 eq) and N,N-diisopropylethylamine (5.68 mL, 32.6 mmol, 2 eq) in CHCl₃ (32 mL) over a period of 1.25 hr. with cooling in an ice bath. After stirring for 50 min. the reaction was allowed to warm to room temperature and stirred for 30 minutes. The reaction was concentrated. The crude product was purified on Biotage KP silica gel eluting with 98/2 CHCl₂/CH₃OH to give the analytically pure sample of the title compound as a bright yellow solid (0.18 g, 15% yield). Anal. Calc'd for C₁₆H₁₄N₂O₄S: C, 58.17; H, 4.27; N, 8.48. Found: C, 57.88; H, 4.36; N, 8.40. MS: (API-ES⁻) m/z 329 [M–H]. m.p.: 183-185° C.

Step 2: N-Benzyl-N-methyl-2'-oxo-1',2'-dihydrospiro[1,3-dioxane-2,3'-indole]-5'-sulfonamide

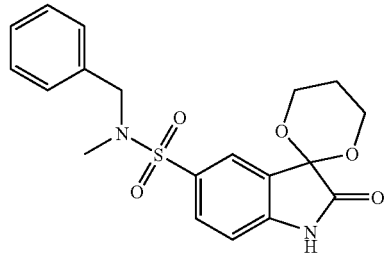

A mixture of N-benzyl-N-methyl-2,3-dioxoindoline-5-sulfonamide (2.88 g, 7.8 mmol), 1,3-propane-diol (1.43 mL, 19.5 mmol, 2.5 eq) and para toluene-sulfonic acid hydrate (0.296 g, 1.56 mmol, 0.2 eq) in benzene (135 mL) was refluxed with a Dean Stark Trap for 3.5 hours and stirred at room temperature overnight. The reaction was washed with NaHCO₃ (2×), water (2×) and brine (2×) and concentrated. The crude product was purified on Biotage KP silica gel eluting with a step gradient of 35/65 to 45/55 Pet. ether/EtOAc to give the title compound as a bright yellow solid (1.33 g, 44% yield). NMR (300 MHz, DMSO-d₆): consistent.

Step 3: N-Benzyl-1'-(2-cyanoethyl)-N-methyl-2'-oxo-1',2'-dihydrospiro[1,3-dioxane-2,3'-indole]-5'-sulfonamide

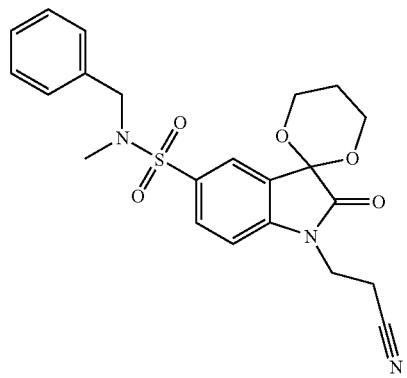

A mixture of N-benzyl-N-methyl-2'-oxo-1',2'-dihydrospiro[1,3-dioxane-2,3'-indole]-5'-sulfonamide (1.00 g, 2.57 mmol) and benzyltrimethylammonium hydroxide (40% aqueous sol'n, 0.112 mL, 0.617 mmol, 0.24 mole %) in absolute EtOH (20 mL) was heated to 78° C. and acrylonitrile (0.424 mL, 6.44 mmol, 2.5 eq) was added drop-wise. The reaction mixture was heated for 40 minutes longer, cooled to room temperature and filtered. The product was washed with ethanol and dried to give the title compound as a white solid (0.95 g, 84% yield). NMR (300 MHz, DMSO-d₆): consistent.

Step 4: N-Benzyl-N-methyl-3',4'-dihydrospiro[1,3-dioxane-2,10'(2'H)-pyrimido[1,2-alpha]-indole]-8'-sulfonamide

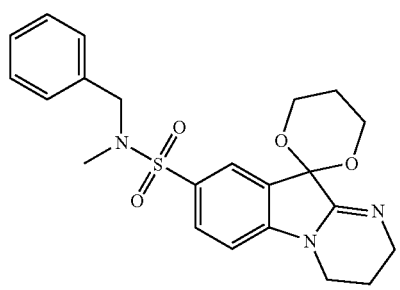

A suspension containing N-benzyl-1'-(2-cyanoethyl)-N-methyl-2'-oxo-1',2'-dihydrospiro[1,3-dioxane-2,3'-indole]-5'-sulfonamide (1.38 g, 3.13 mmol), wet Raney Nickel (1.23 g) and 2M EtOH.NH₃ (100 mL) in THF (20 mL) was hydrogenated in a Parr Bottle (250 mL) at 48 lb/in² hydrogen for 20 hours. The Raney Nickel was removed by filtration through Sulka Floc and the filtrate concentrated. The crude product was purified on Biotage KP silica gel eluting with CH$_2$C$_{12}$/MeOH/NH$_4$OH (94.75/3.5/1.75) to give the title compound as a white solid (1.31 g, 94% yield).

The amine was put into a steel pressure vessel with THF (20 mL) and 2M EtOH.NH₃ (100 mL) and heated to 135° C. for 16 hours. After cooling to room temperature the reaction was concentrated and purified on Biotage KP silica gel eluting with 40/60 Pet. Ether/EtOAc to give the title compound as a white solid (1.00 g, 81% ). Anal. Calc'd. for C$_{22}$H$_{25}$N$_3$O$_4$S: C, 61.81; H, 5.89; N, 9.83. Found: C, 61.68; H, 5.87; N, 9.75. NMR (400 MHz, DMSO-d$_6$): consistent. MS: m/z 428 [M+H]. m.p: 178-180° C.

Step 5: N-Methyl-10-oxo-2,3,4,10-tetrahydropy-rimido[1,2-a]indole-8-sulfonamide

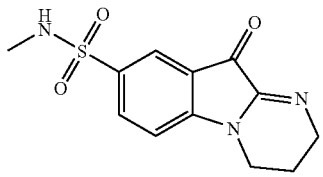

To cold concentrated H$_2$SO$_4$ (6 mL) was added N-benzyl-N-methyl-3',4'-dihydrospiro[1,3-dioxane-2,10'(2'H)-pyrimido[1,2-alpha]-indole]-8'-sulfonamide (0.500 g, 1.17 mmol) in small portions over a period of 15 minutes. After stirring for 40 min. the reaction was allowed to warm to room temperature and stirred 40 min. The reaction mixture was poured onto ice and basified to pH 10 with the slow addition of concentrated NH$_4$OH keeping the temperature cold with an external ice bath. The resulting yellow solid was filtered. The crude product was purified on Biotage KP silica gel eluting with CH$_2$Cl$_2$/MeOH/NH$_4$OH (95.5/3/1.5) to give the title compound as a yellow solid (0.23 g, 70% yield). Anal. Calc'd. for C$_{12}$H$_{13}$N$_3$O$_3$S: C, 51.60; H, 4.69; N, 15.04. Found: C, 51.51; H, 4.78; N, 15.06. NMR (400 MHz, DMSO-d$_6$): consistent. MS: (ESI⁺) m/z 280 [M+H]. m.p. 170-183° C. dec.

Example 8

8-{[(2S)-2-(Hydroxymethyl)pyrrolidin-1-yl]sulfonyl}-3,3-dimethyl-3,4-dihydropyrimido[1,2-a]indol-10(2H)-one Step 1: 5'-({(2S)-2-[(Benzyloxy)methyl]pyrrolidin-1-yl}sulfonyl)-1H-indole-2,3-dione

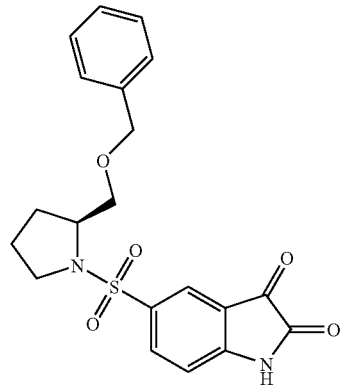

To a suspension of 2,3-dioxo-2,3-dihydro-1-H-indole-5-sulfonyl chloride (9.33 g, 38.0 mmol) in a 1:1 mixture of CHCl$_3$:THF (410 mL) was added drop-wise a solution of (2S)-2-[(benzyloxy)methyl]pyrrolidine (8.00 g, 41.8 mmol, 1.1 eq) and N,N-diiso-propylethylamine (12.2 mL, 69.8 mmol, 1.8 eq) in chloroform (63 mL) over 1.25 hours with cooling in an ice bath under a dry N$_2$ atmosphere. The reaction was complete (by TLC) after stirring for 1 hour at room temperature. The reaction was concentrated and purified on silica gel eluting with 50/50 Pet ether/EtOAc to give the title compound as a bright orange solid (11.8 g, 77.6% yield). NMR (400 MHz, DMSO-d$_6$): consistent.

Step 2: 5'-({(2S)-2-[(Benzyloxy)methyl]pyrrolidin-1-yl}sulfonyl)spiro[1,3-dioxane-2,3'-indol]-2'(1'H)-one

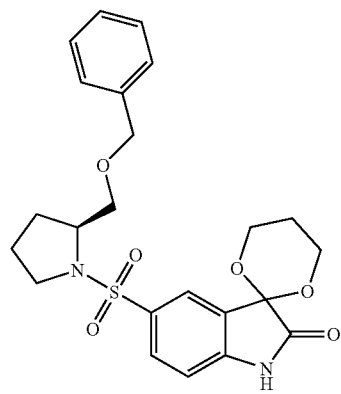

A suspension of 5'-({(2S)-2-[(benzyloxy)methyl]pyrrolidin-1-yl}sulfonyl)-1H-indole-2,3-dione (11.8 g, 29.5 mmol), p-toluenesulfonic acid monohydrate (2.24 g, 11.8 mmole, 0.4 mole %) and 1,3-propanediol (8.63 mL, 118 mmole, 4eq) in benzene (527 mL), was refluxed for 14 hr with a Dean Stark Trap. After cooling to room temperature, the reaction was washed with sat. aq. NaHCO$_3$ (3×), water (3×) and brine (3×), dried over Na$_2$SO$_4$, filtered and concentrated. The crude product was purified on silica gel eluting with 60/40 pet ether/EtOAc to give the title compound as a yellow foam (12.25 g, 90% yield). NMR (400 MHz, DMSO-d$_6$): consistent; MS: (API-ES+) m/z 457 [M+H, 100].

Step 3: 3-[5'-({(2S)-2-[(Benzyloxy)methyl]pyrrolidin-1-yl}sulfonyl)-2'-oxospiro[1,3-dioxane-2,3'-indol]-1'(2'H)-yl]-2,2-dimethylpropanenitrile

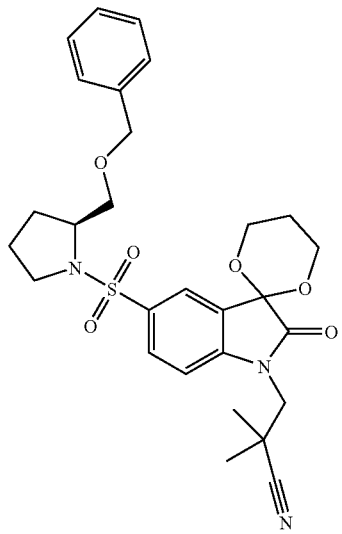

To a solution of potassium t-butoxide (3.58 g, 31.9 mmol, 1.2 eq) in anhyd DMSO (72 mL) was added 5'-({(2S)-2-[(benzyloxy)methyl]pyrrolidin-1-yl}sulfonyl)spiro[1,3-dioxane-2,3'-indol]-2'(1'H)-one (12.20 g, 26.6 mmol) all at one time under a dry N$_2$ atmosphere. After stirring 20 minutes, 3-chloro-2,2-dimethylpropionitrile (9.38 g, 79.8 mmol, 3 eq) was added drop-wise and the reaction was heated at 132° C. for 21 hr. After cooling in an ice bath, the reaction mixture was poured into H$_2$O and extracted with Et$_2$O. The combined organic extracts were dried over Na$_2$SO$_4$, filtered and concentrated. The crude product was purified on Biotage KP silica gel using a step gradient of CH$_2$Cl$_2$/CH$_3$OH/NH$_4$OH (99.25/0.5/0.25 to 96/2/1) to give the title compound as a yellow solid (9.48 g, 66% yield). NMR (400 MHz, DMSO-d$_6$): consistent.

Step 4: 8'-({(2S)-2-8 (Benzyloxy)methyl]pyrrolidin-1-yl}sulfonyl)-3',3'-dimethyl-3',4'dihydro-2'H-spiro[1,3-dioxane-2,10'-pyrimido[1,2-a]indole]

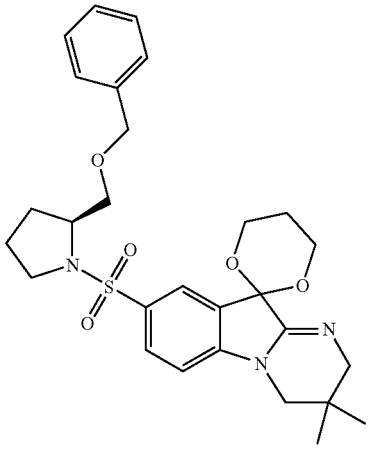

A mixture of 3-[5'-({(2S)-2-[(benzyloxy)methyl]pyrrolidin-1-yl}sulfonyl)-2'-oxospiro[1,3-dioxane-2,3'-indol]-1' (2'H)-yl]-2,2-dimethylpropanenitrile (3.00 g, 5.56 mmol), wet Raney Nickel (3.18 g) in 2M EtOH.NH$_3$ (180 mL) and THF (30 mL) was hydrogenated at 54 lb/in$^2$ H$_2$ for 22 hr. The reaction was filtered through Sulka Floc and the filtrate was poured into a steel pressure vessel and heated to 132° C. for 18 hr. After cooling to room temperature the reaction was concentrated. The crude product was purified on Biotage KP silica gel eluting with CH$_2$Cl$_2$/CH$_3$OH/NH$_4$OH (98.5/1/0.5) to give the title compound as a white solid (1.77 g, 60%). NMR (400 MHz, DMSO-d$_6$): consistent.

Step 5: 8-{[(2S)-2-(Hydroxymethyl)pyrrolidin-1-yl]sulfonyl}-3,3-dimethyl-3,4-dihydropyrimido[1,2-a]indol-10(2H)-one

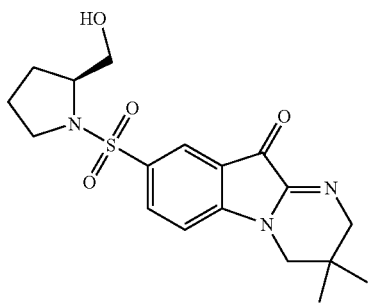

To neat 8'-({(2S)-2-[(benzyloxy)methyl]pyrrolidin-1-yl}sulfonyl)-3',3'-dimethyl-3',4'-dihydro-2'H-spiro[1,3-dioxane-2,10'-pyrimido[1,2-a]indole] (0.500 g, 0.951 mmol) was added methane sulfonic acid (24 mL) all at one time at room temperature. After 5 hr the reaction mixture was poured onto ice and basified to pH 11.2 by the drop-wise addition of concentrated NH$_4$OH keeping the temperature below 5° C. The reaction was extracted with EtOAc (5×). The combined organic extracts were dried over Na$_2$SO$_4$, filtered and concentrated. The crude product was purified on Biotage KP silica gel eluting with CH$_2$Cl$_2$/CH$_3$OH/NH$_4$OH (94.75/3.5/1.75) to give the title compound as a bright orange solid (0.28 g, 68% yield). A 100 mg sample was dried at 63° C. in vacuo to give the analytically pure sample. Anal. Calc'd for; $C_{18}H_{23}N_3O_4S$: C, 57.28; H, 6.14; N, 11.13. Found: C, 57.05; H, 5.99; N, 10.79. NMR (400 MHz, DMSO-$d_6$): consistent. MS: (ES+) m/z 378 [M+H]. m.p.: 91-96° C. dec.

Example 9

8-Bromo-3,4-dihydropyrimido[1,2-a]indol-10(2H)-one

Step 1: 5'-Bromospiro[1,3-dioxane-2,3'-indol]-2'(1'H)-one

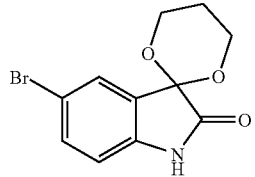

A mixture of 5-bromoisatin (5.00 g, 22.1 mmol), 1,3 propanediol (4.86 mL, 66.4 mmol, 3 eq) and p-toluenesulfonic acid monohydrate (0.84 g, 4.42 mmol, 0.2 mole %) in benzene (430 mL) was refluxed with a Dean Stark Trap for 5 hr. The mixture was concentrated and washed with sat. aq. NaHCO$_3$ (2x) and brine (1x) and flash chromatographed (Biotage KP silica gel, step gradient 70/30-60/40 Petroleum ether/EtOAc) to give the title compound as a bright yellow solid (2.86 g, 46% ). Anal. Calc'd for $C_{11}H_{10}BrNO_3$: C, 46.50; H, 3.55; N, 4.93. Found: C, 46.82; H, 3.54; N, 4.82. IR: consistent. NMR (300 Mz, DMSO-$d_6$): consistent. MS: (ESI$^-$) $^{m/z}$ 281/283 [M–H], 1 Br pattern observed. m.p.: 202-203° C.

Step 2: 3-(5'-Bromo-2'-oxospiro[1,3-dioxane-2,3'-indol]-1'(2'H)-yl)propanenitrile

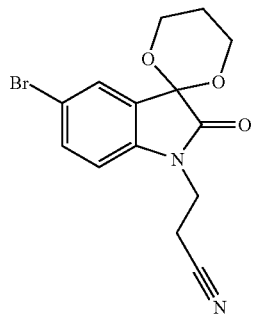

At room temperature, to a solution of 5'-bromospiro[1,3-dioxane-2,3'-indol]-2'(1'H)-one (2.50 g, 8.80 mmol) in N,N dimethylformamide (39 mL) was added benzyltrimethylammonium hydroxide (40% aq. solution, 0.347 mL, 0.88 mmol, 0.1 mole % ) followed by the dropwise addition of acrylonitrile (1.16 mL, 17.6 mmol, 2 eq). The reaction mixture was heated at 52° C. for 2 hr., cooled to room temperature, quenched with H$_2$O (400 mL) and extracted with Et$_2$O (3x). The combined organic extracts were dried and concentrated. The crude product was purified on Biotage KP silica gel eluting with 96/4 CH$_2$Cl$_2$/CH$_3$CN to give the title compound as a yellow solid (2.11 g, 71% ). NMR (300 Mz, DMSO-$d_6$): consistent; MS: (API-ES$^+$) m/z 361 [M+Na].

Step 3:1 '-(3-Aminopropyl)-5'-bromospiro[1.3-dioxane-2,3'-indol]-2'(1'H)-one

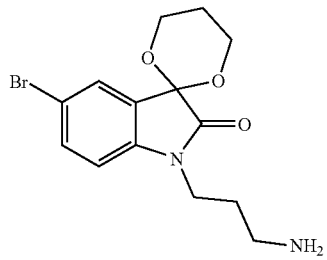

A mixture of 3-(5'-bromo-2'-oxospiro[1,3-dioxane-2,3'-indol]-1'(2'H)-yl)propanenitrile (2.08 g, 6.17 mmol), and wet Raney Nickel (2.44 g) in 2M EtOH.NH$_3$ (132 mL) and THF (30 mL) was hydrogenated in a Parr Hydrogenation Bottle (500 mL) at 55 lb/in$^2$ H$_2$ for 24 hr. The Raney Nickel was removed by filtration through Celite and the filtrate was concentrated. The crude product was purified on Biotage KP silica gel eluting with CH$_2$Cl$_2$/CH$_3$OH/NH$_4$OH (96.25/2.5/1.25) to give 2.04 g. (98% ) of the title compound as a clear colorless oil.

Step 4: 8'-Bromo-3',4'-dihydrospiro[1,3-dioxane-2,10'(2'H)-pyrimido[1,2-a]indole]

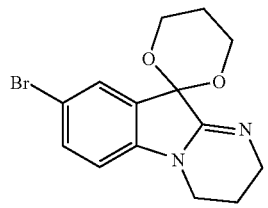

A mixture of 1'-(3-aminopropyl)-5'-bromospiro[1,3-dioxane-2,3'-indol]-2'(1'H)-one (1.89 g, 5.54 mmol) in 2M EtOH.NH$_3$ (150 mL) was heated in a steel pressure vessel at 135° C. for 46 hr. After cooling to room temperature the reaction was concentrated. The crude product was purified on Biotage KP silica gel eluting with 85/15 Pet ether/acetone to give the title compound (0.84 g, 66% ). A portion was dried in vacuo at 50° C. to give the analytically pure sample. Anal: Calc'd for $C_{14}H_{15}BrN_2O_2$: C, 52.03; H, 4.68; N, 8.67. Found: C, 52.10; H, 4.63; N 8.46. IR: consistent, NMR (300 Mz, DMSO-$d_6$): consistent. MS: (ESI$^+$) m/z 323 [M+H], 1 Br pattern observed. m.p.: 145-149° C.

Step 5:
8-Bromo-3,4-dihydropyrimido[1,2-a]indol-10(2H)-one

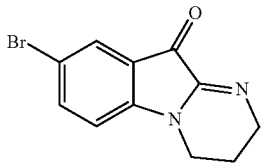

To cold concentrated H₂SO₄ (4.2 mL) was added 8'-bromo-3',4'-dihydrospiro[1,3-dioxane-2,10'(2'H)-pyrimido[1,2-a]indole] (0.400 g, 1.24 mmol) in four portions with cooling in an ice bath. The reaction was stirred at room temperature for one hr, poured onto ice and basified with the careful addition of NE₄OH keeping the temp cold with an external ice bath. The reaction mixture was extracted with EtOAc (3×). The combined organic extracts were dried over Na₂SO₄, filtered and concentrated to give the title compound as a red solid (0.332 g, 100% ). Anal: Calc'd for C₁₁H₉BrN₂O: C, 49.84; H, 3.42; N, 10.7. Found: C, 49.86; H, 3.37; N, 10.51. NMR (300 Mz, DMSO-d₆): consistent. MS: (ESI+) m/z 265 [M+H], one bromine pattern observed. m.p. 166-168° C., black melt.

Example 10

8-Methyl-3,4-dihydropyrimido[1,2-a]indol-10(2H)-one

Step 1: 5'-Methylspiro[1,3-dioxane-2,3'-indol]-2'(1'H)-one

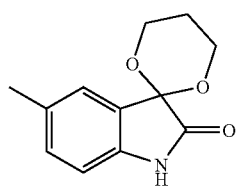

A mixture of 5-methylisatin (8.00 g, 49.6 mmol), 1,3 propanediol (10.89 mL, 149 mmol, 3 eq) and p-toluenesulfonic acid monohydrate (1.89 g, 9.92 mmol, 0.2 eq) in benzene (940 mL) was heated to reflux under a Dean Stark Trap for 17.5 hr. The reaction mixture was concentrated. The residue was taken up in EtOAc (300 mL) and washed with sat. aq. NaHCO₃ (2×) and concentrated. The crude product was purified on Biotage KP silica gel eluting with 60/40 Pet ether/EtOAc to give the title compound as a yellow solid (8.0 g., 74% yield). NMR (300 Mz, DMSO-d₆): consistent.

Step 2: 3-(5'-Methyl-2'-oxospiro[1,3-dioxane-1,3'-[3H]indol]-propanenitrile

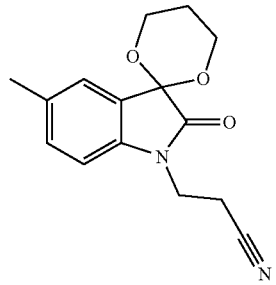

To a solution of 5'-methylspiro[1,3-dioxane-2,3'-indol]-2'(1'H)-one (3.33 g, 15.2 mmol) and benzyltrimethylammonium hydroxide (40% aq. soln., 0.600 mL, 1.52 mmol, 0.1 mole % ) in DMF (67 mL) was added acrylonitrile (2.00 mL, 30.4 mmol, 2 eq) drop-wise at room temperature. The mixture was heated at 52° C. for 3 hr, cooled to room temperature, and poured into H₂O (500 mL). The reaction mixture was extracted with Et₂O, washed with brine and concentrated. The crude product was purified on Biotage KP silica gel eluting with a step gradient 80/20 to 70/30 Pet ether/EtOAc to give the title compound as an off white solid (3.07 g, 72% yield). Anal. Calc'd for C₁₅H₁₆N₂O₃: C, 66.16; H, 5.92; N, 10.29. Found: C, 66.09; H, 5.94; N, 10.11. NMR (300 Mz, DMSO-d₆): consistent; MS: (APCl+) m/z 273 [M+H]. IR: consistent m.p.: 128-129° C.

Step 3: 1'-(3-Aminopropyl)-5'-methylspiro[1,3-dioxane-2,3'-indol]-2'(1'H)-one

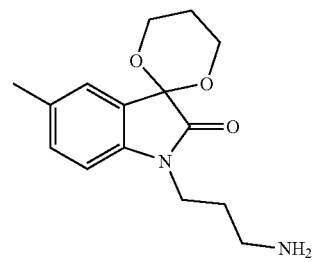

A mixture of 3-(5'-methyl-2'-oxospiro[1,3-dioxane-1,3'-[3H]indol]-propanenitrile (3.00 g, 11.0 mmol), and wet Raney Nickel (3.12 g) in 2M EtOH.NH₃ (250 mL) and THF (50 mL) were hydrogenated in a Parr Hydrogenation Bottle (250 mL) at 53 lb/in² H₂ for 18 hr. The reaction was filtered through Celite and the filtrate was concentrated. The crude product was purified on Biotage KP silica gel eluting with 60/40 Pet ether/EtOAc to give the title compound as a yellow solid (8.0 g, 74% ). NMR (300 Mz, DMSO-d₆: consistent.

Step 4: 8-Methyl-10-spiro[(1,3-dioxane)-2',10-(2,3,4,10-tetrahydropyrimido[1,2-a]indole)

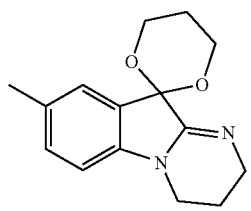

A solution of 1'-(3-aminopropyl)-5'-methylspiro[1,3-dioxane-2,3'-indol]-2'(1H)-one (3.00 g, 11.0 mmol) in 2M EtOH.NH$_3$ (200 mL) was poured into a steel pressure vessel and heated at 135° C. for 16 hr. The mixture was cooled to room temperature and concentrated. The crude product was purified on Biotage KP silica gel eluting with CH$_2$Cl$_2$/CH$_3$OH/NH$_4$OH (97.75/1.5/0.75) to give the title compound as a light orange solid (0.819 g, 56% yield). Anal: Calc'd for: C$_{15}$H$_{18}$N$_2$O$_2$: C, 69.74; H, 7.02; N, 10.84. Found: C, 69.73; H, 7.34; N, 10.89. NMR (300 Mz, DMSO-d$_6$): consistent; MS: (APCI+) m/z 259 [M+H]. m.p.: 128 -130° C.

Step 5: 8-Methyl-3,4-dihydropyrimido[1,2-a]indol-10(2H)-one

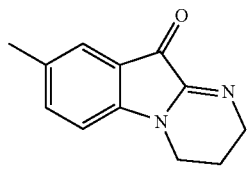

To cold concentrated H$_2$SO$_4$ (9 mL) was added solid 8-methyl-10-spiro[(1,3dioxane)-2',10-(2,3,4,10-tetrahydropyrimido[1,2-a]indole) (0.71 g, 2.7 mmol) portion-wise over a period of 25 min. with cooling in an ice bath. After stirring for an additional 20 minutes the reaction mixture was poured onto ice and basified with concentrated NH$_4$OH to pH 10 keeping the temperature cold with an external ice bath. The reaction mixture was extracted with EtOAc (100 mL). The combined organic extracts dried over K$_2$CO$_3$, filtered, concentrated to give the title compound as a bright red solid (0.542 g, 100% ). Anal: Calc'd for: C$_{12}$H$_{12}$N$_2$O0.1H$_2$O: C, 71.34; H, 6.09; N, 13.87. Found: C, 71.37; H, 6.07; N, 13.85. NMR (300 Mz, DMSO-d$_6$): consistent; MS: (APCI+) m/z 201 [M+H]. m.p.: 163-164° C.

Example 11

8-Methoxy-3,4-dihydropyrimido[1,2-a]indol-10(2H)-one

Step 1: 5'-Methoxy-2'-oxospiro[1,3-dioxane-1,3'-[3H]indol]

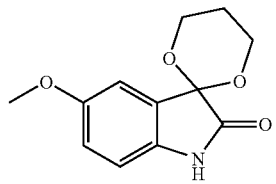

A mixture of 5-methoxyisatin (4.00 g, 22.6 mmol), p-toluenesulfonic acid monohydrate (0.860 g, 4.52 mmol, 0.2 mole %) and 1,3 propanediol (6.61 mL, 90 mmol, 4 eq) in benzene (440 mL) was refluxed with a Dean Stark Trap for 4.5 hr. After cooling to room temperature, the mixture was washed with sat. aq. NaHCO$_3$ (2×), with brine and concentrated. The crude product was purified on Biotage KP silica gel eluting with 60/40 Petroleum ether/EtOAc to give the title compound as a tan solid. NMR (300 Mz, DMSO-d$_6$) consistent.

Step 2: 3-(5'-Methoxy-2'-oxospiro[1,3-dioxane-2,3'-indol]-1'(2'H)-yl)propanenitrile

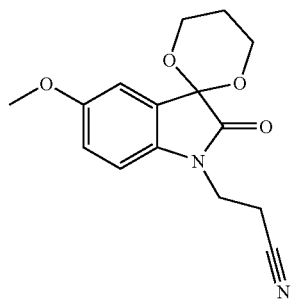

At room temperature, to a solution of 5'-methoxy-2'-oxospiro[1,3-dioxane-1,3'-[3H]indol] (2.76 g, 11.7 mmol) in DMF (52 mL) and benzyltrimethylammonium hydroxide (40% aqueous solution, 0.46 mL, 1.17 mmol, 0.1 eq) was added acrylonitrile (1.54 mL, 23.5 mmol, 2 eq) drop-wise via syringe. The reaction was heated at 41° C. for 1 hr, cooled to room temperature and poured into H$_2$O (500 mL). The reaction mixture was extracted with Et$_2$O (3×). The combined organic extracts were concentrated. The crude product was combined with the products from two previous runs and purified on Biotage KP silica gel eluting with 96/4 CH$_2$Cl$_2$/CH$_3$CN to give the title compound as a thick yellow oil (3.16, 81% ). NMR (300 Mz, DMSO-d$_6$): consistent. MS: (API-ES+) 311[M+Na].

Step 3: 8'-Methoxy-3',4'-dihydro-2'H-spiro[1,3-dioxane-2,10'pyrimido[1,2-a]indole]

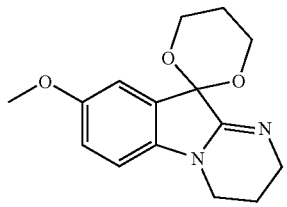

A mixture of 3-(5'-methoxy-2'-oxospiro[1,3-dioxane-2,3'-indol]-1'(2'H)-yl)propanenitrile (1.00 g, 3.47 mmol) and wet Raney Nickel (1.00 g) in 2M EtOH.NH$_3$ (45 mL) and THF (45 mL) was hydrogenated in a Parr Hydrogenation Bottle (250 mL) at 53 lb/in H$_2$ for 20 hr. The mixture was filtered through Celite and the filtrate was poured into a steel pressure vessel and heated at 135° C. for 66 hr. The reaction was cooled to room temperature and concentrated. The crude product was purified on Biotage KP silica gel eluting with a step gradient CH$_2$Cl$_2$/CH$_3$OH/NH$_4$OH (98.5/1/0.5 to 97/2/1) to give the title compound as a tan solid (0.26 g, 27%). NMR (300 Mz, DMSO-d$_6$): consistent. MS: (API-ES+) 275[M+H].

Step 4: 8-Methoxy-3,4-dihydropyrimido[1,2-a]indol-10(2H)-one

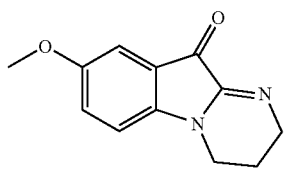

To cold concentrated H$_2$SO$_4$ (4 mL) was added 8'-methoxy-3',4'-dihydro-2'H-spiro[1,3-dioxane-2,10'-pyrimido[1,2-a]indole] (0.204 g, 0.744 mmol) portion-wise over a period of 15 minutes with cooling in an ice bath. After stirring for 35 min., the reaction was poured onto ice and basified with concentrated NH$_4$OH keeping the reaction cold with ice. The reaction mixture was extracted with EtOAc (3×). The combined organic extracts were dried over Na$_2$SO$_4$, and filtered and concentrated. The crude product was purified on Biotage KP silica gel eluting with CH$_2$Cl$_2$/CH$_3$OH/NH$_4$OH (98.5/1/0.5) to give the title compound as a bright red solid. Anal: Calc'd for C$_{12}$H$_{12}$N$_2$O$_2$ 0.1H$_2$O: C, 66.10; H, 5.64; N, 12.85. Found: C, 65.81; H, 5.28; N, 12.78. NMR (300 Mz, DMSO-d$_6$): consistent. MS: (APCI+) m/z 217[M+H]. m.p.: 152° C.

Example 12

3,3-Dimethyl-8-(pyrrolidin-1-ylsulfonyl)-3,4-dihydropyrimido[1,2-a]indol-10(2H)-one

Step 1: 5-(Pyrrolidin-1-ylsulfonyl)-1H-indole-2,3-dione

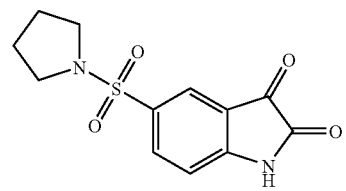

To a cold solution of 2,3-dioxo-2,3-dihydro-1H-indole-5-sulfonylchloride (2.00 g, 8.14 mmol) in a 1:1 mixture of THF: CHCl$_3$ (96 mL) was added drop-wise via syringe pump over a period of 1 hr a solution of pyrrolidine (0.885 mL, 10.6 mmol) and N,N-diisopropylethyl amine (2.84 mL, 16.3 mmol, 2 eq) in chloroform (16 mL) under a dry N$_2$ atmosphere with cooling in an ice bath. After stirring for 1 h., the reaction was concentrated. The crude product was purified on Biotage KP silica gel eluting with 80/20 CH$_2$Cl$_2$/EtOAc to give the title compound as a greenish-yellow solid (0.88 g, 39% yield). NMR (300 Mz, DMSO-d$_6$): consistent. MS: (ES−) m/z 279 [M−H].

Step 2: 5'-(Pyrrolidin-1-ylsulfonyl)spiro[1,3-dioxane-2,3'-indol]-2'(1'H)-one

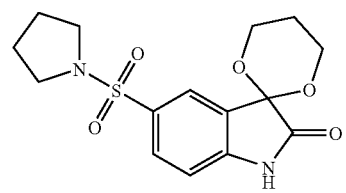

A stirred mixture of 5-(pyrrolidin-1-ylsulfonyl)-1H-indole-2,3-dione (0.88 g, 3.14 mmol), 1,3-propanediol (0.92 mL, 1.26 mmol, 4 eq) and p-toluenesulfonic acid (1.19 g, 6.28 mmol, 0.2 mole %) in benzene (100 mL) was refluxed with a Dean Stark Trap for 6 hours. The reaction was cooled to room temperature, washed with sat. aq. NaHCO$_3$ (1×), water (2×), and brine (1×), dried over NaHCO$_3$ (1×,), filtered and concentrated. The crude product was purified on Biotage KP silica gel eluting with 90/10 CH$_2$Cl$_2$/EtOAc to give the title compound as a white solid (0.72 g, 68%). NMR (300 Mz, DMSO-d$_6$): consistent. MS: (API-ES+) 338 [M+H] consistent.

Step 3: 2,2-Dimethyl-3-[2'-oxo-5'-(pyrrolidin-1-ylsulfonyl)spiro[1,3-dioxane-2,3'-indol]-1'(2'H)-yl]propanenitrile

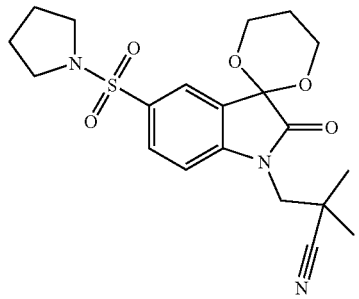

At room temperature, to a stirred solution of potassium t-butoxide (0.287 g, 2.56 mmol, 1.2 eq) in anhydrous DMSO (4 mL) was added 5'-(pyrrolidin-1-ylsulfonyl)spiro[1,3-dioxane-2,3'-indol]-2'(1'H)-one (0.72 g, 2.13 mmol). After stirring 20 minutes, 3-chloro-2,2-dimethylpropionitrile (3 eq) was added drop-wise and the reaction was heated at 130° C. for 20 hr. The reaction mixture was heated at 126° C. for 16 h. After cooling to room temperature, the reaction was poured into H$_2$O (100 mL) and extracted with Et$_2$O (3×). The combined organic extracts were dried over Na$_2$SO$_4$, filtered and concentrated. The crude product was purified on Biotage KP silica gel eluting with CH$_2$Cl$_2$/CH$_3$OH H$_4$OH (97/2/1) followed by a second chromatography eluting with 50/50 Pet. ether/EtOAc to give the title compound as a white solid (0.69 g, 77% yield). NMR: consistent.

Step 4: 3',3'-Dimethyl-8'-(pyrrolidin-1-ylsulfonyl)-3',4'-dihydro-2'H-spiro[1,3-dioxane-2,10'-pyrimido[1,2-a]indole]

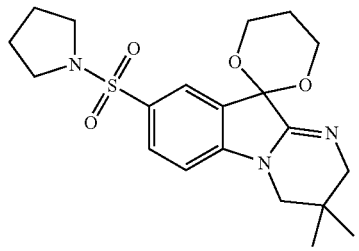

A mixture of 2,2-dimethyl-3-[2'-oxo-5'-(pyrrolidin-1-ylsulfonyl)spiro[1,3-dioxane-2,3'-indol]-1'(2'H)-yl]propanenitrile (0.69 g, 1.64 mmol) and wet Raney Nickel (0.70 g) in 2M EtOH.NH$_3$ (50 mL) and THF (20 mL) was hydrogenated in a Parr hydrogenation bottle (500 mL) at 541 b/in$^2$ hydrogen for 67 hr. The Raney Nickel was removed by filtration through Sulka Floc and the filtrate was poured into a steel pressure vessel, diluted with 2M EtOH.NH$_3$ (50 mL) and THF (20 mL) and heated at 135° C. for 22 hr. The reaction was cooled to room temperature and concentrated. The crude product was purified on Biotage KP silica gel eluting with CH$_2$Cl$_2$/CH$_3$OH/NH$_4$OH (98.5/1/.05) to give the title compound as a white solid (0.300 g, 45% yield). NMR: consistent. MS: (API-ES+) m/z 406 [M+H].

Step 5: 3,3-Dimethyl-8-(pyrrolidin-1-ylsulfonyl)-3,4-dihydropyrimido[1,2-a]indol-10(2H)-one

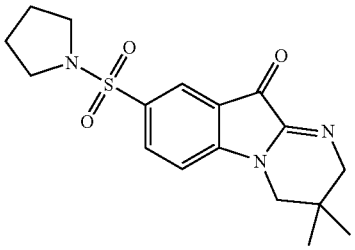

To 3',3'-dimethyl-8'-(pyrrolidin-1-ylsulfonyl)-3',4'-dihydro-2'H-spiro[1,3-dioxane-2,10'-pyrimido[1,2-a]indole] (0.231 g, 0.570 mmol) was added methane sulfonic acid (6 mL) and the mixture was heated at 60° C. for 3 hr. The reaction was cooled to room temperature, poured onto ice, and basified with concentrated NH$_4$O H to pH 11 keeping the reaction temperature below 5° C. The resulting orange solid was filtered, dissolved in CH$_2$Cl$_2$ and EtOAc, dried over Na$_2$SO$_4$, filtered, and concentrated to give the title compound as a bright yellow solid (0.155 g, 78% yield). Anal: Calc'd for C$_{17}$H$_{21}$N$_3$O$_3$S: C, 58.77; H, 6.09; N, 12.09. Found: C, 58.90; H, 6.20; N, 11.75. NMR (300 Mz, DMSO-d$_6$): consistent. MS: (ES−) 346 [M−H]. MS: (ES+) 348 [M+H]. m.p.: 200-201° C.

Example 13

8-Bromo-4-methyl-3,4-dihydropyrimido[1,2-a]indol-10(2H)-one

Step 1: 3-(5'-Bromo-2'-oxospiro[1,3-dioxane-2,3'-indol]-1'(2'H)-yl)butanenitrile

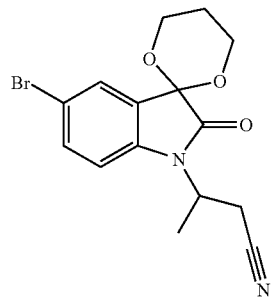

To a solution of 5'-bromospiro[1,3-dioxane-2,3'-indol]-2' (1'H)-one (2.00 g, 7.04 mmol) and benzyltrimethylammonium hydroxide (40% aqueous solution, 0.768 mL, 1.69 mmol, 0.24 mole %) in abs. EtOH (32 mL) was added allyl cyanide (1.42 mL, 17.6 mmol, 2.5 eq) all at one time at room temperature and the mixture was heated at 80° C. for 2.5 hr. Additional benzyltrimethyl-ammonium hydroxide (0.77 mL) was added and the heating continued another 24 hr. The reaction was cooled to room temperature and poured into H$_2$O (100 mL). The reaction mixture was extracted with EtOAc (3×). The combined organic extracts were concentrated. The crude product was purified on Biotage KP silica gel eluting with CH$_2$Cl$_2$/CH$_3$OH/NH$_4$OH (97/2/1) to give the title compound as a white solid (0.299 g, 16% ). Anal.

Calc'd for: $C_{15}H_{15}BrN_2O_3$: C, 51.3; H, 4.3; N, 7.98. Found: C, 51.55; H, 4.47; N 7.99. NMR (300 Mz, DMSO-$d_6$): consistent. MS: (ES+) m/z 350/352 [M+]; one Br pattern observed. m.p.: 112-113° C.

Step 2: 8'-Bromo-4'-methyl-3',4'-dihydro-2'H-spiro [1,3-dioxane-2,10'-pyrimido[1,2-a]indole]

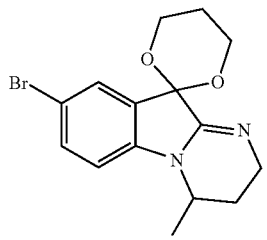

A mixture of 3-(5'-bromo-2'-oxospiro[1,3-dioxane-2,3'-indol]-1'(2'H)-yl)butanenitrile (0.751 g, 2.14 mmol), and wet Raney Nickel (0.75 g) in 2M EtOH.NH$_3$ (10 mL) was hydrogenated in a Parr Hydrogenation Bottle (500 mL) at 55 lb/in$^2$ H$_2$ for 23 hr. The Raney Nickel was removed by filtration through Sulka Floc and the filtrate was poured into a steel pressure vessel and heated at 135° C. for 69 hr. The reaction mixture was cooled to room temperature and concentrated. The crude product was purified on Biotage KP silica gel eluting with CH$_2$Cl$_2$/CH$_3$OH/NH$_4$OH (98/2/1) to give the title compound as a white solid (0.097 g, 13% yield). Anal. Calc'd for $C_{15}H_{17}BrN_2O_2$: C, 53.43; H, 5.08; N, 8.31. Found: C, 53.61; H, 5.12; N, 8.11. NMR (300 Mz, DMSO-$d_6$): consistent. MS: (ES+) m/z 337/339 [M+H]; one Br pattern observed. m.p.: 69-72° C.

Step 3: 8-Bromo-4-methyl-3,4-dihydropyrimido[1,2-a]indol-10(2H)-one

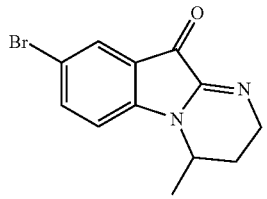

To cold concentrated H$_2$SO$_4$ (3 mL) was added 8'-bromo-4'-methyl-3',4'-dihydro-2'H-spiro[1,3-dioxane-2,10'-pyrimido[1,2-a]indole] (0.252 g, 0.747 mmol) in four portions with cooling in an ice bath. The reaction was then allowed to stir at room temperature for 1 hr. The mixture was poured onto ice and basified with NH$_4$OH to pH 11 with cooling in an external ice bath. The reaction mixture was extracted with Et$_2$O (2×). The combined organic extracts were dried over Na$_2$SO$_4$, filtered, and concentrated. The crude product was purified on Biotage KP silica gel eluting with CH$_2$Cl$_2$/ CH$_3$OH/NH$_4$OH (96/2/1) to give the title compound as a red solid (0.138 g, 66% ). Anal. Calc'd for $C_{12}H_{11}BrN_2O$: C, 51.64; H, 3.97; N, 10.04; Found: C, 51.23; H, 3.89; N, 9.88. NMR (300 Mz, DMSO-$d_6$): consistent. MS: (ES+) m/z 278/280 [M+H]; 1 Br pattern observed. m.p.: 127-129° C.

Example 14

8'-Chloro-3',3'-dimethyl-3',4'-dihydropyrimido[1,2-a]indol-10(2H)-one

Step 1: 5'-Chlorospiro[1,3-dioxane-2,3'-indol]-2' (1'H)-one

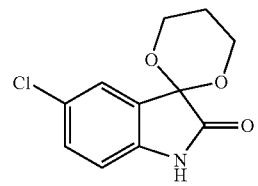

A mixture of 5-chloroisatin (5.00 g, 27.5 mmol), p-toluenesulfonic acid monohydrate (1.05 g, 5.5 mmol, 0.2 mole %) and 1,3 propanediol (6.04 mL, 83 mmol, 3 eq) in benzene (535 mL) was refluxed with a Dean Stark Trap for 7.5 hr. After cooling to room temperature the solution was decanted from the reaction mixture and concentrated The residue was washed with sat. aq. NaHCO$_3$ (2×), brine (1×), dried over Na$_2$SO$_4$, filtered and concentrated. The crude product was purified on Biotage KP silica gel eluting with 70/30 Petroleum ether/EtOAc to give the title compound as a pale yellow solid (4.77 g, 72.5% ). A portion was dried at 42° C. in vacuo to give the analytically pure sample. Anal: Calc'd for $C_{11}H_{10}ClNO_3$: C, 55.13; H, 4.21; N, 5.84. Found: C, 55.31; H, 4.34; N, 5.78. NMR (300 Mz, DMSO-$d_6$): consistent. IR: consistent. MS: (ES−) m/z 238 [M−H]; one Cl pattern observed, consistent. m.p.: 184-185° C.

Step 2: 3-(5'-Chloro-2'-oxospiro[1,3-dioxane-2,3'-indol]-1'(2'H)-yl)-2,2-dimethylpropanenitrile

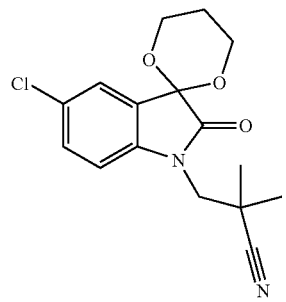

To a stirred solution of potassium t-butoxide (0.561 g, 5.00 mmol, 1.2 eq) in anhydrous DMSO (16 mL) was added 5'-chlorospiro[1,3-dioxane-2,3'-indol]-2'(1'H)-one (1.00 g, 4.17 mmol) all in one portion. After stirring 10 min. 3-chloro-2,2-dimethylpropionitrile (0.981 g, 8.34 mmol, 2 eq) was added in one portion at room temperature under a dry N$_2$ atmosphere. The reaction was heated at 125° C. for 22 hr, cooled to room temperature, poured into H$_2$O (180 mL) and extracted with Et$_2$O (3×). The combined organic extracts were dried over Na$_2$SO$_4$, filtered and concentrated. The crude product was purified on Biotage KP silica gel eluting with 100% CH$_2$Cl$_2$ to give the title compound as a white solid (0.91 g, 68% yield). Anal. Calc'd for $C_{16}H_{17}ClN_2O_3$: C, 59.91; H, 5.34; N, 8.73. Found: C, 59.79;

H, 5.26; N, 8.57. NMR (300 Mz, DMSO-d$_6$): consistent. IR: consistent. MS: (ES+) m/z 321 [M+H]; one Cl pattern observed. m.p.: 114-115.5° C.

Step 3: 8'-Chloro-3',3'-dimethyl-3',4'-dihydro-2'H-spiro[1,3-dioxane-2,10'-pyrimido[1,2-a]indole]

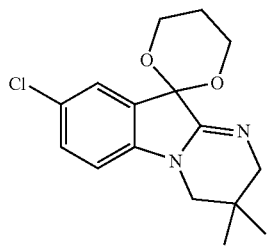

A mixture of 3-(5'-chloro-2'-oxospiro[1,3-dioxane-2,3'-indol]-1'(2'H)-yl)-2,2-dimethylpropanenitrile (0.81 g, 2.53 mmol ), and wet Raney Nickel (0.88 g), in 2M EtOH.NH$_3$ (60 mL) and THF (10 mL) was hydrogenated in a Parr Hydrogenation Bottle (500 mL) at 56 lb/in$^2$ H$_2$ for 17 hr. The Raney Nickel was removed by filtration through Sulka Floc and the filtrate was poured into a steel pressure vessel and heated at 135° C. for 22 hr. The reaction mixture was cooled to room temperature and concentrated. The crude product was purified on Biotage KP silica gel eluting with CH$_2$Cl$_2$/CH$_3$OH/NH$_4$OH, (97/2/1) to give the title compound as an off white solid (0.68 g, 88% yield). Anal. Calc'd for C$_{16}$H$_{19}$ClN$_2$O$_2$: C, 62.64; H, 6.24; N, 9.13. Found: C, 62.59; H, 6.19; N, 9.04. NMR (300 Mz, DMSO-d$_6$): consistent; IR: consistent MS: (ES+) m/z 307 [M+H], one Cl pattern observed; m.p.: 121-122° C.

Step 4: 8'-Chloro-3',3'-dimethyl-3',4'-dihydropyrimido[1,2-a]indol-10(2H)-one

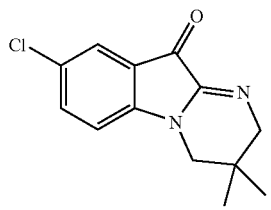

To cold concentrated H$_2$SO$_4$ (5.7 mL) was added 8'-chloro-3',3'-dimethyl-3',4'-dihydro-2'H-spiro[1,3-dioxane-2,10'-pyrimido[1,2-a]indole] (0.558 g, 1.82 mmol ) in ten portions with cooling in an ice bath. The reaction was then allowed to stir at room temperature for 0.5 hr. The reaction was poured onto ice and basified by the drop-wise addition of concentrated NH$_4$OH to pH 11 keeping the temperature cold by cooling in an external ice bath. The reaction mixture was extracted with EtOAc (100 mL). The combined organic extracts were dried over Na$_2$SO$_4$, filtered, concentrated and dried in vacuo at 46° C. to give the title compound as a bright orange crystalline solid (0.301 g, 67% yield). Anal. Calc'd for C$_{13}$H$_{13}$ClN$_2$O+0.1H$_2$O: C, 62.33; H, 5.31; N, 11.18. Found: C, 62.21; H, 5.22; N, 11.05. NMR (400 Mz, DMSO-d$_6$): consistent; IR: consistent. MS: (ES+) m/z 249[M +H]. m.p.: 153-154° C.

Example 15

7-Chloro-8-nitro-3,4-dihydropyrimido[1,2-a]indol-10(2H)-one

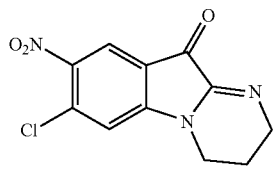

To a cold mixture of 7-chloro-3,4-dihydropyrimido[1,2-a]indole-10(2H)-one (0.221 g, 1.00 mmol ) in concentrated H$_2$SO$_4$ (1 mL), was added fuming nitric acid (0.042 mL, 1.00 mmol ) drop-wise with cooling in a ice/brine bath (−10° C.). After stirring for 10 minutes the ice bath was removed and stirring continued for 1 hour at room temperature. Controlling the temperature with an ice bath, fresh fuming HNO$_3$ (0.021 mL) was added. After stirring for an additional hour the mixture was added to ice and basified with concentrated NH$_4$OH. The resulting yellow solid was filtered, dissolved in CH$_2$Cl$_2$ and filtered again. The filtrate was washed with H$_2$O and the organic layer was separated and concentrated to give the title compound as a bright yellow solid (0.209 g, 79% yield). Anal. Calc'd for C$_{11}$H$_8$ClN$_3$O3+ 0.2H$_2$O: C, 47.60; H, 3.00; N, 14.87. Found: C, 47.58; H, 3.02; N, 14.85. NMR (300 Mz, DMSO-d$_6$): consistent. MS: (ES+) m/z 266 [M+H] one chlorine pattern observed. m.p.: 152-165° C.

Example 16

8-Amino-7-chloro-3,4-dihydropyrimido[1,2-a]indol-10(2H)-one

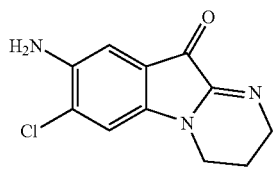

To a suspension of finely ground 7-chloro-8-nitro-3,4-dihydropyrimido[1,2-a]indol-10(2H)-one (0.200 g, 0.753 mmol ) in EtOAc (10 mL) was added SnCl$_2$.2H$_2$O and the mixture was heated at reflux for 1.75 hr after which DMF (2 mL) was added and the reaction proceeded quickly. The reaction was cooled to room temperature and quenched with sat. aq. NaHCO$_3$ (25 mL ). EtOAc (25 mL ) was added and the mixture was stirred for 0.5 hr then filtered. The biphasic layers were separated and the aqueous layer was extracted with EtOAc. The combined organic extracts were dried over Na$_2$SO$_4$, filtered, and concentrated. The crude product was purified on Biotage KP silica gel eluting with CH$_2$Cl$_2$/CH$_3$OH/NH$_4$OH (94/4/2) to give the title compound as a black solid (0.029 g, 16% yield). Anal. Calc'd for C$_{11}$H$_{10}$ClN$_3$O: C, 56.06%, H, 4.28%; N, 17.83%. Found: C, 55.81%; H, 4.17%; N, 17.54%. NMR (300 Mz, DMSO-d$_6$): consistent. MS: (ES−) 238 [M−H]. m.p.>270° C.

Example 17

N-(10-Oxo-2,3,4,10-tetrahydropyrimido[1,2-a]indol-8-yl)benzamide trifluoroacetic acid salt

Step 1: 5'-Nitrospiro[1,3-dioxane-2,3'-indol]-2'(1'H)-one

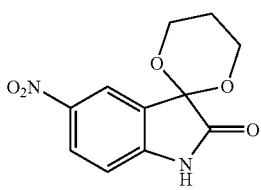

A mixture of 5-nitroisatin (5.00 g, 26.0 mmol), 1,3 propandiol (4.76 mL, 65 mmol, 2.5 eq) and p-toluenesulfonic acid mono-hydrate (0.989 g, 5.2 mmol, 0.2 mol %)) in benzene (500 mL) was refluxed with a Dean Stark Trap for 23 hr. The benzene was decanted off and concentrated. The crude product was purified on Biotage KP silica gel eluting with 50/50 petroleum ether/EtOAc to give the title compound as an off white solid (1.78 g, 27% yield). NMR (300 Mz, DMSO-$d_6$): consistent.

Step 2: 3-(5'-Nitro-2'-oxospiro[1,3-dioxane-2,3'-indol]-1'(2'H)-yl)propanenitrile

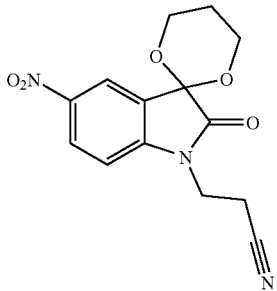

At room temperature, to a mixture of 5'-nitrospiro[1,3-dioxane-2,3'-indol]-2'(1'H)-one(1.75 g, 6.99 mmol) and benzyltrimethylammonium hydroxide (40% aqueous solution, 0.110 mL, 0.699 mmol, 0.1 mole %) in DMF (31 mL) was added acrylonitrile (0.921 mL, 14.0 mmol, 2 eq) drop-wise. and the mixture was heated at 52° C. for 2 hr. The reaction was cooled to room temperature and poured into H$_2$O (160 mL). The reaction mixture was extracted with Et$_2$O. The combined organic extracts were washed with brine and concentrated. The crude product was purified on Biotage KP silica gel eluting with 96/4 CH$_2$Cl$_2$/CH$_3$CN to give the title compound as a yellow solid (2.15 g, 100% ). NMR (300 Mz, DMSO-$d_6$): consistent Step 3: 5'-Amino-1'-(3-aminopropyl)spiro[1.3-dioxane-2.3'-indol]-2'(1'H)-one

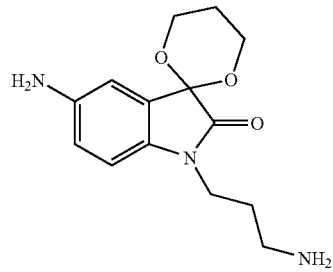

A mixture of 3-(5'-nitro-2'-oxospiro[1,3-dioxane-2,3'-indol]-1'(2'H) -yl)propanenitrile (2.12 g, 7.76 mmol) and wet Raney Nickel (2.29 g) in 2M EtOH.NH$_3$ (95 mL) and THF (35 mL) was hydrogenated in a Parr Hydrogenation Bottle at 50 lb/in$^2$ H$_2$ for 17 hr. The Raney Nickel was removed by filtration through Celite and the filtrate was concentrated. The crude product was purified on Biotage KP silica gel eluting with a step gradient of CH$_2$Cl$_2$/CH$_3$OH/NH$_4$OH (95/3/2) to (85/10/5) to give the title compound as a yellow foam (1.57 g, 73% yield). NMR (300 Mz, DMSO-$d_6$): consistent Step 4: 3',4'-Dihydro-2'H-spiro[1,3-dioxane-2,10'-pyrimido[1,2-a]indol]-8'-amine

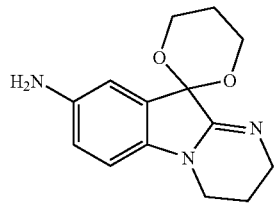

5'-Amino-1'-(3-aminopropyl)spiro[1,3-dioxane-2,3'-indol]-2'(1'H)-one (1.56 g, 5.63 mmol) was dissolved in 2M EtOAc.NH$_3$ (1.90 mL) and THF (10 mL) and heated in a steel pressure vessel at 135° C. for 16 hr. The reaction mixture was cooled to room temperature and combined with silica gel and concentrated. The adsorbate was purified on Biotage KP silica gel eluting with a step gradient of CH$_2$Cl$_2$/CH$_3$OH/NH$_4$OH (95/3/2) to (85/10/5) to give the title compound as a bright yellow-orange solid (1.11 g, 76% yield). NMR (300 Mz, DMSO-$d_6$): consistent.

Step 5: N-3',4'-Dihydro-2'H-spiro[1,3-dioxane-2,10'-pyrimido[1,2-a]indol]-8'-ylbenzamide

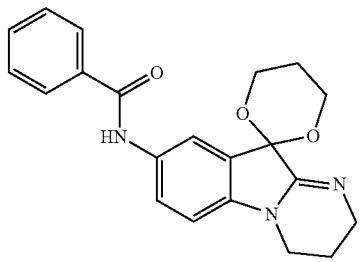

To a cold solution of 3',4'-dihydro-2'H-spiro[1,3-dioxane-2,10'-pyrimido[1,2-a]indol]-8'-amine (0.290 g, 1.44 mmol) and pyridine (0.349 mL, 4.32 mmol, 3 eq) in anhyd. CH$_2$Cl$_2$ (14.4 mL) was added benzoyl chloride (0.200 mL, 1.73 mmol, 1.2 eq) drop-wise with cooling in an ice bath under a dry N$_2$ atmosphere. After stirring 2 hr. at room temperature the reaction was added to water. The reaction mixture was washed with Et$_2$O (3×), basified with 2.5N NaOH and extracted with EtOAc (4×). The combined organic extracts were concentrated. The crude product was purified on Biotage KP silica gel eluting with CH$_2$Cl$_2$/CH$_3$OH/NH$_4$OH (98/1/1) to give the title compound as a yellow solid (0.079 g, 15% yield). NM (300 Mz, DMSO-d$_6$): consistent.

Step 6: N-(10-Oxo-2,3,4,10-tetrahydropyrimido[1,2-a]indol-8-yl)benzamide trifluoroacetic acid salt

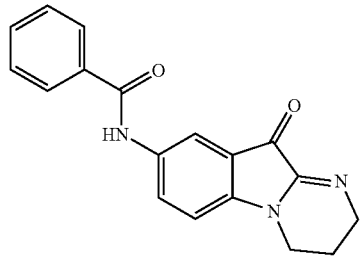

N-3',4'-Dihydro-2'H-spiro[1,3-dioxane-2,10'-pyrimido[1,2-a]indol]-8'-yl]benzamide (0.079 g, 0.217 mmool) was combined with TFA (3 mL) at room temperature under a dry N$_2$ atmosphere. After stirring 4 hr, the mixture was heated at 90° C. for 96 hr and another 8 mL of TFA was added in 2 portions. The reaction was stirred another 72 hr at room temperature then was concentrated to give the title compound as a dark purple solid. Anal. Calc'd for: C$_{18}$H$_{15}$N$_3$O$_2$+2 C$_2$HF$_3$O$_2$: C, 49.08; H, 3.17; N, 7.84. Found: C, 49.54; H, 3.21; N, 7.88. NMR (300 Mz, DMSO-d$_6$): consistent. MS: (API-ESI+) m/z 306 [M+H]. HRMS: consistent. m.p. 155-168° C.

Example 18

8-Fluoro-3,4-dihydropyrimido[1,2-a]indol-10(2H)-one

Step 1: 5-Fluoro-(2-oxospiro[1,3-dioxane-1',3-[3H]-indol]

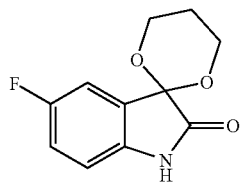

A mixture of 5-fluoroisatin (4.00 g, 24.2 mmol), p-toluenesulfonic acid monohydrate (0.92 g, 4.84 mmol, 0.2 mole %) and 1,3 propanediol (7.0 mL, 96.9 mmol, 4 eq) in benzene (470 mL) was refluxed with a Dean Stark Trap for 9 hr. After cooling to room temperature the mixture was concentrated and the residue was taken up in EtOAc (500 mL), washed with sat. aq. NaHCO$_3$ (3×), combined with silica gel and concentrated. The adsorbate was purified on Biotage KP silica gel eluting with 60/40 Petroleum ether/EtOAc to give the title compound as a light pink solid (3.51 g, 65% yield). Anal. Calc'd for: C$_{11}$H$_{10}$FNO$_3$: C, 59.19; H, 4.52; N, 6.28. Found C, 59.07; H, 4.32; N, 6.37. NMR (300 Mz, DMSO-d$_6$): consistent. MS: (APCI-) m/z 222 [M-H]. m.p.: 165-167° C.

Step 2: 5-Fluoro-2-oxospiro[1,3-dioxane-1',3-[3H]indol]-1-propanenitrile

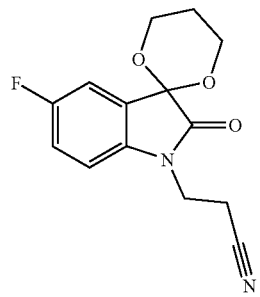

A mixture of 5-fluoro-2-oxospiro[1,3-dioxane-1',3-[3H] indol](3.40 g, 15.2 mmol), benzyltrimethylammonium hydroxide (40% aqueous solution, 0.600 mL, 1.52 mmol, 0.1 mole %) and acrylonitrile (2.00 mL, 30.4 mmol, 2 eq) in DMF (67 mL) was heated at 43° C. for 1 hr. The reaction mixture was cooled to room temperature and poured into H$_2$O (600 mL). The reaction mixture was extracted with Et$_2$O. The combined organic extracts were washed with brine, and concentrated. The crude product was purified on Biotage KP silica gel eluting with 96/4 CH$_2$Cl$_2$/CH$_3$CN to give the title compound as a white crystalline solid (3.50 g, 83% ).

Anal. Calc'd for C$_{14}$H$_{13}$FN$_2$O$_3$: C, 60.87; H, 4.74; N, 10.14. Found: C, 60.75; H, 4.62; N, 10.23. NMR (300 Mz, DMSO-d$_6$): consistent. MS: (APCI+) m/z 277 [M+H]. m.p.: 139-140° C.

Step 3: 1'-(3-Aminopropyl)-5'-fluorospiro[1,3-dioxane-2,3'-indol]-2'(1'H)-one

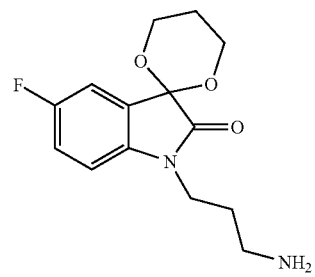

A mixture of 5-fluoro-2-oxospiro[1,3-dioxane-1',3-[3H]-indol]-1-propanenitrile (3.25 g, 11.8 mmol) and wet Raney Nickel (3.02 g), in 2M EtOH.NH$_3$ (250 mL) and THF (50 mL) was hydrogenated in a Parr hydrogenation bottle (500 mL) at 50 lb/in$^2$ H$_2$ for 18 hr. The Raney Nickel was removed by filtration through Sulka Floc and the filtrate was concentrated. The crude product was purified on Biotage KP silica gel eluting with a step gradient CH$_2$Cl$_2$/CH$_3$OH/ NH$_4$OH (96/2/1 to 96/3/2) to give the amine as a white solid (2.57 g, 77% yield).

NMR (300 Mz, DMSO-d$_6$): consistent.

Step 4: 8-Fluoro-10-spiro[(1,3-dioxane)-2',10-(2,3,4, 10-tetrahydropyrimido[1,2-a]indole

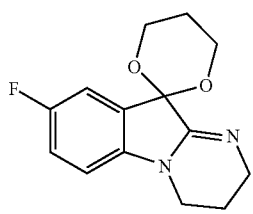

1'-(3-Aminopropyl)-5'-fluorospiro[1,3-dioxane-2,3'-indol]-2'(1'H)-one (2.37 g, 8.46 mmol) was dissolved in 2M EtOH.NH$_3$ (200 mL), poured into a steel pressure vessel, and heated at 135° C. for 46 hr. The reaction mixture was cooled to room temperature and concentrated. The crude product was purified on Biotage KP silica gel eluting with CH$_2$Cl$_2$/CH$_3$OH/NH$_4$OH (97/2/1) followed by a second chromatography eluting with 80/20 Pet ether/acetone to give the title compound as a white solid (1.52 g, 68% yield). Anal. Calc'd for C$_{14}$H$_{15}$FN$_2$O$_2$: C, 64.11; H, 5.76; N, 10.68. Found: C, 64.05; H, 5.79; N, 10.61. NMR (300 Mz, DMSO-d$_6$): consistent; MS: (APCI+) m/z 263 [M+H]. m.p.: 130-132° C.

Step 5: 8-Fluoro-3,4-dihydropyrimido[12-a]indol-10(2H)-one

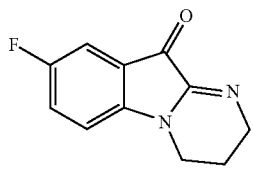

To cold concentrated H$_2$SO$_4$ (13 mL) was added 8-fluoro-10-spiro[(1,3-dioxane)-2',10-(2,3,4,10-tetrahydropyrimido [1,2-a]indole) (1.20 g, 4.60 mmol) in 10 portions over a 17 minute period with cooling in an ice bath. The reaction was stirred at room temperature for 1 hr, poured onto ice and basified with concentrated NH$_4$OH to pH10 keeping the temperature cold with an external ice bath. The resulting red solid was extracted with EtOAc (3×). The combined organic extracts were washed with H$_2$O, dried over Na$_2$SO$_4$, filtered and concentrated. The solid product (0.85 g) was dried in vacuo to give the title compound as a bright red solid (0.613 g, 65% yield). Anal: Calc'd for C$_{11}$H$_9$FN$_2$O: C, 64.70; H, 4.44; N 13.72. Found: C, 64.30; H, 4.34; N 13.77. NMR (300 Mz, DMSO-d$_6$): consistent, IR: consistent. MS: (ACPI+) n/z 205[M+H]. m.p.: 150-152° C.

Example 19

8-Hydroxy-3,4-dihydropyrimido[1,2-a]indol-10 (2H)-one

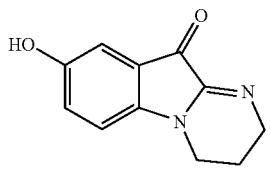

To a cold solution of 8'-methoxy-3',4'-dihydro-2'H-spiro [1,3-dioxane-2,10'pyrimido[1,2-a]indole] (0.723 g, 2.63 mmol) in anhyd. CH$_2$Cl$_2$ (26.4 mL) was added neat boron tribromide (0.80 mL, 8.43 mmol, 3.2 eq) drop-wise via syringe pump over a period of 55 min with cooling to −75° C. in a dry ice/iPrOH bath. The reaction was kept at about −18° C. for 13 hr then poured onto ice and neutralized to pH 7 with concentrated NH$_4$OH keeping the reaction temperature <5° C. The reaction mixture was extracted with EtOAc. The combined organic extracts were dried over Na$_2$SO$_4$ and concentrated. The crude product was combined with the product (0.11 g) from a previous run and triturated with warm EtOAc and filtered to give the title compound as a dark red solid (0.178 g, 33% yield). NMR (300 Mz, DMSO-d$_6$): consistent. MS: (APCI+) 203 [M+H].

m.p.: 265° C. dec.

Example 20

3,3-Dimethyl-10-oxo-2,3,4,10-tetrahydropyrimido[1, 2-a]indole-8-carbonitrile

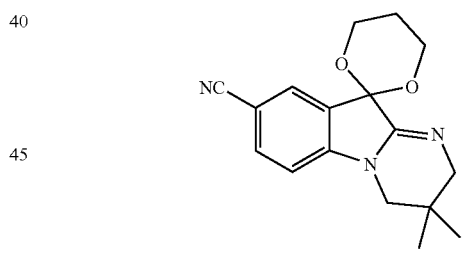

Step 1: 3',3'-dimethyl-3',4'-dihydro-2'H-spiro[1,3-dioxane-2,10'-pyrimido[1,2-a]indole]-8'-carbonitrile At room temperature, nitrogen gas was bubbled into a stirred mixture containing 8'-bromo-3',3'-dimethyl-3',4'-dihydropyrimido[1,2-a]indol-10(2H)-one (0.407 g, 1.16 mmol, prepared as described in Example 14 using 5-bromoisatin in step 1) and copper(I) cyanide (0.208 g, 2.32 mmol) in CH$_3$CN (6 mL) for 10 minutes. To the reaction was added tetrakis(triphenylphosphine)palladium(0) and nitrogen gas was passed through the solution for an additional 10 minutes. The reaction was heated at 80° C. for 1 h, cooled to room temp. and diluted with EtOAc. The reaction was filtered through a Celite pad rinsing with EtOAc. The filtrate was washed with brine (3×), dried (Na$_2$SO$_4$) and concentrated. The crude product was purified on Biotage KP-Sil Step 2: 3,3-Dimethyl-10-oxo-2,3,4,10-tetrahydropyrimido[1,2-a]indole-8-carbonitrile

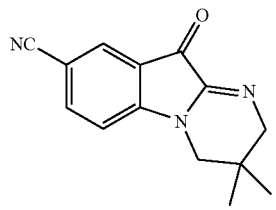

At room temperature a solution containing 3',3'-dimethyl-3',4'-dihydro-2'H-spiro[1,3-dioxane-2,10'-pyrimido[1,2-a]indole]-8'-carbonitrile in methanesulfonic acid was stirred for 1.5 h. The reaction was poured carefully onto crushed ice (100 mL), basified with concentrated NH$_4$OH and extracted with CH$_2$Cl$_2$. The combined organic extracts were washed with H$_2$O (1×), dried (Na$_2$SO$_4$) and purified on Biotage KP-Sil eluting with 40% acetone/hexane to give 0.119 g (94%) of the title compound as a yellow solid. Anal. Calc'd. for C$_{14}$H$_{13}$N$_3$O 0.2H$_2$O: C; 69.23; H, 5.56; N, 17.30. Found: C, 69.59; H, 5.44; N, 17.05. NMR (400 Mz, DMSO-d$_6$): consistent. MS: (ES+) m/z 240 [M+H, 100]. m.p.: 178-184° C.

Example 21

8-({(2S)-2-[(4-Methoxyphenoxy)methyl]pyrrolidin-1-yl}sulfonyl)-3,3-dimethyl-3,4-dihydropyrimido[1,2-a]indol-10(2H)-one Step 1: {(2S)-1-8 (3',3'-Dimethyl-3',4'-dihydro-2'H-spiro[1,3-dioxane-2,10'-pyrimido[1,2-a]indol]-8'-yl)sulfonyl]pyrrolidin-2-yl}methanol

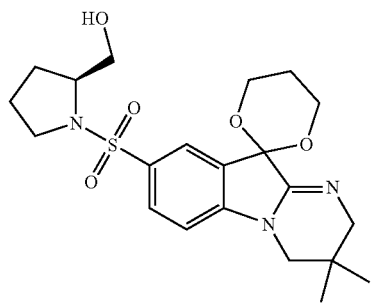

A mixture of 8'-({(2S)-2-[(benzyloxy)methyl]pyrrolidin-1-yl}sulfonyl)-3',3'-dimethyl-3',4'-dihydro-2'H-spiro[1,3-dioxane-2,10'-pyrimido[1,2-a]indole](0.250 g, 0.480 mmol) and 10% Pd/C (0.250 g) in EtOH (10 mL) was degassed for 20 min. and 1,4 cyclohexadiene (5 mL) was added and the mixture was refluxed for 2 days. The reaction was filtered through celite and the filtrate was concentrated. The crude product was purified on Biotage KP silica gel eluting with acetone/hexane (30/70) to give the title compound as a white foam (0.150 g, 72%). Anal: Calc'd for C$_{21}$H$_{29}$N$_3$O$_5$S: C, 57.91; H, 6.71; N, 9.65. Found: C, 57.69; H, 6.7; N, 9.21. NMR (400 Mz, DMSO-d$_6$): consistent. MS: (ESI+) m/z 436.1 [M+H].

Step 2: {(2S)-1-[(3',3'-Dimethyl-3',4'-dihydro-2'H-spiro[1,3-dioxane-2,10'-pyrimido[1,2-a]indol]-8'-yl) sulfonyl]pyrrolidin-2-yl}methyl 4-methylbenzenesulfonate

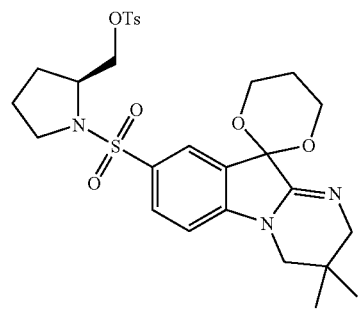

A solution of {(2S)-1-[(3',3'-dimethyl-3',4'-dihydro-2'H-spiro[1,3-dioxane-2,10'-pyrimido[1,2-a]indol]-8'-yl)sulfonyl]pyrrolidin-2-yl}methanol (0.100 g, 2.300 mmol), p-toluenesulfonyl chloride (0.070 g, 0.340 mmol), N,N-diisopropylethylamine (0.100 ml, 0.580 mmol) and 4-(dimethylamino)pyridine (0.020 g, 0.070 mmol) in CH$_2$Cl$_2$ (5 mL) was stirred at rt for 2 days. The reaction was poured into brine and extracted with EtOAc (3×). The combined organic extracts were dried over Na$_2$SO$_4$, filtered and concentrated to give the title compound as a white foam (0.132 g, 97% ). Anal: Calc'd for C$_{28}$H$_{35}$N$_3$O$_7$S$_2$: C, 57.03; H, 5.98; N, 7.13. Found: C, 56.38; H, 5.65; N, 6.81. NMR (400 Mz, DMSO-d$_6$): consistent. MS: (ESI+) m/z 590.3 [M+H].

Step 3: 8-({(2S)-2-[(4-Methoxyphenoxy)methyl] pyrrolidin-1-yl}sulfonyl)-3,3-dimethyl-3,4-dihydropyrimido[1,2-a]indol-10(2H)-one

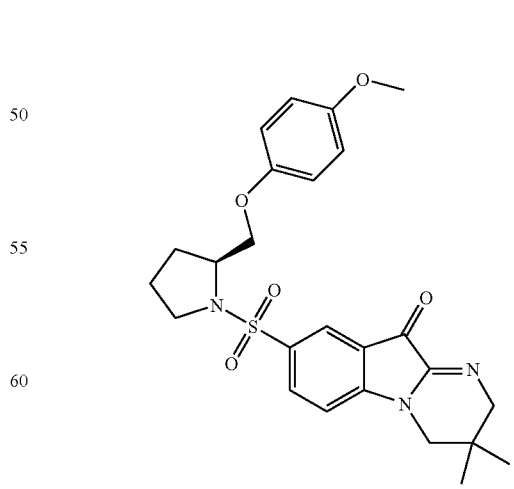

To a solution of 4-methoxy-phenol (0.420 mmol) in THF (3 mL) was added NaH (60% dispersion in mineral oil)

(0.015 g, 0.063 mmol) and the reaction was stirred at rt for 1 hr. {(2S)-1-[(3',3'-Dimethyl-3',4'-dihydro-2'H-spiro[1,3-dioxane-2,10'-pyrimido[1,2-a]indol]-8'-yl)sulfonyl]pyrrolidin-2-yl}methyl 4-methylbenzenesulfonate (0.12 g, 0.21 mmol) in THF (2 mL)/DMF (2 mL) was then added and the reaction heated overnight at 100° C. The reaction was quenched with water and extracted with EtOAc (3×). The combined organic extracts were dried over $Na_2SO_4$, filtered, concentrated and purified on Biotage Si 12+M cartridge silica gel eluting with acetone/hexane (30/70). The resulting product was dissolved in $CH_2Cl_2$ (3 mL) and methanesulfonic acid (2 mL) was added and the solution was stirred at 50° C. overnight. The reaction mixture was poured onto ice, basified to pH 11 with ammonium hydroxide and extracted with EtOAc (3×). The combined organic extracts were dried over $Na_2SO_4$, filtered, concentrated and purified on Biotage Si 12+M cartridge silica gel eluting with acetone/hexane (30/70) to give the title compound as a light yellow foam (0.031 g, 38%). NMR (400 Mz, DMSO-$d_6$): consistent. MS: (ESI+) m/z 484.1 [M+H].

The following compounds were synthesized according to a procedure similar to that of Example 21.

Example 32

8-(2,3-Dihydro-1H-indol-1-ylsulfonyl)-3,3-dimethyl-3,4-dihydropyrimido[1,2-a}indol-10(2H)-one

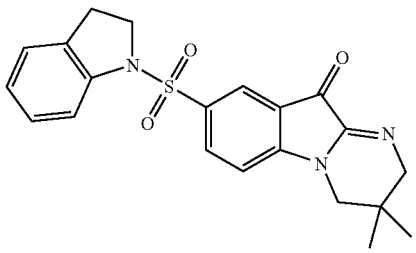

The title compound was prepared as a yellow solid from 2,3-dioxo-2,3-dihydro-1H-indole-5-sulfonylchloride and indoline according to a procedure similar to that of Example 12. NMR (400 Mz, DMSO-$d_6$): consistent. MS: (ES−) m/z 394 [M−H]. m.p.: 169.8-170.8° C.

| Example | Name | $^1$H NMR (400 MHz, DMSO-d6) | MS |
|---|---|---|---|
| 22 | 8-({(2S)-2-[(4-Fluorophenoxy)methyl]pyrrolidin-1-yl}sulfonyl)-3,3-dimethyl-3,4-dihydropyrimido[1,2-a]indol-10(2H)-one | Consistent | MS (ES) m/z 472.2; MS (ES) m/z 504.2; |
| 23 | 8-({(2S)-2-[(4-Chlorophenoxy)methyl]pyrrolidin-1-yl}sulfonyl)-3,3-dimethyl-3,4-dihydropyrimido[1,2-a]indol-10(2H)-one | Consistent | MS (ES) m/z 488.1; MS (ES) m/z 520.2; MS (ES) m/z 975.3; |
| 24 | 3,3-Dimethyl-8-({(2S)-2-[(4-methylphenoxy)methyl]pyrrolidin-1-yl}sulfonyl)-3,4-dihydropyrimido[1,2-a]indol-10(2H)-one | Consistent | MS (ES) m/z 935.4; MS (ES) m/z 468.2; |
| 25 | 8-({(2S)-2-[(2-Chloro-4-methoxyphenoxy)methyl]pyrrolidin-1-yl}sulfonyl)-3,3-dimethyl-3,4-dihydropyrimido[1,2-a]indol-10(2H)-one | Consistent | MS (ES) m/z 516.1; MS (ES) m/z 576.1; |
| 26 | 8-({(2S)-2-[(2-Chloro-4-methylphenoxy)methyl]pyrrolidin-1-yl}sulfonyl)-3,3-dimethyl-3,4-dihydropyrimido[1,2-a]indol-10(2H)-one | Consistent | MS (ES) m/z 502.1; MS (ES) m/z 534.2; |
| 27 | 8-({(2S)-2-[(4-Acetyl-2-methylphenoxy)methyl]pyrrolidin-1-yl}sulfonyl)-3,3-dimethyl-3,4-dihydropyrimido[1,2-a]indol-10(2H)-one | Consistent | MS (ES) m/z 510.1; MS (ES) m/z 542.2; MS (ES) m/z 532.2; |
| 28 | 8-({(2S)-2-[(4-Tert-butylphenoxy)methyl]pyrrolidin-1-yl}sulfonyl)-3,3-dimethyl-3,4-dihydropyrimido[1,2-a]indol-10(2H)-one | Consistent | MS (ES) m/z 508.2; MS (ES) m/z 568.2; |
| 29 | 8-({(2S)-2-[(4-Acetylphenoxy)methyl]pyrrolidin-1-yl}sulfonyl)-3,3-dimethyl-3,4-dihydropyrimido[1,2-a]indol-10(2H)-one | Consistent | MS (ES) m/z 494.1; MS (ES) m/z 554.2; |
| 30 | 8-({(2S)-2-[(4-Fluoro-3-methylphenoxy)methyl]pyrrolidin-1-yl}sulfonyl)-3,3-dimethyl-3,4-dihydropyrimido[1,2-a]indol-10(2H)-one | Consistent | MS (ES) m/z 484.2; MS (ES) m/z 544.2; |
| 31 | 3,3-Dimethyl-8-[((2S)-2-{[3-(trifluoromethyl)phenoxy]methyl}pyrrolidin-1-yl)sulfonyl]-3,4-dihydropyrimido[1,2-a]indol-10(2H)-one | Consistent | MS (ES) m/z 522.1; MS (ES) m/z 554.2; |

Example 33

8-{[(2S)-2-(Methoxymethyl)-2,3-dihydro-1H-indol-1-yl]sulfonyl}-3,3-dimethyl-3,4-dihydropyrimido[1,2-a]indol-10(2H)-one

Step 1: (S)-2-Methoxymethyl-2,3-dihydro-indole-1-carboxylic acid tert-butyl ester

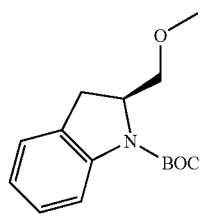

To a slurry of sodium hydride (60%) (1.623 g, 40.5 mmol, 1.3 eq) in THF (15 mL) was added (S)-2-hydroxymethyl-2,3-dihydro-indole-1-carboxylic acid tert-butyl ester (7.760 g, 31.1 mmol, 1 eq) (J. Org. Chem, 62, 7679, 1997) in THF (100 mL) and the mixture was stirred at room temperature for 1 hr. Methyl iodide (3 mL, 48.2 mmol, 1.5 eq) was added and the reaction was stirred at room temperature overnight. It was then poured into brine and extracted with ethyl acetate. The combined organics were washed with brine, dried over magnesium sulfate and concentrated. The crude residue purified by column chromatography using ethyl acetate/hexanes (10/90) as an eluent to give the title compound as a colorless oil (3.863 g, 47%). NMR (400 Mz, DMSO-$d_6$): consistent.

Step 2: (S)-2-Methoxymethyl-2,3-dihydro-1H-indole

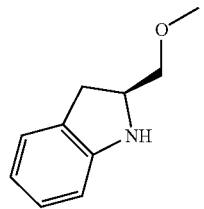

A solution of (S)-2-methoxymethyl-2,3-dihydro-indole-1-carboxylic acid tert-butyl ester (3.863 g, 4.67 mmol, 1 eq) in $CH_2Cl_2$ (50 mL) was cooled to 0° C. and TFA (12 mL) was added. The reaction was stirred at room temperature for 1 hr and then poured carefully into 1 N NaOH. The pH was adjusted to basic with 2.5 N NaOH and it was extracted with $CH_2Cl_2$. The combined organics dried over sodium sulfate and concentrated to afford the title compound as a yellow oil, which was used crude in the following reaction. NMR (400 Mz, DMSO-$d_6$): consistent.

Step 3: 8-{[(2S)-2-(Methoxymethyl)-2,3-dihydro-1H-indol-1-yl]sulfonyl}-3,3-dimethyl-3,4-dihydropyrimido[1,2-a]indol-10(2H)-one

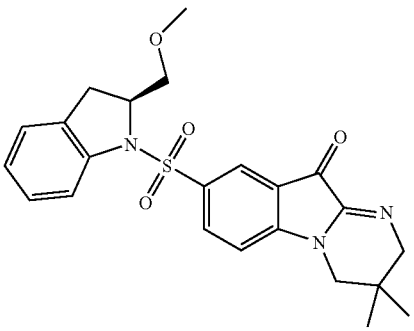

The title compound was prepared from 2,3-dioxo-2,3-dihydro-1H-indole-5-sulfonylchloride and (S)-2-methoxymethyl-2,3-dihydro-1H-indole as a yellow solid according to a procedure similar to that of Example 12. NMR (400 Mz, DMSO-$d_6$): consistent. MS: (ES−) m/z 438 [M−H]. m.p.: 173.4-175.0° C.

Example 34

3,3-Dimethyl-8-{[(2S)-2-(phenoxymethyl)-2,3-dihydro-1H-indol-1-yl]sulfonyl}-3,4-dihydropyrimido[1,2-a]indol-10(2H)-one

Step 1: (S)-2-Phenoxymethyl-2,3-dihydro-indole-1-carboxylic acid tert-butyl ester

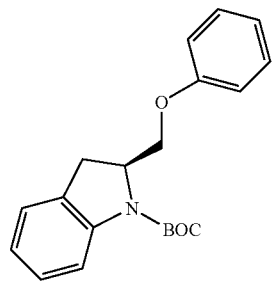

To a solution of phenol (1.715 g, 18.22 mmol, 1.2 eq) in THF (100 mL) was slowly added sodium hydride (0.915 g, 22.87 mmol, 1.5 eq) and the reaction was stirred at rt 1 hour. (S)-2-(Toluene-4-sulfonyloxymethyl)-2,3-dihydro-indole-1-carboxylic acid tert-butyl ester (6.077 g, 15.14 mmol, 1 eq) (J. Org. Chem, 62, 7679, 1997) in THF (50 mL) and DMF (50 mL) were added and the mixture was heated at reflux overnight. After cooling, it was poured into brine and extracted with ethyl acetate. The combined organics were washed with brine, dried over magnesium sulfate and concentrated. The crude residue purified by column chromatography using ethyl acetate/hexanes (15/85) as an eluent to give the title compound as a colorless oil (3.371 g, 74%). NMR (400 Mz, DMSO-$d_6$): consistent Step 2: (S)-2-Phenoxymethyl-2,3-dihydro-1H-indole

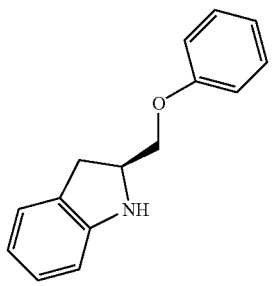

The title compound was prepared from (S)-2-Phenoxymethyl-2,3-dihydro-indole-1-carboxylic acid tert-butyl ester as a colorless oil according to a procedure similar to that of step 2 of Example 25. NMR (400 Mz, DMSO-$d_6$): consistent.

Step 3: 3,3-Dimethyl-8-{[(2S)-2-(phenoxymethyl)-2,3-dihydro-1H-indol-1-yl]sulfonyl}-3,4-dihydropyrimido[1,2-a]indol-10(2H)-one

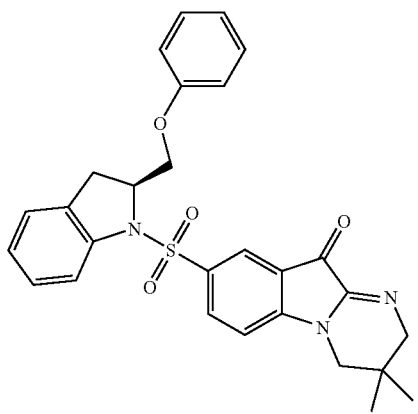

The title compound was prepared from 2,3-dioxo-2,3-dihydro-1H-indole-5-sulfonylchloride and (S)-2-phenoxymethyl-2,3-dihydro-1H-indole as a yellow foam according to a procedure similar to that of Example 12. NMR (400 Mz, DMSO-$d_6$): consistent. MS: (ES−) m/z 500 [M−H].

Example 35

8-[((2S)-2-{[(2-Bromopyridin-3-yl)oxy]methyl}pyrrolidin-1-yl)sulfonyl]-3,3-dimethyl-3,4-dihydropyrimido[1,2-a]indol-10(2H)-one

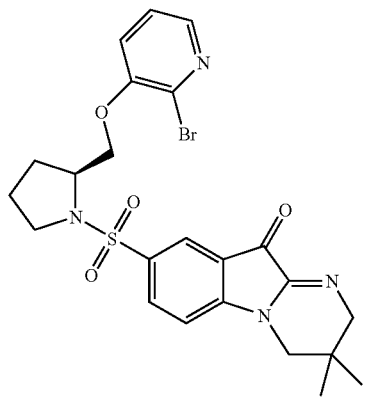

To a solution of 2-bromo pyridinol (0.089 g, 0.510 mmol) in THF (3 mL) was added NaH (60% dispersion in mineral oil) (0.020 g, 0.085 mmol) and the reaction was stirred at rt for 1 hr. {(2S)-1-[(3',3'-Dimethyl-3',4'-dihydro-2'H-spiro[1,3-dioxane-2,10'-pyrimido[1,2-a]indol]-8'-yl)sulfonyl]pyrrolidin-2-yl}methyl 4-methylbenzenesulfonate (0.100 g, 0.170 mmol) in THF (2 mL)/DMF (2 mL) was added and the reaction was heated overnight at 100° C. The reaction was quenched with water and extracted with EtOAc (3×). The combined organic extracts were dried over $Na_2SO_4$, filtered, concentrated and purified on Biotage Si 12+M cartridge silica gel eluting with acetone/hexane (30/70). The resulting product was dissolved in $CH_2Cl_2$ (3 mL) and methanesulfonic acid (2 mL) was added and the solution stirred at 35° C. overnight. The reaction mixture was poured onto ice, basified to pH 11 with ammonium hydroxide and extracted with EtOAc (3×). The combined organic extracts were dried over $Na_2SO_4$, filtered, concentrated and purified on Biotage Si 12+M cartridge silica gel eluting with acetone/hexane (30/70) to give the title compound as a yellow foam (0.058 g, 56%). NMR (400 Mz, DMSO-$d_6$): consistent. MS: (ESI+) m/z 533.1 [M+H].

The following compounds were synthesized according to a procedure similar to that of Example 35.

| Example | Name | 1H NMR (400 MHz, DMSO-d6) | MS |
|---|---|---|---|
| 38 | 3,3-Dimethyl-8-({(2S)-2-[(pyridin-2-yloxy)methyl]pyrrolidin-1-yl}sulfonyl)-3,4-dihydropyrimido[1,2-a]indol-10(2H)-one | Consistent | MS (ES) m/z 455.2; MS (ES) m/z 477.2; MS (ES) m/z 909.5; |
| 39 | 8-[((2S)-2-{[(5-Chloropyridin-2-yl)oxy]methyl}pyrrolidin-1-yl)sulfonyl]-3,3-dimethyl-3,4-dihydropyrimido[1,2-a]indol-10(2H)-one | Consistent | MS (ES) m/z 487.1; MS (ES) m/z 547.2; |
| 40 | 8-[((2S)-2-{[(6-Chloropyridin-2-yl)oxy]methyl}pyrrolidin-1-yl)sulfonyl]-3,3-dimethyl-3,4-dihydropyrimido[1,2-a]indol-10(2H)-one | Consistent | MS (ES) m/z 489.2; MS (ES) m/z 521.2; |
| 41 | 3,3-Dimethyl-8-[((2S)-2-{[(6-methylpyridin-2-yl)oxy]methyl}pyrrolidin-1-yl)sulfonyl]-3,4-dihydropyrimido[1,2-a]indol-10(2H)-one | Consistent | MS (ES) m/z 469.2; MS (ES) m/z 501.2; |

-continued

| Example | Name | $^1$H NMR (400 MHz, DMSO-d6) | MS |
|---|---|---|---|
| 42 | 3,3-Dimethyl-8-{[(2S)-2-({[5-(trifluoromethyl)pyridin-2-yl]oxy}methyl)pyrrolidin-1-yl]sulfonyl}-3,4-dihydropyrimido[1,2-a]indol-10(2H)-one | Consistent | MS (ES) m/z 521.2; MS (ES) m/z 581.2; |
| 43 | 8-[((2S)-2-{[(2-Chloropyridin-3-yl)oxy]methyl}pyrrolidin-1-yl)sulfonyl]-3,3-dimethyl-3,4-dihydropyrimido[1,2-a]indol-10(2H)-one | Consistent | MS (ES) m/z 487.1; MS (ES) m/z 547.1; |
| 44 | 3,3-Dimethyl-8-[((2S)-2-{[(6-methylpyridin-3-yl)oxy]methyl}pyrrolidin-1-yl)sulfonyl]-3,4-dihydropyrimido[1,2-a]indol-10(2H)-one | Consistent | MS (ES) m/z 469.2; MS (ES) m/z 501.2; MS (ES) m/z 937.4; |
| 45 | Methyl 5-({(2S)-1-[(3,3-dimethyl-10-oxo 2,3,4,10-tetrahydropyrimido[1,2-a]indol-8-yl)sulfonyl]pyrrolidin-2-yl}methoxy)nicotinate | Consistent | MS (ES) m/z 513.2; MS (ES) m/z 545.2; |
| 46 | 8-[((2S)-2-{[(2-Iodo-6-methylpyridin-3-yl)oxy]methyl}pyrrolidin-1-yl)sulfonyl]-3,3-dimethyl-3,4-dihydropyrimido[1,2-a]indol-10(2H)-one | Consistent | MS (ES) m/z 595.1; MS (ES) m/z 627.1; |
| 47 | 3,3-Dimethyl-8-({(2S)-2-[(pyridin-3-yloxy)methyl]pyrrolidin-1-yl}sulfonyl)-3,4-dihydropyrimido[1,2-a]indol-10(2H)-one | Consistent | MS (ES) m/z 453.1; MS (ES) m/z 513.2; |
| 48 | 8-[((2S)-2-{[(5-Chloropyridin-3-yl)oxy]methyl}pyrrolidin-1-yl)sulfonyl]-3,3-dimethyl-3,4-dihydropyrimido[1,2-a]indol-10(2H)-one | Consistent | MS (ES) m/z 487.1; MS (ES) m/z 547.1; |
| 49 | 3,3-Dimethyl-8-[((2S)-2-{[(2-methylpyridin-3-yl)oxy]methyl}pyrrolidin-1-yl)sulfonyl]-3,4-dihydropyrimido[1,2-a]indol-10(2H)-one | Consistent | MS (ES) m/z 468.2; MS (ES) m/z 937.4; MS (ES) m/z 501.2; |
| 73 | 3,3-Dimethyl-8-({(2S)-2-[(pyridin-2-yloxy)methyl]pyrrolidin-1-yl}sulfonyl)-3,4-dihydropyrimido[1,2-a]indol-10(2H)-one | Consistent | MS (ES) m/z 455.2 |

Example 36

8-({(2S)-2-[(Cyclohexylamino)methyl]pyrrolidin-1-yl}sulfonyl)-3,3-dimethyl-3,4-dihydropyrimido[1,2-a]indol-10(2H)-one

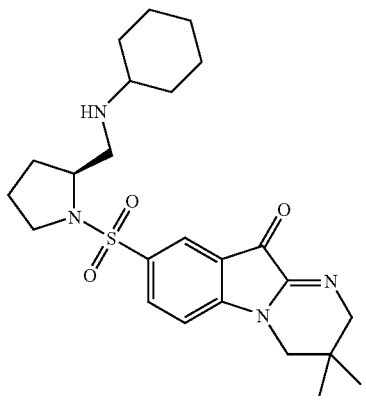

To a solution of {(2S)-1-[(3',3'-dimethyl-3',4'-dihydro-2'H-spiro[1,3-dioxane-2,10'-pyrimido[1,2-a]indol]-8'-yl)sulfonyl]pyrrolidin-2-yl}methyl 4-methylbenzenesulfonate (0.100 g, 0.170 mmol) in THF (2 mL) was added cyclohexylamine (0.034 g, 0.340 mmol) and the reaction was stirred at 70° C. overnight. Additional cyclohexylamine (0.088 g, 0.850 mmol) was added to the reaction and stirred at 100° C. for 2 days. The reaction was quenched with water and extracted with EtOAc (3×). The combined organic extracts were dried over Na$_2$SO$_4$, filtered, concentrated and purified on Biotage Si 12+M cartridge silica gel eluting with acetone/hexane (35/65). The resulting product was dissolved in CH$_2$Cl$_2$ (2 mL) and methanesulfonic acid (2 mL) was added and the solution was stirred at rt overnight. The reaction mixture was poured onto ice, basified to pH 11 with ammonium hydroxide and extracted with EtOAc (3×). The combined organic extracts were dried over Na$_2$SO$_4$, filtered, concentrated and purified on Biotage Si 12+M cartridge silica gel eluting with acetone/hexane (35/65) to give the title compound as a yellow foam (0.036 g, 46%). NMR (400 Mz, DMSO-d$_6$): consistent. MS: (ESI+) m/z 459.3 [M+H].

The following compounds were synthesized according to a procedure similar to that of Example 36.

| Example | Name | $^1$H NMR (400 MHz, DMSO-d6) | MS |
|---|---|---|---|
| 63 | 3,3-Dimethyl-8-{[(2S)-2-(morpholin-4-ylmethyl)pyrrolidin-1-yl]sulfonyl}-3,4-dihydropyrimido[1,2-a]indol-10(2H)-one | Consistent | MS (ES) m/z 445.2; MS (ES) m/z 505.2; |

-continued

| Example | Name | ¹H NMR (400 MHz, DMSO-d6) | MS |
|---|---|---|---|
| 64 | Ethyl 4-({(2S)-1-[(3,3-dimethyl-10-oxo-2,3,4,10-tetrahydropyrimido[1,2-a]indol-8-yl)sulfonyl]pyrrolidin-2-yl}methyl)piperazine-1-carboxylate | Consistent | MS (ES) m/z 518.2; MS (ES) m/z 540.2; MS (ES) m/z 550.3; |
| 65 | 8-({(2S)-2-[(Cyclopentylamino)methyl]pyrrolidin-1-yl}sulfonyl)-3,3-dimethyl-3,4-dihydropyrimido[1,2-a]indol-10(2H)-one | Consistent | MS (ES) m/z 445.3 |
| 74 | 3,3-Dimethyl-8-({(2S)-2-[(4-methylpiperazin-1-yl)methyl]pyrrolidin-1-yl}sulfonyl)-3,4-dihydropyrimido[1,2-a]indol-10(2H)-one | Consistent | MS (ES) m/z 460.2 |

Example 37

N-(3,3-Dimethyl-10-oxo-2,3,4,10-tetrahydropyrimido[1,2-a]indol-8-yl)benesulfonamide Step 13-(5'-Nitro-2'-oxospiro[1,3-dioxane-2,3'-indol]-1'(2'H)-yl)-2,2-dimethylpropanenitrile

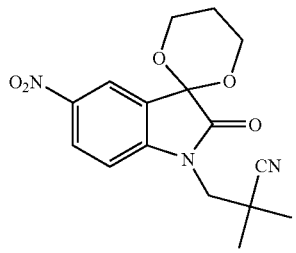

The title compound was prepared from 5'-nitrospiro[1,3-dioxane-2,3'-indol]-2'(1'H)-one and 3-chloro-2,2-dimethyl-propionitrile following a procedure to that of Step 2 of Example 14. NMR (400 Mz, DMSO-d₆): consistent.

Step 2: 3',3'-Dimethyl-3',4'-dihydro-2'H-spiro[1,3-dioxane-2,10'-pyrimido[1,2-a]-8' amine

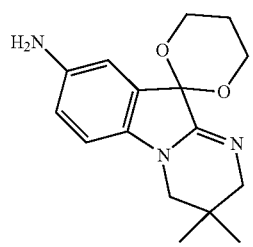

The title compound was prepared from 3-(5'-nitro-2'-oxospiro[1,3-dioxane-2,3'-indol]-1'(2'H)-yl)-2,2-dimethyl-propanenitrile following a procedure similar to that of steps 3 and 4 of Example 17. NMR (400 Mz, DMSO-d₆): consistent.

Step 3: N-(3',3'-Dimethyl-3', 4'-dihydro-2'H-spiro[1,3-dioxane-2,10'-pyrimido[1,2-a]indol]-8'-yl)benzenesulfonamide

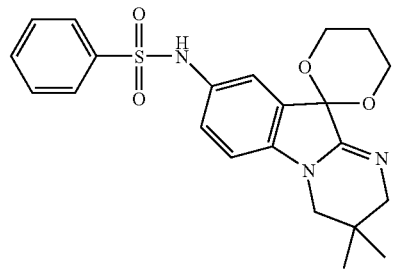

To a solution of 3',3'-dimethyl-3',4'-dihydro-2'H-spiro[1,3-dioxane-2,10'-pyrimido[1,2-a]indol]-8'amine (0.060 g 0.21 mmol, 1 eq) in CH₂Cl₂ (2 mL) was added Et₃N (0.060 mL, 0.43 mmol, 2.05 eq) and benzenesulfonyl chloride (0.030 mL, 0.23 mmol, 1.07 eq). The reaction was stirred at rt 1 hour and concentrated. The crude residue purified by column chromatography using acetone/hexanes (30/70) as an eluent to give the title compound as a white solid (0.064 g, 71%). NMR (400 Mz, DMSO-d₆): consistent Step 4: N-(3,3-Dimethyl-10-oxo-2,3,4,10-tetrahydropyrimido[1,2-a]indol-8-yl)benzenesulfonamide

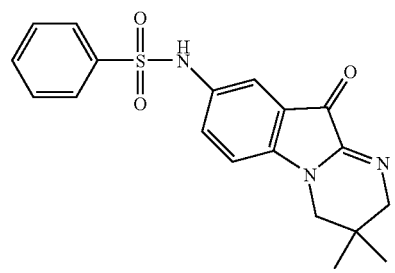

To a solution of N-(3',3'-dimethyl-3',4'-dihydro-2'H-spiro[1,3-dioxane-2,10'-pyrimido[1,2-a]indol]-8'-yl)benzenesulfonamide (0.064 g, 0.14 mmol, 1 eq) in CH₂Cl₂ (4 mL) was added methanesulfonic acid (2 mL). The reaction was stirred at rt overnight and then poured into brine. It was basified to pH 10, saturated with solid NaCl, and extracted with EtOAc. The combined organics were dried over sodium sulfate and concentrated. The crude residue purified by column chromatography using acetone/hexanes (40/60) as an eluent to give the title compound as a yellow foam (0.032 g, 58%). NMR (400 Mz, DMSO-$d_6$): consistent. MS: (ES−) m/z 368 [M−H].

The following compounds were prepared according to a procedure similar to that of Example 37.

| Example | Name | $^1$H NMR DMSO-$d_6$ (400 MHz) | MS |
|---|---|---|---|
| 50 | 3-Bromo-N-(3,3-dimethyl-10-oxo-2,3,4,10-tetrahydropyrimido[1,2-a]indol-8-yl)benzenesulfonamide | Consistent | MS (APPI) m/z 448; MS (APPI) m/z 480; |
| 51 | N-(3,3-Dimethyl-10-oxo-2,3,4,10-tetrahydropyrimido[1,2-a]indol-8-yl)-4-methylbenzenesulfonamide | Consistent | MS (APPI) m/z 384; MS (APPI) m/z 416; |
| 52 | 3-Chloro-N-(3,3-dimethyl-10-oxo-2,3,4,10-tetrahydropyrimido[1,2-a]indol-8-yl)-4-fluorobenzenesulfonamide | Consistent | MS (APPI) m/z 422; MS (APPI) m/z 454; |
| 53 | 3,4-Dichloro-N-(3,3-dimethyl-10-oxo-2,3,4,10-tetrahydropyrimido[1,2-a]indol-8-yl)benzenesulfonamide | Consistent | MS (APPI) m/z 438; MS (APPI) m/z 470; |
| 54 | N-(3,3-Dimethyl-10-oxo-2,3,4,10-tetrahydropyrimido[1,2-a]indol-8-yl)-3-(trifluoromethyl) benzenesulfonamide | Consistent | MS(APPI) m/z 438; MS (APPI) m/z 470; |
| 55 | N-(3,3-Dimethyl-10-oxo-2,3,4,10-tetrahydropyrimido[1,2-a]indol-8-yl)-2-fluorobenzenesulfonamide | Consistent | MS (APPI) m/z 388; MS (APPI) m/z 420; |
| 56 | N-(3,3-Dimethyl-10-oxo-2,3,4,10-tetrahydropyrimido[1,2-a]indol-8-yl)-4-methoxybenzenesulfonamide | Consistent | MS (APPI) m/z 400; MS (APPI) m/z 432; |
| 57 | N-(3,3-Dimethyl-10-oxo-2,3,4,10-tetrahydropyrimido[1,2-a]indol-8-yl)-4-fluorobenzenesulfonamide | Consistent | MS (APPI) m/z 388; |
| 58 | 4-Chloro-N-(3,3-dimethyl-10-oxo-2,3,4,10-tetrahydropyrimido[1,2-a]indol-8-yl)benzenesulfonamide | Consistent | MS (APPI) m/z 404; |
| 59 | 2-Bromo-N-(3,3-dimethyl-10-oxo-2,3,4,10-tetrahydropyrimido[1,2-a]indol-8-yl)benzenesulfonamide | Consistent | MS (APPI) m/z 448; MS (APPI) m/z 480; |
| 60 | N-(3,3-Dimethyl-10-oxo-2,3,4,10-tetrahydropyrimido[1,2-a]indol-8-yl)-3-methoxybenzenesulfonamide | Consistent | MS (APPI) m/z 400; MS (APPI) m/z 432; |
| 61 | N-(3,3-Dimethyl-10-oxo-2,3,4,10-tetrahydropyrimido[1,2-a]indol-8-yl)-4-(trifluoromethoxy)benzenesulfonamide | Consistent | MS (APPI) m/z 454; |
| 62 | N-(3,3-Dimethyl-10-oxo-2,3,4,10-tetrahydropyrimido[1,2-a]indol-8-yl)-3,5-bis(trifluoromethyl)benzenesulfonamide | Consistent | MS (APPI) m/z 506; MS (APPI) m/z 538; |

Example 66

3,3-Dimethyl-8-{[(2S)-2-(phenoxymethyl)pyrrolidin-1-yl]carbonyl}-3,4-dihydropyrimido[1,2-a]indol-10(2H)-one Step 1: 8'-Bromo-3',3'-dimethyl-3',4'-dihydro-2'H-spiro[1,3-dioxane-2,10'-pyrimido[1,2-a]indole]

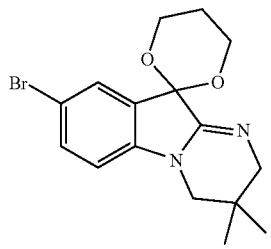

The title compound was synthesized from 5'-bromospiro[1,3-dioxane-2,3'-indol]-2'(1'H)-one following a procedure similar to that described in steps 1 and 2 of Example 4 to give the title compound as light brown solid (0.290 g, 85%). Anal: Calc'd for $C_{16}H_{19}BrN_2O_2$: C, 54.71; H, 5.45; N, 7.98. Found: C, 54.93; H, 5.30; N, 7.88. NMR (400 Mz, DMSO-$d_6$): consistent. MS: (EI) m/z 350[M−H]. m.p.: 128-129° C.

Step 2: 3',3'-Dimethyl-8'-vinyl-3',4'-dihydro-2'H-spiro[1,3-dioxane-2,10'-pyrimido[1,2-a]indole]

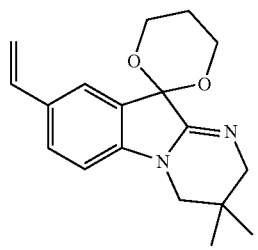

To the stirred solution of 8'-bromo-3',3'-dimethyl-3',4'-dihydro-2'H-spiro[1,3-dioxane-2,10'-pyrimido[1,2-a]indole](2.576 g, 7.330 mmol) in dioxane (70 mL) was added tributyl (vinyl) tin (3.490 g, 10.995 mmol) and the solution was degassed with N$_2$ for 15 min. Pd(PPh$_3$)$_4$ was added and the mixture was stirred at 100° C. for 6 hr. The reaction was diluted with EtOAc, washed with brine and concentrated. The resulting residue was dissolved in EtOAc and stirred with 1M KF solution (20 mL) overnight. The reaction was filtered and the filtrate was washed with brine. The organics were dried over Na$_2$SO$_4$ and concentrated to give the title compound as white solid (1.720 g, 79%). NMR (400 Mz, DMSO-d$_6$): consistent.

Step 3: Methyl 3',3'-dimethyl-3',4'-dihydro-2'H-spiro[1,3-dioxane-2,10'-pyrimido[1,2a]indole]-8'-carboxylate

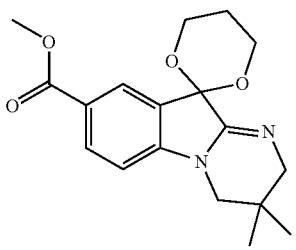

To the solution of 3',3'-dimethyl-8'-vinyl-3',4'-dihydro-2'H-spiro[1,3-dioxane]-2,10'-pyrimido[1,2-a]indole](0.687 g, 2.303 mmol) in CH$_2$Cl$_2$ (15 mL), was added 2.5N NaOH (7.5 mL) and MeOH (7.5 mL) and the solution was cooled to −60° C. A stream of O$_3$ was bubbled into the reaction for 15 minutes until TLC indicated starting material was consumed. H$_2$O (20 mL) was then added to the reaction and it was extracted with EtOAc. The combined organics were dried over Na$_2$SO$_4$, filtered and concentrated to give the title compound as a white solid (0.41 g, 54%). NMR (400 Mz, DMSO-d$_6$): consistent.

Step 4: 3',3'-Dimethyl-3',4'-dihydro-2'H-spiro[1,3-dioxane-2,10'-pyrimido[1,2-a]indole]-8'-carboxylic acid

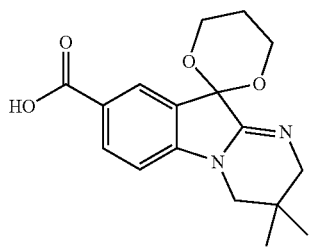

To a solution of methyl 3',3'-dimethyl-3',4'-dihydro-2'H-spiro[1,3-dioxane-2,10'-pyrimido[1,2-a]indole]-8'-carboxylate (0.200 g, 0.610 mmol) in THF (4 mL)/EtOH (4 mL) was added 1N NaOH (2 mL) and H$_2$O (2 mL) and the reaction was refluxed for 1 hr. The reaction was quenched with 1 N HCl and extracted with EtOAc (3×). The combined organic extracts were dried over Na$_2$SO$_4$, filtered and concentrated to give the title compound as white solid (0.097 g, 50%). NMR (400 Mz, DMSO-d$_6$): consistent. MS (ES+) m/z 317.3 [M+H]. m.p.: 151.1-153.3° C.

Step 5: 3,3-Dimethyl-8-{[(2S)-2-(phenoxymethyl)pyrrolidin-1-yl]carbonyl}-3,4-dihydropyrimido[1,2-a]indol-10(2H)-one

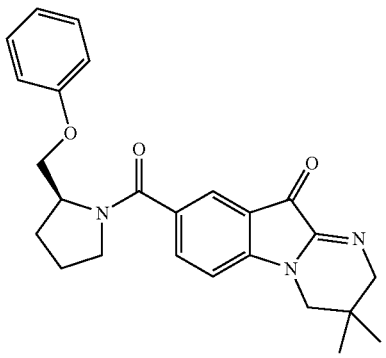

To a solution of 3',3'-dimethyl-3',4'-dihydro-2'H-spiro[1,3-dioxane-2,10'-pyrimido[1,2-a]indole]-8'-carboxylic acid (0.090 g, 0.284 mmol) in CH$_2$Cl$_2$ (7 mL) was added (2S)-2-(phenoxymethyl)pyrrolidine (0.75 g, 0.427 mmol), DCC (0.082 g, 0.039 mmol), HOBT (0.038 g, 0.281 mmol) and Et$_3$N (0.045 mL, 0.277 mmol) and the solution stirred overnight at rt. The reaction was filtered through 1 cm of silica gel washing with EtOAc. The filtrate was dried over Na$_2$SO$_4$, filtered, concentrated and purified on silica gel eluting with acetone/hexane (30/70). The resulting white foam was dissolved in CH$_2$Cl$_2$ (1.5 mL) and methanesulfonic acid (1 mL) was added and the solution was stirred at rt overnight. The reaction was poured onto ice, basified to pH 11 with ammonium hydroxide and extracted with EtOAc (3×). The combined organic extracts were dried over Na$_2$SO$_4$, filtered, concentrated and purified on Biotage Si 12+M cartridge silica gel eluting with acetone/hexane (35/65) to give the title compound as a yellow foam (0.021 g, 20%). NMR (400 Mz, DMSO-d$_6$): consistent. MS (ES+) m/z 418.3 [M+H].

The following examples were synthesized according to a procedure similar to that of Example 66.

| Example | Name | ¹H NMR (400 MHz, DMSO-d6) | MS |
|---|---|---|---|
| 75 | 8-{[(2S)-2-(Methoxymethyl)pyrrolidin-1-yl]carbonyl}-3,3-dimethyl-3,4-dihydropyrimido[1,2-a]indol-10(2H)-one | Consistent | MS (ES) m/z 356.2; MS (ES) m/z 388.2; MS (ES) m/z 419.2; |
| 76 | 3,3-Dimethyl-10-oxo-N-phenyl-2,3,4,10-tetrahydropyrimido[1,2-a]indole-8-carboxamide | Consistent | MS (ES) m/z 332.2; |
| 77 | N-Cyclopentyl-3,3-dimethyl-10-oxo-2,3,4,10-tetrahydropyrimido[1,2-a]indole-8-carboxamide | Consistent | MS (ES) m/z 326.2; |
| 78 | 3,3-Dimethyl-8-(pyrrolidin-1-ylcarbonyl)-3,4-dihydropyrimido[1,2-a]indol-10(2H)-one | Consistent | MS (ES) m/z 312.2; MS (ES) m/z 375.2; MS (ES) m/z 623.4; MS (ES) m/z 645.3; |
| 79 | 3,3-Dimethyl-8-(piperidin-1-ylcarbonyl)-3,4-dihydropyrimido[1,2-a]indol-10(2H)-one | Consistent | MS (ES) m/z 326.2; MS (ES) m/z 389.2; |
| 80 | 8-(2,3-Dihydro-1H-indol-1-ylcarbonyl)-3,3-dimethyl-3,4-dihydropyrimido[1,2-a]indol-10(2H)-one | Consistent | MS (ES) m/z 360.2; |
| 81 | 3,3-Dimethyl-8-[(4-methylpiperazin-1-yl)carbonyl]-3,4-dihydropyrimido[1,2-a]indol-10(2H)-one | Consistent | MS (ES) m/z 341.2; |
| 82 | 8-[(4-Acetylpiperazin-1-yl)carbonyl]-3,3-dimethyl-3,4-dihydropyrimido[1,2-a]indol-10(2H)-one | Consistent | MS (ES) m/z 369.2; |

Example 67

8'-{[(2S)-2-(Methoxymethyl)pyrrolidin-1-yl]sulfonyl}spiro[cyclopentane-1,3'-pyrimido[1,2-a]indol]-10'(2'H)-one

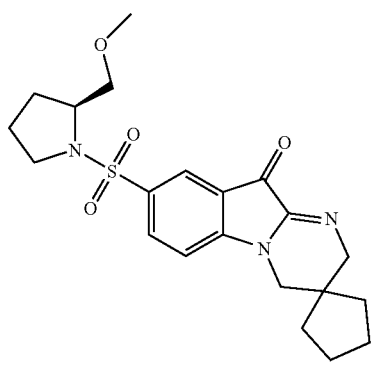

The title compound was prepared as a yellow solid from 5'-{[(2S)-2-(methoxymethyl)pyrrolidin-1-yl]sulfonyl}spiro[1,3-dioxane-2,3'-indol]-2'(1'H)-one and 1-chloromethyl-cyclopentanecarbonitrile (Syn. Comm. 20(12) 1757, 1990) using a procedure similar to that of steps 3-5 of Example 12. NMR (400 Mz, DMSO-d₆): consistent. MS: (ES−) m/z 416[M−H]. m.p.: 171.2-171.9° C.

Example 68

8'-{[(2S)-2-(Methoxymethyl)pyrrolidin-1-yl]sulfonyl}spiro[cyclohexane-1,3'-pyrimido[1,2-a]indol]-10'(2'H)-one

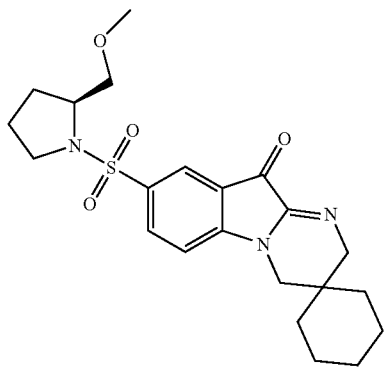

The title compound was prepared as a yellow foam from 5'-{[(2S)-2-(methoxymethyl)pyrrolidin-1-yl]sulfonyl}spiro[1,3-dioxane-2,3'-indol]-2'(1'H)-one and 1-chloromethyl-cyclohexanecarbonitrile (Syn. Comm. 20(12) 1757, 1990) using a procedure similar to that of steps 3-5 of Example 12. NMR (400 Mz, DMSO-d₆): consistent. MS: (ES−) m/z 430 [M−H].

Example 69

8'-{[(2S)-2-(Methoxymethyl)pyrrolidin-1-yl]sulfonyl}spiro[cyclobutane-1,3'-pyrimido[1,2-a]indol]-10'(2'H)-one

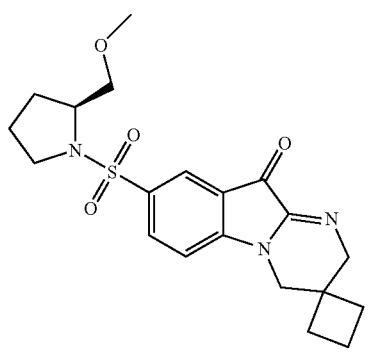

The title compound was prepared as a yellow solid from 5'-{[(2S)-2-(methoxymethyl)pyrrolidin-1-yl]sulfonyl}spiro[1,3-dioxane-2,3'-indol]-2'(1'H)-one and 1-chloromethyl-cyclobutanecarbonitrile (*Syn. Comm.* 20(12) 1757, 1990) using a procedure similar to that of steps 3-5 of Example 12. NMR (400 Mz, DMSO-$d_6$): consistent. MS: (ES−) m/z 402 [M−H]. m.p.: 146.8.8-147.4° C.

Example 70

8'-{[(2S)-2-(Phenoxymethyl)pyrrolidin-1-yl]sulfonyl}spiro[cyclopentane-1,3'-pyrimido[1,2-a]indol]-10'(2'H)-one

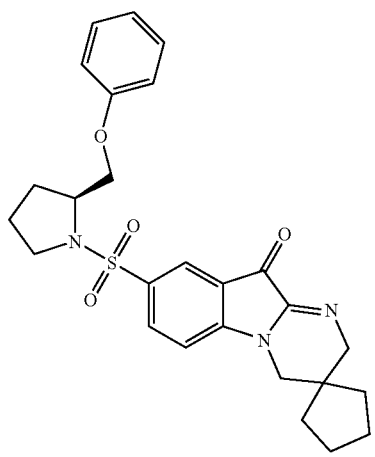

The title compound was prepared as a yellow solid from 5'-{[(2S)-2-(phenoxymethyl)pyrrolidin-1-yl]sulfonyl}spiro[1,3-dioxane-2,3'-indol]-2'(1'H)-one and 1-chloromethyl-cyclopentanecarbonitrile (*Syn. Comm.* 20(12) 1757, 1990) using a procedure similar to that of steps 3-5 of Example 12. NMR (400 Mz, DMSO-$d_6$): consistent. MS: (ES−) m/z 478 [M−H]. m.p.: 142.9.8-144.5° C.

Example 71

8'-{[(2S)-2-(Phenoxymethyl)pyrrolidin-1-yl]sulfonyl}spiro[cyclohexane-1,3'-pyrimido[1,2-a]indol]-10'(2'H)-one

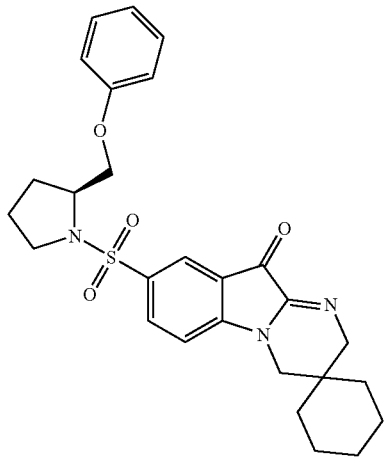

The title compound was prepared as a yellow foam from 5'-{[(2S)-2-(phenoxymethyl)pyrrolidin-1-yl]sulfonyl}spiro[1,3-dioxane-2,3'-indol]-2'(1'H)-one and 1-chloromethyl-cyclohexanecarbonitrile (*Syn. Comm.* 20(12) 1757, 1990) using a procedure similar to that of steps 3-5 of Example 12. NMR (400 Mz, DMSO-$d_6$): consistent. MS: (ES−) m/z 492 [M−H]

Example 72

8'-{[(2S)-2-(Phenoxymethyl)pyrrolidin-1-yl]sulfonyl}spiro[cyclobutane-1,3'-pyrimido[1,2-a]indol]-10'(2'H)-one

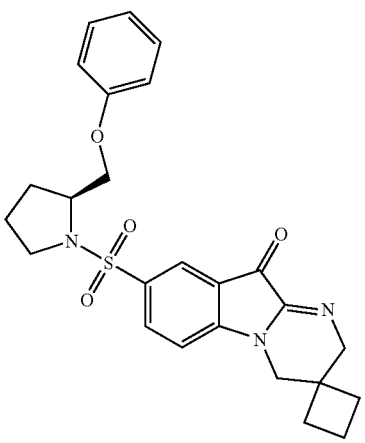

The title compound was prepared as a yellow foam from 5'-{[(2S)-2-(phenoxymethyl)pyrrolidin-1-yl]sulfonyl}spiro[1,3-dioxane-2,3'-indol]-2'(1'H)-one and 1-chloromethyl-cyclobutanecarbonitrile (*Syn. Comm.* 20(12) 1757, 1990) using a procedure similar to that of steps 3-5 of Example 12. NMR (400 Mz, DMSO-$d_6$): consistent. MS: (ES−) m/z 464 [M−H].

Example 83

8'-{[(2S)-2-(morpholin-4-ylmethyl)pyrrolidin-1-yl]sulfonyl}spiro[cyclopentane-1,3'-pyrimido[1,2-a]indol]-10'(2'H)-one Step 1: 5-{[(2S)-2-(morpholin-4-ylmethyl)pyrrolidin-1-yl]sulfonyl}-1H-indole-2,3-dione

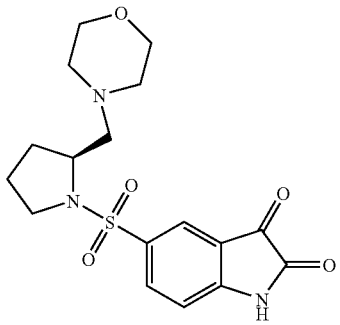

The title compound was prepared as a yellow foam from 2,3-dioxo-2,3-dihydro-1H-indole-5-sulfonylchloride and 4-(S)-1-pyrrolidin-2-ylmethyl-morpholine (*Tetrahedron*, 43(14), 3289, 1987) according to a procedure similar to that of step 1 of Example 12. NMR (400 Mz, DMSO-$d_6$): consistent. MS: (ES−) m/z 378 [M−H].

Step 2: 8'-{[(2S)-2-(morpholin-4-ylmethyl)pyrrolidin-1-yl]sulfonyl}spiro[cyclopentane-1,3'-pyrimido[1,2-a]indol]-10'(2'H)-one

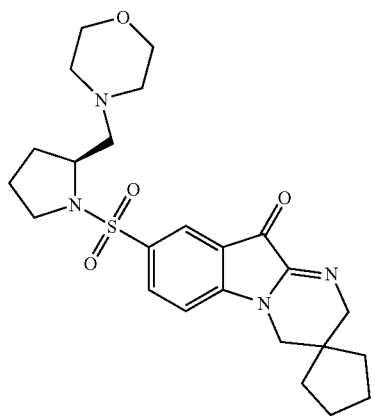

The title compound was prepared as a orange solid from 5-{[(2S)-2-(morpholin-4-ylmethyl)pyrrolidin-1-yl]sulfonyl}-1H-indole-2,3-dione and 1-chloromethyl-cyclopentanecarbonitrile (*Syn. Comm.* 20(12) 1757, 1990) using a procedure similar to that of steps 3-5 of Example 12. NMR (400 Mz, DMSO-$d_6$): consistent. MS: (ES−) m/z 471 [M−H]. m.p.: 162.9-163.6° C.

Example 84

8'-({(2S)-2-[(4-Methylpiperazin-1-yl)methyl]pyrrolidin-1-yl}sulfonyl)spiro[cyclopentane-1,3'-pyrimido[1,2-a]indol]-10'(2'H)-one Step 1: 1-Methyl-4-({(2S)-1-[(4-methylphenyl)sulfonyl]pyrrolidin-2-yl}methyl)piperazine

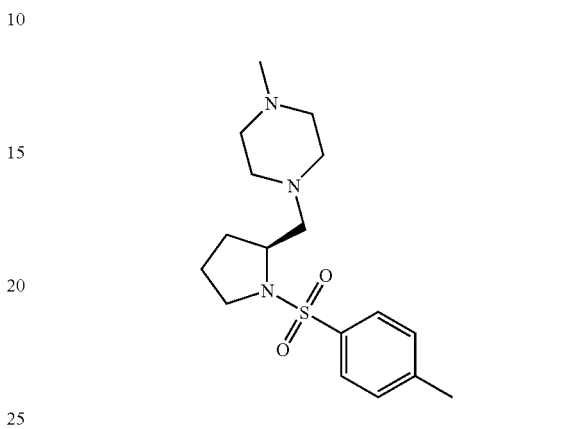

To a solution of {(2S)-1-[(4-methylphenyl)sulfonyl]pyrrolidin-2-yl}methyl 4-methylbenzenesulfonate (9.427 g, 23.13 mmol) (*Tetrahedron*, 43(14), 3289, 1987) in toluene (150 mL), was added n-methyl-piperazine (12.8 mL, 115.65 mmol) and DBU (0.352 g, 2.313 mmol) and the solution was stirred at 140° C. overnight. The reaction was then diluted with ether and washed with brine. The organic layer was dried over $Na_2SO_4$, filtered, concentrated and purified on Biotage flash 40M cartridge silica gel eluting with $CH_2Cl_2$/$CH_3OH$/$NH_4OH$ (95.5/3/1.5) to give an off white solid (2.570 g, 55%). NMR (400 Mz, DMSO-$d_6$): consistent. MS (ES+) m/z 338.1 [M+H]. m.p.: 96.5-97.7° C. Reference: (*Tetrahedron*, 43(14), 3289, 1987).

Step 2: 1-Methyl-4-[(2S)-pyrrolidin-2-ylmethyl]piperazine

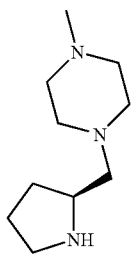

To a flame dried 3 neck 250 mL round bottom flask fitted with dry ice condenser, ammonia (50 mL) was condensed at −78° C. using an acetone bath. 1-Methyl-4-({(2S)-1-[(4-methylphenyl)sulfonyl]pyrrolidin-2-yl}methyl)piperazine (2.562 g, 7.790 mmol) dissolved in THF (40 mL), EtOH (2 mL) and $NH_3$ (40 mL) was transferred via syringe into the reaction vessel. Lithium (0.500 g, 72.000 mmol) was added by small pieces into the stirred solution. Acetone bath was then removed and the reaction was allowed to reflux for 2 hours and then warmed up to rt. The reaction was quenched with $H_2O$ (50 mL) basified to pH 11 with ammonium hydroxide and extracted with EtOAc (3×). The aqueous layer was re-extracted with CH₂Cl₂/MeOH (90/10) and the combined organic extracts were dried over Na₂SO₄, filtered and concentrated to give the title compound as a yellow oil (1.300 g, 93% ). NMR (400 Mz, DMSO-d₆): consistent. Reference: (*Tetrahedron,* 43(14), 3289, 1987).

Step 3: 5-({(2S)-2-[(4-methylpiperazin-1-yl)methyl]pyrrolidin-1-yl}sulfonyl)-1H-indole-2,3-dione

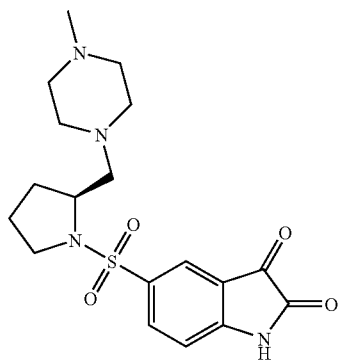

The title compound was prepared from 2,3-dioxo-2,3-dihydro-1H-indole-5-sulfonylchloride and 1-methyl-4-[(2S)-pyrrolidin-2-ylmethyl]piperazine according to a procedure similar to that of step 1 of Example 12. NMR (400 Mz, DMSO-d₆): consistent.

Step 4: 8'-({(2S)-2-[(4-Methylpiperazin-1-yl)methyl]pyrrolidin-1-yl}sulfonyl)spiro[cyclopentane-1,3'-pyrimido[1,2-a]indol]-10'(2'H)-one

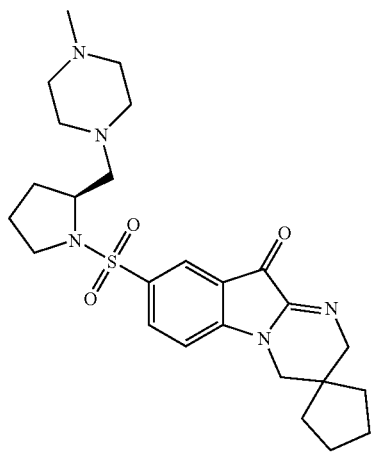

The title compound was prepared as a light brown foam from 5-({(2S)-2-[(4-methylpiperazin-1-yl)methyl]pyrrolidin-1-yl}sulfonyl)-1H-indole-2,3-dione and 1-(chloromethyl)cyclopentanecarbonitrile (*Syn. Comm.* 20(12) 1757, 1990), using a procedure similar to that of steps 2-5 of Example 12. NMR (400 Mz, DMSO-d₆): consistent. MS: (ES+) m/z 486.2 [M+H].

Example 85: 8'-{[(2S)-2-(methoxymethyl)pyrrolidin-1-yl]sulfonyl}spiro[cycloheptane-1,3'-pyrimido[1,2-a]indol]-10'(2'H)-one Step 1: 5'-{[(2S)-2-(methoxymethyl)pyrrolidin-1-yl]sulfonyl}spiro[1,3-dioxolane-2,3'-indol]-2'(1'H)-one

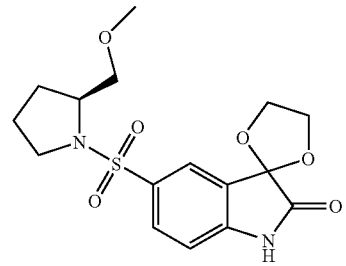

A mixture of 5'-{[(2S)-2-(methoxymethyl)pyrrolidin-1-yl]sulfonyl }-1H-indole-2,3-dione (1.5 g, 4.6 mmol, 1 eq) (previously described in Step 2, Example 1), ethylene glycol (1.14 g, 18.4 mmol, 4 eq) and p-toluenesulfonic acid (0.35 g, 1.8 mmol) in benzene (32 mL) was refluxed for 2 hours. Water removal was accomplished using a Dean Stark Trap. After 2 hours, an additional portion of ethylene glycol (1.14 g, 18.4 mmol, 4 eq) was added and reflux was continued for an additional 4 hours. The reaction mixture was then cooled to room temperature, washed with saturated aqueous NaHCO3, water and brine. The organic layer was dried over sodium sulfate, filtered and concentrated. The residue was purified by flash chromatography on silica gel using EtOAc/hexane (1:1) to give the title compound as a white solid (1.40 g, 83% yield). NMR (400 MHz, DMSO-d6): consistent. MS: (ES–) m/z 367 [M–H].

Step 2: 8'-{[(2S)-2-(methoxymethyl)pyrrolidin-1-yl]sulfonyl}spiro[cycloheptane-1,3'-pyrimido[1,2-a]indol]-10'(2'H)-one

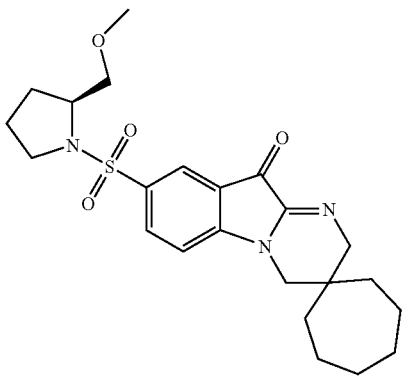

The title compound was prepared as a yellow foam from 5'-{[(2S)-2-(methoxymethyl)pyrrolidin-1-yl]sulfonyl}spiro[1,3-dioxolane-2,3'-indol]-2'(1'H)-one and 1-chloromethyl-cycloheptanecarbonitrile (*Syn. Comm.* 20(12) 1757, 1990) using a procedure similar to that of steps 3-5 of Example 12. The crude product was purified on Biotage KP silica gel eluting with CH₂Cl₂/EtOAc (9:1). NMR (400 Mz, DMSO-d₆): consistent. Analytical HPLC (Chromolith Monolith 0.46×10 cm column, gradient of acetonitrile in water/trifluoroacetic acid): 93.2% (254 nm). MS: (API-ES⁺) m/z 446.2 [M+H]; (API-ES⁻) m/z 444.2 [M−H].

Example 86

8'-{[(2S)-2-(methoxymethyl)pyrrolidin-1-yl]sulfonyl}spiro[cycloheptane-1,3'-pyrimido[1,2-a]indol]-10'(2'H)-one As an alternative to the reaction described in Example 85, the title compound can also be prepared as described below.

Step 1: 5'-{[(2S)-2-(methoxymethyl)pyrrolidin-1-yl]sulfonyl}spiro[1,3-dioxolane-2,3'-indol]-2'(1'H)-one

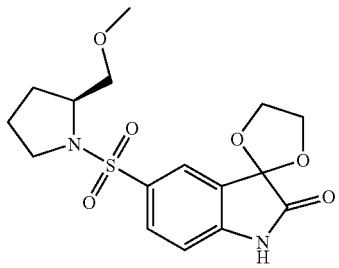

A mixture of 5'-{[(2S)-2-(methoxymethyl)pyrrolidin-1-yl]sulfonyl}-1H-indole-2,3-dione (1.5 g, 4.6 mmol, 1 eq) (previously described in Step 2, Example 1), ethylene glycol (1.14 g, 18.4 mmol, 4 eq) and p-toluenesulfonic acid (0.35 g, 1.8 mmol) in benzene (32 mL) was refluxed for 2 hours. Water removal was accomplished using a Dean Stark Trap. After 2 hours, an additional portion of ethylene glycol (1.14 g, 18.4 mmol, 4 eq) was added and reflux was continued for an additional 4 hours. The reaction mixture was then cooled to room temperature, washed with saturated aqueous NaHCO3, water and brine. The organic layer was dried over sodium sulfate, filtered and concentrated. The residue was purified by flash chromatography on silica gel using EtOAc/hexane (1:1) to give the title compound as a white solid (1.40 g, 83% yield). NMR (400 MHz, DMSO-d₆): consistent. MS: (ES⁻) m/z 367 [M−H].

Step 2: 1-{[2'-oxo-5'-{[(2S)-2-(methoxyoxymethyl)pyrrolidin-1-yl]sulfonyl}spiro[1,3-dioxolane-2,3'-indol]-1'(2'H)-yl]methyl}cycloheptanecarbonitrile

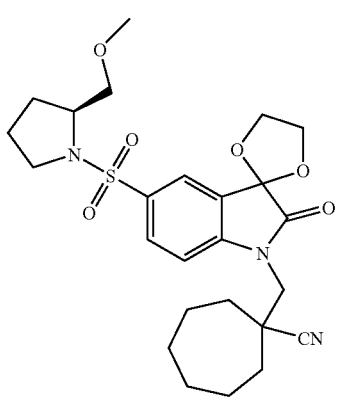

To a solution of 5'-{[(2S)-2-(methoxymethyl)pyrrolidin-1-yl]sulfonyl}spiro[1,3-dioxolane-2,3'-indol]-2'(1'H)-one (1.0 g, 2.71 mmol, 1 eq) in anhydrous DMSO (25 mL) under a nitrogen atmosphere was added potassium tert-buboxide (0.39 g, 3.52 mmol, 1.3 eq). The resulting mixture was stirred at room temperature for one hour and then treated with a solution of 1-chloromethyl-cyclohyptanecarbonitrile (1.2 g, 6.78 mmol, 2.5 eq) (*Syn Commun.* 20(12) 1757, 1990) in anhydrous DMSO (3 mL). The resulting reaction mixture was heated in an oil bath at 185° C. for 18 hours. After cooling to room temperature, water (50 mL) was added and the resulting mixture was stirred for 5 minutes and then extracted with EtOAc (3×50 mL). The combined organic layers were dried over sodium sulfate, filtered and concentrated. The resulting residue was purified by chromatography on Biotage KP flash silica gel eluting with hexane/EtOAc (7:3) to give the title compound as an off-white solid (0.39 g, 28% yield). NMR (500 MHz, DMSO-d₆): consistent. MS (API-ES⁺) m/z 504 [M+H].

Step 3: 1-{[2'-oxo-5'-{[(2S)-2-(methoxyoxymethyl)pyrrolidin-1-yl]sulfonyl}spiro[1,3-dioxolane-2,3'-indol]-1'(2'H)-yl]methyl}-1-(aminomethyl)-cycloheptane

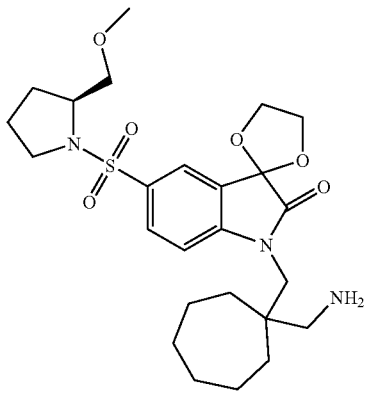

A mixture of 1-{[2'-oxo-5'-{[(2S)-2-(methoxyoxymethyl)pyrrolidin-1-yl]sulfonyl}spiro[1,3-dioxolane-2,3'-indol]-1'(2'H)-yl]methyl}cycloheptanecarbonitrile (0.37 g, 0.74 mmol, 1 eq) and Raney Nickel (0.4 g) in 2N ammonia/EtOH (30 mL) was treated with hydrogen gas at 50 p.s.i. on a Parr Shaker Apparatus for 18 hours. The mixture was filtered to remove the catalyst. The catalyst was washed with 2N ammonia/EtOH and the combined filtrates were concentrated to yield the title compound as an oil (0.25 g, 68% yield). NMR (500 MHz, DMSO-d₆): consistent. MS (API-ES⁺) m/z 508 [M+H].

Step 4: 8'-{[(2S)-2-(methoxymethyl)pyrrolidin-1-yl]sulfonyl}-2'H-dispiro[cycloheptane-1,3'-pyrimido[1,2-a]indole-10',2"-[1,3]dioxolane]

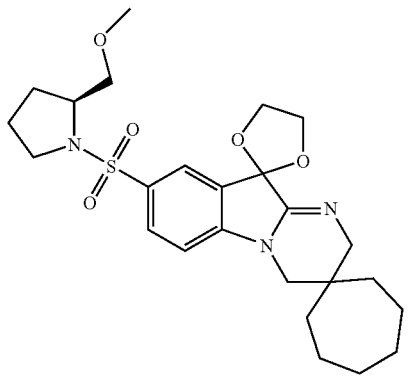

A solution of 1-{[2'-oxo-5'-{[(2S)-2-(methoxyoxymethyl)pyrrolidin-1-yl]sulfonyl}spiro[1,3-dioxolane-2,3'-indol]-1'(2'H)-yl]methyl}-1-(aminomethyl)-cycloheptane (0.25 g, 0.49 mmol, 1 eq) in 2N ammonia/EtOH (5 mL) was heated in a sealed tube at 130° C. for 4 hours. After cooling, the mixture was concentrated and the residue was purified by chromatography on Biotage KP silica gel eluting with hexane/acetone (3:1) to give the title compound as an off-white solid (0.14 g, 58% yield). NMR (500 MHz, DMSO-d$_6$): consistent. MS (API-ES$^+$) m/z 490 [M+H].

Step 5: 8-{[(2S)-2-(methoxymethyl)pyrrolidin-1-yl]sulfonyl}spiro[cycloheptane-1,3-pyrimido[1,2-a]indol]-10'(2'H)-one

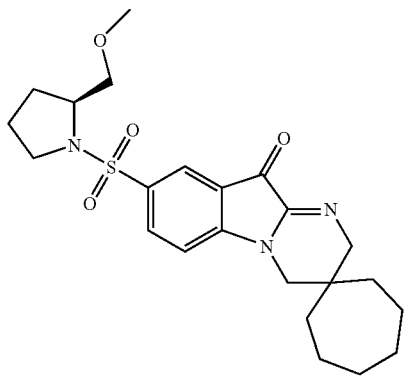

A solution of 8'-{[(2S)-2-(methoxymethyl)pyrrolidin-1-yl]sulfonyl}-2'H-dispiro[cycloheptane-1,3'-pyrimido[1,2-a]indole-10',2"-[1,3]dioxolane (0.13 g, 0.27 mmol) in CH$_2$Cl$_2$ (2 mL) was treated with methanesulfonic acid (1.5 mL) and then stirred at 50° C. for 18 hours. After cooling, the mixture was washed with water (5 mL). The aqueous layer was extracted with CH$_2$Cl$_2$ (5 mL) and the combined organic layers were washed with saturated aqueous NaHCO$_3$, dried over sodium sulfate, filtered and concentrated. The residue was purified by chromatography on Biotage KP silica gel eluting with CH$_2$Cl$_2$/EtOAc (9:1) to give the title compound as a yellow foam (0.02 g, 17% yield). NMR (400 Mz, DMSO-d$_6$): consistent. Analytical HPLC (Chromolith Monolith 0.46×10 cm column, gradient of acetonitrile in water/trifluoroacetic acid): 93.2% (254 nm). MS: (API-ES$^+$) m/z 446.2 [M+H]; (API-ES$^-$) m/z 444.2 [M−H].

Example 87

2-Methyl-8-(pyrrolidin-1-ylsulfony)-3,4-dihydropyrimido[1,2-a'indol-10 (2H)-one

Step 1: 3-[5'-{[pyrrolidin-1-yl]sulfonyl}-2'-oxospiro[1,3-dioxane-2.3'-indol]-1'(2'H)-yl]-2-bromo-butane

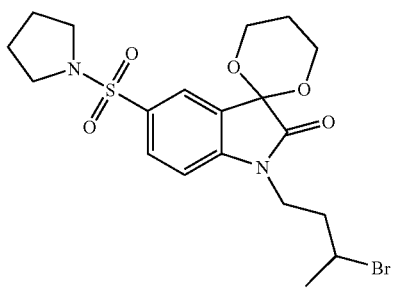

To a solution of potassium t-butoxide (0.12 g, 1 mmol, 1 eq) in anhydrous DMSO (5 mL) at room temperature under dry N$_2$ atmosphere was added 5'-{[pyrrolidin-1-yl]sulfonyl}spiro[1,3-dioxane-2,3'-indol]-2'(1'H)-one (previously described in step 2, Example 12) (0.33 g, 1 mmol). After stirring for 10 minutes, 1,3-dibromobutane (0.22 g, 1 mmol, 1 eq) was added dropwise to the reaction over a 5 minute period. The reaction mixture was stirred at room temperature for one hour. The mixture was poured into H$_2$O (20 ml) and exhaustively extracted with EtOAc. The combined organic extracts were dried over Na$_2$SO$_4$, filtered and concentrated. The crude product was purified by flash chromatography on silica gel using 30% EtOAc/hexane to give the title compound as an off white solid (0.23 g, 50% yield). NMR (400 MHz, DMSO-d$_6$): consistent. MS: (API-ES$^+$) m/z 474 [M+H].

Step 2: 3-[5'-{[pyrrolidin-1-yl]sulfonyl}-2'-oxospiro]1,3-dioxane-2,3'-indol]-1'(2'H)-yl]-2-azidobutane

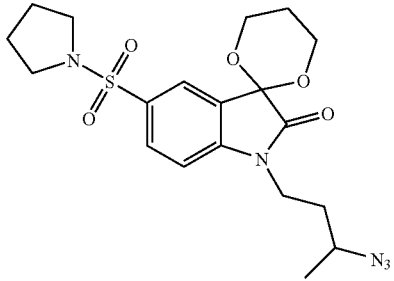

A mixture of 3-[5'-{[pyrrolidin-1-yl]sulfonyl}-2'-oxospiro[1,3-dioxane-2,3'-indol]-1'(2'H)-yl]-2-bromobutane (0.23 g, 0.48 mmoles) and sodium azide (0.04 g, 0.58 mmoles, 1.2 eq) in DMSO (5 ml) was heated at 80° C. for 2 hours. The reaction mixture was cooled to room temperature, diluted with EtOAc, washed with H$_2$O (3×), dried over Na$_2$SO$_4$, filtered and concentrated. The crude product was purified by flash chromatography on silica gel using 40% EtOAc/hexane to give the title compound as an off white solid (0.16 g, 78% yield). NMR (400 MHz, DMSO-d$_6$): consistent. MS: (API-ES$^+$) m/z 436 [M+H].

Step 3: 3-[5'-{[pyrrolidin-1-yl]sulfonyl}-2'-oxospiro [1,3-dioxane-2,3'-indol]-1'(2'H)-yl]-2-aminobutane

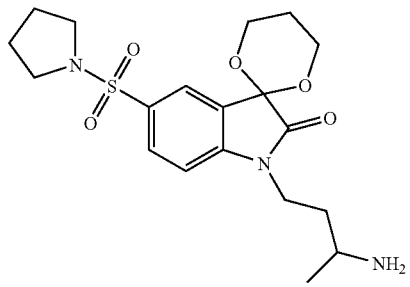

A mixture of 3-[5'-{[pyrrolidin-1-yl]sulfonyl}-2'-oxospiro[1,3-dioxane-2,3'-indol]-1'(2'H)-yl]-2-azidobutane (0.16 g, 0.37 mmoles) and 10% Pd/C in methanol (5 ml) was stirred under a H$_2$ atmosphere (1 atmosphere) overnight at room temperature. The reaction mixture was filtered, and concentrated. The crude product was purified by flash chromatography on silica gel using 40% EtOAc/hexane followed by 1% CH$_3$OH/EtOAc to give the title compound as an off white solid (0.06 g, 40% yield). NMR (400 MHz, DMSO-d$_6$): consistent. MS: (API-ES$^+$) m/z 410 [M+H].

Step 4: 2'-Methyl-8'-(pyrrolidin-1-ylsulfonyl)-3',4'-dihydro-2'H-spiro[1,3-dioxane-2,10'-pyrimido[1,2-a]indole]

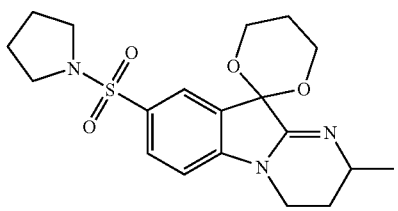

A mixture of 3-[5'-{[pyrrolidin-1-yl]sulfonyl}-2'-oxospiro[1,3-dioxane-2.3'-indol]-1'(2'H)-yl]-2-aminobutane (0.06 g, 0.15 mmoles) and NH$_3$ in EtOH (3 ml ) was stirred in the microwave at 160° C. for 4 hours. The reaction mixture was concentrated and the crude product was purified by flash chromatography on silica gel using 50% EtOAc/hexane to give the title compound as an off-white solid (0.045 g, 78% yield). NMR (400 MHz, DMSO-d$_6$): consistent. MS: (API-ES$^+$) m/z 392 [M+H].

Step 5: 2-Methyl-8-(pyrrolidin-1-ylsulfony)-3,4-dihydropyrimido [1,2-a'indol-10(2H)-one

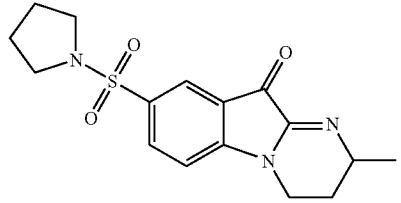

A mixture of 2'-methyl-8'-(pyrrolidin-1-ylsulfonyl)-3',4'-dihydro-2'H-spiro[1,3-dioxane-2,10'-pyrimido[1,2-a]indole] (0.045 g, 0.11 mmoles), 1 mL CH$_3$SO$_3$H and 1 mL of CH$_2$Cl$_2$ was stirred at room temperature overnight. The reaction mixture was diluted with EtOAc, washed with H20 (1×), brine (1×), dried over Na$_2$SO$_4$ and concentrated. The resulting residue was recrystallized from CH$_2$Cl$_2$/hexane to give the title compound as an off-white solid (0.027 g, 75% yield). NMR (400 MHz, DMSO-d$_6$): consistent. MS: (API-ES$^+$) m/z 334 [M+H], m.p. 152.5-153° C.

Example 88

Preparation of Active Caspase 3

Caspase 3 was expressed intracellularly in E. coli with a c-terminal His tag. Fermentation was performed at 25° C. in a B. Braun Biotech Biostat C 10 liter bioreactor vessel. The culture was collected in 1L bottles and centrifuged in Komspin KA-7.1000 rotors at approximately 8000 RCF (Relative Centrifugal Force). The cell pellets were re-suspended in 20 mM Tris pH 8.0, 500 mM NaCl, and 5 mM imidazole. The cell suspension was disrupted by passing 5 times through a microfluidizer Model 110Y (Microfluidics Corp, Newton, Mass). After centrifugation (13 kg, 30 min at 4 C), the supernatant was applied to a column of Nickle-NTA agarose. The Caspase 3 was eluted with a gradient of 5 mM to 150 mM imidazole in the above buffer. Fractions containing Caspase 3 were pooled and concentrated with a Millipore Ultrafree filtration device. The concentrated Caspase 3 solution was loaded unto a TSK gel G3000sw column (Tosoh Bioseph LLC), equilibrated with a buffer of 20 mM PIPES pH 7.2, 100 mM NaCl, 1 mM EDTA & 5 mM Cysteine. Fractions containing Caspase 3 were pooled and concentrated. Sometimes CHAPS was added to 0.1% and sucrose to 10% into the protein sample. The Caspase 3 obtained with this method shows two subunits of 17 and 13 kD on reduced SDS-PAGE and aliquots stored at −80° C.

Example 89

Caspase 3 Inhibition Assay

This standard pharmacological test procedure to assess the inhibition of recombinant caspase 3 activity of selected compounds was adapted from Thornbery, N. A., et al., J. Biol. Chem. 1997 272(29) 17907-17911 and Stennicke, H. R. et al., J. Biol. Chem. 1997 272(41) 25719-25723. The procedure used and results obtained are briefly described below.

Caspase 3 was assayed at 23° C. (room temp) in 96-well plates using the internally quenched tetrapeptide substrate N-acetyl-aspartyl-glutamyl-valyl-aspartate-7-amino-4-trifluoromethyl coumarin (Ac-DEVD-AFC purchased from Biomol). The assays are conducted at pH 7.2 in a buffered system containing 20 mM PIPES, 100 mM NaCl, 1 mM EDTA, 0.1% CHAPS, 10% sucrose and 5 mM L-cysteine. The final concentration of the substrate is 25 µM. Enzymic cleavage between the aspartate and the AFC fluorophore liberates 7-amino-4-trifluoromethyl coumarin which is detected using an excitation wavelength of 400 nm and an emission wavelength of 505 nm in a SpectraMax GeminiXS plate reader operated at room temperature. A steady state rate of substrate cleavage is obtained for analysis.

For $IC_{50}$ determination, typically 11 concentrations ranging from 20 uM to 20 nM were prepared serial dilution with assay buffer containing no cysteine with 80 ul of 31.25 uM substrate added to the assay well. Once substrate and inhibitor were added to the assay plate, the reaction was initiated by addition of 10 ul of 2.5 nM enzyme, prepared in assay buffer containing 50 mM Cysteine, to the assay mixture (final concentration 0.25 nM). After the reaction was initiated with the addition of enzyme, AFC production was monitored continuously for 90 minutes by exciting at 400 nm and measuring the emission at 505 nm every 42 seconds. The progress curves generated were fitted by computer to equation 1 to generate an IC50 value. Equation 1: $y=Bmax*(1-(x''/(K''+x'')))$, where Bmax is rate in the absence of inhibitor.

If only one concentration of inhibitor was tested or the $IC_{50}$ was greater than the highest concentration of compound used in the assay, the percent inhibition at the highest compound concentration is reported. Based on the calculations above the following results were obtained.

| Example | $IC_{50}$ (µM) |
| --- | --- |
| 1 | 0.027 |
| 2 | 0.007 |
| 4 | 0.006 |
| 5 | 0.189 |
| 6 | 1.05 |
| 7 | 1.27 |
| 8 | 0.025 |
| 9 | 72% @ 50 µM |
| 10 | 10% @ 50 µM |
| 11 | 9% @ 50 µM |
| 12 | 0.009 |
| 13 | 50.0 |
| 14 | 0.874 |
| 15 | 4.586 |
| 18 | 26% @ 50 µM |
| 19 | 2% @ 50 µM |
| 20 | 0.099 |
| 21 | 0.013 |
| 22 | 0.010 |
| 23 | 0.037 |
| 24 | 0.049 |
| 25 | 0.082 |
| 26 | 0.098 |
| 27 | 0.055 |
| 28 | 0.081 |
| 29 | 0.030 |
| 30 | 0.023 |
| 31 | 0.045 |
| 32 | 0.016 |
| 33 | 0.555 |
| 34 | 1.212 |
| 35 | 26% @ 50 µM |
| 36 | 0.059 |
| 37 | 0.364 |
| 38 | 0.007 |
| 39 | 0.010 |
| 40 | 0.005 |
| 41 | 0.012 |

-continued

| Example | $IC_{50}$ (µM) |
| --- | --- |
| 42 | 0.014 |
| 43 | 0.007 |
| 44 | 0.019 |
| 45 | 0.010 |
| 46 | 0.017 |
| 47 | N/D |
| 48 | 0.004 |
| 49 | 0.007 |
| 50 | 0.0234 |
| 51 | 0.714 |
| 52 | 0.285 |
| 53 | 0.233 |
| 54 | 0.191 |
| 55 | 0.148 |
| 56 | 1.503 |
| 57 | 2.894 |
| 58 | 1.338 |
| 58 | 0.502 |
| 60 | 0.350 |
| 61 | 2.524 |
| 62 | 3.137 |
| 63 | 0.005 |
| 64 | 0.014 |
| 65 | N/D |
| 66 | 25% @ 50 µM |
| 67 | 0.014 |
| 68 | 0.013 |
| 69 | 0.003 |
| 70 | 0.002 |
| 71 | 0.024 |
| 72 | 0.001 |
| 73 | 0.008 |
| 74 | 0.043 |
| 75 | 10% @ 1 µM |
| 76 | 36% @ 50 µM |
| 77 | 35 |
| 78 | 37% @ 50 µM |
| 79 | 21 |
| 80 | 46% @ 50 µM |
| 81 | 29% @ 50 µM |
| 82 | 28% @ 50 µM |
| 83 | 0.014 |
| 84 | 0.030 |
| 85/86 | 0.045 |
| 87 | 0.015 |

N/D: not determined

Based on the results obtained in the standard pharmacological test procedure, representative compounds of this invention have been shown to inhibit caspase activity and therefore useful for treating diseases related to inflammation, neurodegeneration, osteoarthritis and apoptosis. More particularly, the compounds of this invention are useful for the treatment of ischemic injury associated with stroke or myocardial infarction.

When ranges are used herein for physical properties, such as molecular weight, or chemical properties, such as chemical formulae, all combinations and subcombinations of ranges of specific embodiments therein are intended to be included.

The disclosure of each patent, patent application, and publication cited or described in this document is hereby incorporated by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed:
1. A compound of formula I:

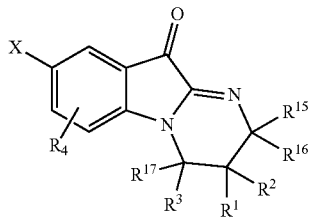

or a stereoisomer, or pharmaceutically-acceptable salt thereof;
wherein:
R$^1$ and R$^2$ are independently hydrogen, halogen, alkyl, aryl, heteroaryl, or R$^1$ and R$^2$ together with the carbon atom to which they are attached, form a C$_3$-C$_7$ carbocyclyl or a C$_3$-C$_7$ heterocycle;
R$^3$ and R$^{17}$ are independently, hydrogen and alkyl;
R$^{15}$ and R$^{16}$ are independently, hydrogen, alkyl, or aryl, provided that R$^{15}$ and R$^{16}$ are not both aryl;
R$^4$ is hydrogen, halogen, alkyl, nitrile, carboxyl, hydroxy, amino, R$^7$R$^8$N—, alkoxy, or perfluoroalkoxy;
X is cyano, perfluoroalkoxy,

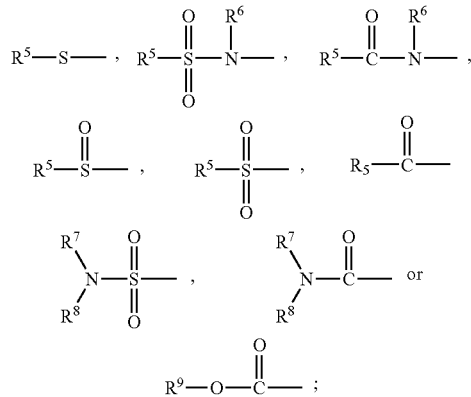

R$^5$ is alkyl, aryl, heteroaryl, heterocycle, or carbocyclyl;
R$^6$ is hydrogen or C$_1$-C$_3$ alkyl;
R$^7$ and R$^8$ are independently hydrogen, alkyl, aryl, heteroaryl, aralkyl, heteroaralkyl, alkanoyl, perfluoroalkanoyl, aroyl, heteroaroyl, aralkanoyl, heteroaralkanoyl, or R$^7$ and R$^8$ together with the nitrogen to which they are attached form a 5 to 10 member optionally substituted monocyclic or bicyclic ring system, which may further contain heteroatoms selected from oxygen, nitrogen or sulfur, provided that no ring may contain more than 3 heteroatoms; and
R$^9$ is hydrogen, alkyl, aryl, heteroaryl, aralkyl, C$_4$-C$_{12}$ heteroaralkyl, or C$_3$-C$_{12}$ carbocyclyl.

2. The compound according to claim 1, wherein said R$^1$ and R$^2$ are independently, hydrogen, halogen, alkyl or perfluoroalkyl.

3. The compound according to claim 1, wherein said R$^1$ and R$^2$ together with the atom to which they are attached form a C$_3$-C$_7$ carbocyclyl.

4. The compound according to claim 1, wherein said R$^3$ is hydrogen, alkyl or perfluoroalkyl.

5. The compound according to claim 1, wherein said R$^4$ is hydrogen, halogen, C$_1$-C$_3$ alkyl, perfluoroalkyl, nitro, nitrile, carboxyl, hydroxy, amino, R$^7$R$^8$N—, or alkoxy.

6. The compound according to claim 1, wherein said R$^5$ is alkyl, perfluoroalkyl, aryl, heteroaryl, heterocycle, or carbocyclyl.

7. The compound according to claim 1, wherein said R$^6$ is hydrogen, C$_1$-C$_3$ alkyl or C$_1$-C$_3$ perfluoroalkyl.

8. The compound according to claim 1, wherein said R$^7$ and R$^8$ are independently hydrogen, alkyl, perfluoroalkyl, aryl, heteroaryl, aralkyl, or heteroaralkyl.

9. The compound according to claim 1, wherein said R$^7$ and R$^8$ together have the formula:

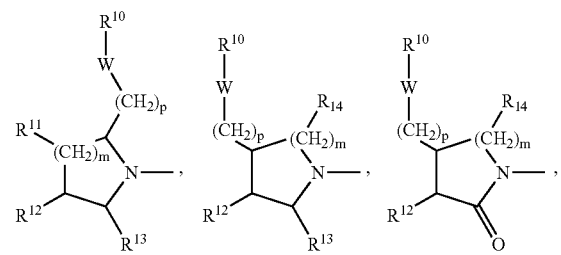

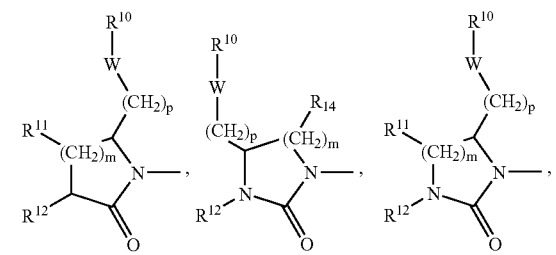

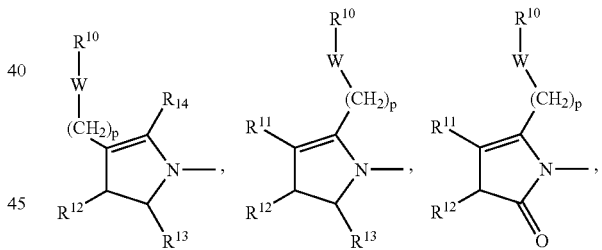

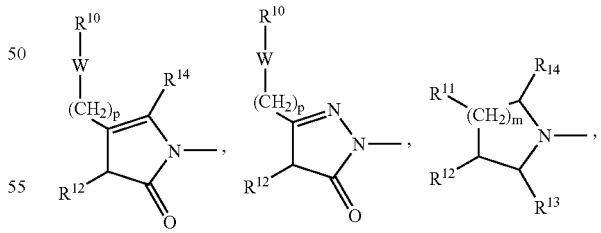

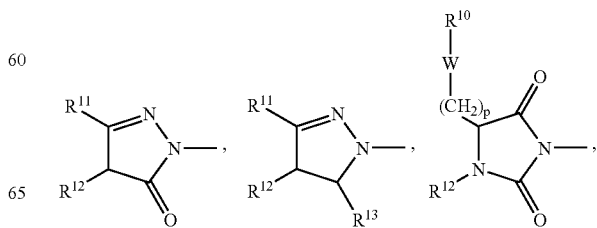

-continued

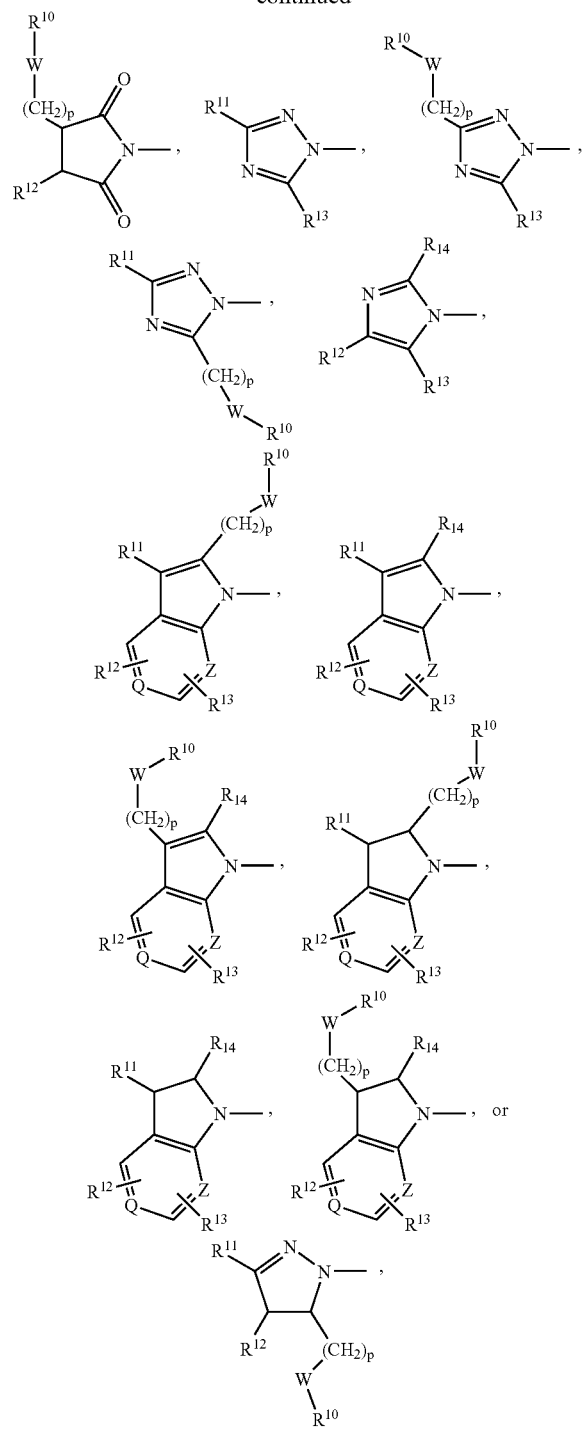

wherein:
W is sulfur, oxygen, —NR⁶—, —CH₂—, —C(=O)O—, —C(=O)NR⁶—, —NR⁶C(=O)O—,

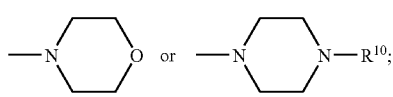

Q and Z can be the same or different, and are independently carbon or nitrogen;

$R^{10}$ is hydrogen, alkyl, aryl, heteroaryl, aralkyl, heteroaralkyl, alkanoyl, perfluoroalkanoyl, aroyl, heteroaroyl, aralkanoyl, carbocycl, or heteroaralkanoyl;

$R^{11}$, $R^{12}$, $R^{13}$ and $R^{14}$ can be the same or different, and are independently hydrogen, halogen, hydroxyl, nitrile, nitro, $R^7R^8N$—, $R^7R^8NC(O)$—, —$NR^6C(O)R^9$, —$C(O)_2R^9$, —C(O)H, —$C(O)R^9$, alkyl, alkanoyl, perfluoroalkanoyl, aroyl, heteroaroyl, aralkanoyl, heteroaralkanoyl, or $R^{11}$ and $R^{12}$ together form an optionally substituted ring comprising 5 to 7 atoms selected from C, N, S and O, or $R^{12}$ and $R^{13}$ together form an optionally substituted ring comprising 5 to 7 atoms selected from C, N, S and O; and each of m and p are, independently, an integer of 0 to 2.

10. The compound according to claim 1, wherein said $R^9$ is hydrogen, alkyl, perfluoroalkyl, aryl, heteroaryl, aralkyl, heteroaralkyl, or carbocyclyl.

11. The compound of claim 1, wherein said $R^{15}$ and $R^{16}$ are independently, hydrogen or methyl.

12. The compound according to claim 9, wherein said $R^{10}$ is hydrogen, alkyl, aryl, heteroaryl, aralkyl, heteroaralkyl, alkanoyl, aroyl, heteroaroyl, aralkanoyl, or heteroaralkanoyl.

13. The compound according to claim 9, wherein said $R^{11}$, $R^{12}$, $R^{13}$, and $R^{14}$ are independently hydrogen, halogen, hydroxyl, nitrile, nitro, $R^7R^8N$—, $R^7R^8NC(O)$—, —$NR^6C(O)R^9$, —$C(O)_2R^9$, —C(O)H, —$C(O)R^9$, alkyl, perfluoroalkyl, alkanoyl, aroyl, heteroaroyl, aralkanoyl, or heteroaralkanoyl.

14. The compound according to claim 9, wherein said $R^{11}$ and $R^{12}$ together form an optionally substituted ring comprising 5 to 7 atoms selected from C, N, S and O.

15. The compound according to claim 9, wherein said $R^{12}$ and $R^{13}$ together form an optionally substituted ring comprising 5 to 7 atoms selected from C, N, S and O.

16. The compound according to claim 1, wherein said X is cyano,

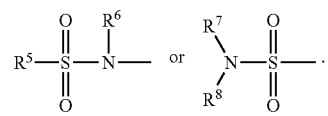

17. The compound according to claim 9, wherein said $R^7$ and $R^8$ together have the formula:

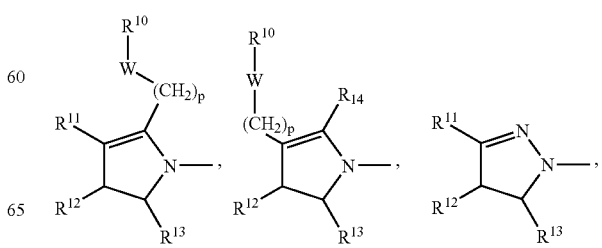

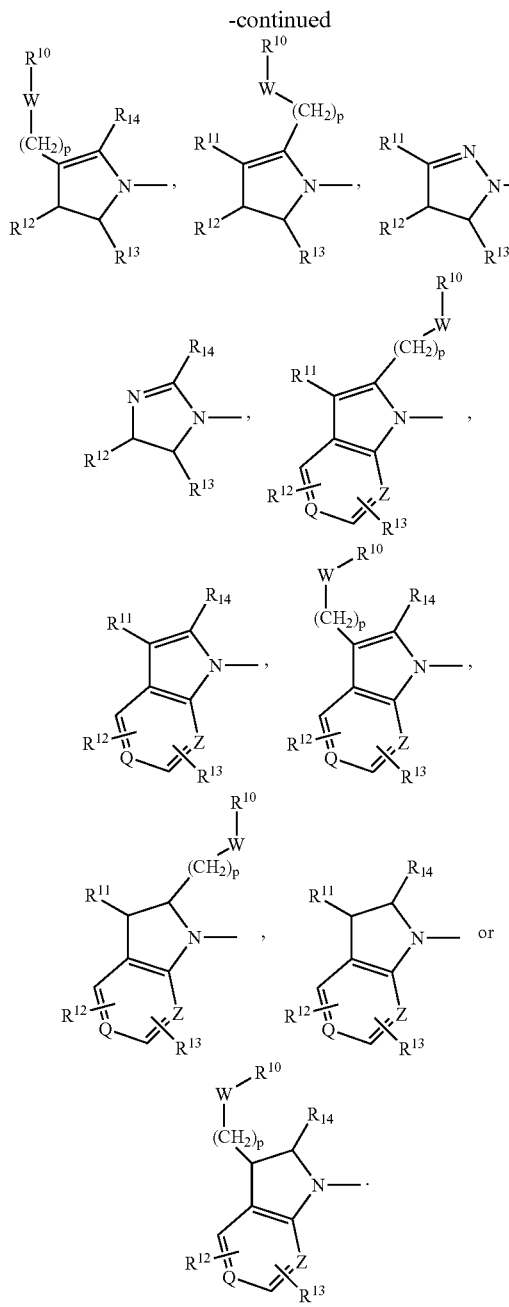

18. The compound according to claim 9, wherein W is oxygen, —NR⁶—, —CH₂—, —C(=O)O—, —C(=O)NR⁶—, or —NR⁶C(=O)O—.

19. The compound according to claim 9, wherein said Q is carbon or nitrogen.

20. The compound according to claim 9, wherein said Z is carbon or nitrogen.

21. The compound according to claim 1, wherein said compound is:

8-{[(2S)-2-(Methoxymethyl)pyrrolidin-1-yl]sulfonyl}-3,4-dihydropyrimido[1,2-a]indol-10(2H)-one;

8-{[(2S)-2-(Methoxymethyl)pyrrolidin-1-yl]sulfonyl}-3,3-dimethyl-3,4-dihydropyrimido[1,2-a]indol-10(2H)-one;

8-{[(2S)-2-(Phenoxymethyl)pyrrolidin-1-yl]sulfonyl}-3,4-dihydropyrimido[1,2-a]indol-10(2H)-one];

3,3-Dimethyl-8-{[(2S)-2-(phenoxymethyl)pyrrolidin-1-yl]sulfonyl}-3,4-dihydropyrimido[1,2-a]indol-10(2H)-one;

7-Chloro-8-{[(2S)-2-(methoxymethyl)pyrrolidin-1-yl-]sulfonyl}-3,4-dihydropyrimido[1,2-a]indol-10(2H)-one;

8-{[(2R)-2-(Methoxymethyl)pyrrolidin-1-yl]sulfonyl}-3,3-dimethyl-3,4-dihydropyrimido[1,2-a]indol-10(2H)-one;

N-Methyl-10-oxo-2,3,4,10-tetrahydropyrimido[1,2-a]indole-8-sulfonamide;

8-{[(2S)-2-(Hydroxymethyl)pyrrolidin-1-yl]sulfonyl}-3,3-dimethyl-3,4-dihydropyrimido[1,2-a]indol-10(2H)-one;

3,3-Dimethyl-8-(pyrrolidin-1-ylsulfonyl)-3,4-dihydropyrimido[1,2-a]indol-10(2H)-one;

N-(10-Oxo-2,3,4,10-tetrahydropyrimido[1,2-a]indol-8-yl)benzamide;

8-({(2S)-2-[(4-Methoxyphenoxy)methyl]pyrrolidin-1-yl}sulfonyl)-3,3-dimethyl-3,4-dihydropyrimido[1,2-a]indol-10(2H)-one;

8-({(2S)-2-[(4-Fluorophenoxy)methyl]pyrrolidin-1-yl}sulfonyl)-3,3-dimethyl-3,4-dihydropyrimido[1,2-a]indol-10(2H)-one;

8-({(2S)-2-[(4-Chlorophenoxy)methyl]pyrrolidin-1-yl}sulfonyl)-3,3-dimethyl-3,4-dihydropyrimido[1,2-a]indol-10(2H)-one;

3,3-Dimethyl-8-({(2S)-2-[(4-methylphenoxy)methyl]pyrrolidin-1-yl}sulfonyl)-3,3-dimethyl-3,4-dihydropyrimido[1,2-a]indol-10(2H)-one;

8-({(2S)-2-[(2-Chloro-4-methoxyphenoxy)methyl]pyrrolidin-1-yl}sulfonyl)-3,3-dimethyl-3,4-dihydropyrimido[1,2-a]indol-10(2H)-one;

8-({(2S)-2-[(2-Chloro-4-methylphenoxy)methyl]pyrrolidin-1-yl}sulfonyl)-3,3-dimethyl-3,4-dihydropyrimido[1,2-a]indol-10(2H)-one;

8-({(2S)-2-[(4-Acetyl-2-methylphenoxy)methyl]pyrrolidin-1-yl}sulfonyl)-3,3-dimethyl-3,4-dihydropyrimido[1,2-a]indol-10(2H)-one;

8-({(2S)-2-[(4-tert-Butylphenoxy)methyl]pyrrolidin-1-yl}sulfonyl)-3,3-dimethyl-3,4-dihydropyrimido[1,2-a]indol-10(2H)-one;

8-({(2S)-2-[(4-Acetylphenoxy)methyl]pyrrolidin-1-yl}sulfonyl)-3,3-dimethyl-3,4-dihydropyrimido[1,2-a]indol-10(2H)-one;

8-({(2S)-2-[(4-Fluoro-3-methylphenoxy)methyl]pyrrolidin-1-yl}sulfonyl)-3,3-dimethyl-3,4-dihydropyrimido[1,2-a]indol-10(2H)-one;

3,3-Dimethyl-8-({(2S)-2-[(3-(trifluoromethyl)phenoxy)methyl]pyrrolidin-1-yl}sulfonyl)-3,4-dihydropyrimido[1,2-a]indol-10(2H)-one;

8-(2,3-Dihydro-1H-indol-1-ylsulfonyl)-3,3-dimethyl-3,4-dihydropyrimido[1,2-a]indol-10(2H)-one;

8-{[(2S)-2-(Methoxymethyl)-2,3-dihydro-1H-indol-1-yl]sulfonyl}-3,3-dimethyl-3,4-dihydropyrimido[1,2-a]indol-10(2H)-one;

3,3-Dimethyl-8-{[(2S)-2-(phenoxymethyl)-2,3-dihydro-1H-indol-1-yl]sulfonyl}-3,4-dihydropyrimido[1,2-a]indol-10(2H)-one;

8-[((2S)-2-{[(2-Bromopyridin-3-yl)oxy]methyl}pyrrolidin-1-yl)sulfonyl]-3,3-dimethyl-3,4-dihydropyrimido[1,2-a]indol-10(2H)-one;

8-({(2S)-2-[(Cyclohexylamino)methyl]pyrrolidin-1-yl}sulfonyl)-3,3-dimethyl-3,4-dihydropyrimido[1,2-a]indol-10(2H)-one;

N-(3,3-Dimethyl-10-oxo-2,3,4,10-tetrahydropyrimido[1,2-a]indol-8-yl)benzenesulfonamide;

3,3-Dimethyl-8-({(2S)-2-[(pyridin-2-yloxy)methyl]pyrrolidin-1-yl}sulfonyl)-3,4-dihydropyrimido[1,2-a]indol-10(2H)-one;

8-[((2S)-2-{[(5-Chloropyridin-2-yl)oxy]methyl}pyrrolidin-1-yl)sulfonyl]-3,3-dimethyl-3,4-dihydropyrimido[1,2-a]indol-10(2H)-one;

8-[((2S)-2-{[(6-Chloropyridin-2-yl)oxy]methyl}pyrrolidin-1-yl)sulfonyl]-3,3-dimethyl-3,4-dihydropyrimido[1,2-a]indol-10(2H)-one;

3,3-Dimethyl-8-[((2S)-2-{[(6-methylpyridin-2-yl)oxy]methyl}pyrrolidin-1-yl)sulfonyl]-3,4-dihydropyrimido[1,2-a]indol-10(2H)-one;

3,3-Dimethyl-8-{[(2S)-2-({[5-(trifluoromethyl)pyridin-2-yl]oxy}methyl)pyrrolidin-1-yl]sulfonyl}-3,4-dihydropyrimido[1,2-a]indol-10(2H)-one;

8-[((2S)-2-{[(2-chloropyridin-3-yl)oxy]methyl}pyrrolidin-1-yl)sulfonyl]-3,3-dimethyl-3,4-dihydropyrimido[1,2-a]indol-10(2H)-one;

3,3-Dimethyl-8-[((2S)-2-{[(6-methylpyridin-3-yl)oxy]methyl}pyrrolidin-1-yl)sulfonyl]-3,4-dihydropyrimido[1,2-a]indol-10(2H)-one;

Methyl 5-({(2S)-1-[(3,3-dimethyl-10-oxo-2,3,4,10-tetrahydropyrimido[1,2-a]indol-8-yl)sulfonyl]pyrrolidin-2-yl}methoxy)nicotinate;

8-[((2S)-2-{[(2-Iodo-6-methylpyridin-3-yl)oxy]methyl}pyrrolidin-1-yl)sulfonyl]-3,3-dimethyl-3,4-dihydropyrimido[1,2-a]indol-10(2H)-one;

3,3-Dimethyl-8-({(2S)-2-[(pyridin-3-yloxy)methyl]pyrrolidin-1-yl}sulfonyl)-3,4-dihydropyrimido[1,2-a]indol-10(2H)-one;

8-[((2S)-2-{[(5-Chloropyridin-3-yl)oxy]methyl}pyrrolidin-1-yl)sulfonyl]-3,3-dimethy-3,4-dihydropyrimido[1,2-a]indol-10(2H)-one;

3,3-Dimethyl-8-[((2S)-2-{[(2-methylpyridin-3-yl)oxy]methyl}pyrrolidin-1-yl)sulfonyl]-3,4-dihydropyrimido[1,2-a]indol-10(2H)-one;

3-Bromo-N-(3,3-dimethyl-10-oxo-2,3,4,10-tetrahydropyrimido[1,2-a]indol-8-yl)benzenesulfonamide;

N-(3,3-Dimethyl-10-oxo-2,3,4,10-tetrahydropyrimido[1,2-a]indol-8-yl)-4-methylbenzenesulfonamide;

3-Chloro-N-(3,3-dimethyl-10-oxo-2,3,4,10-tetrahydropyrimido[1,2-a]indol-8-yl)-4-fluorobenzenesulfonamide;

3,4-Dichloro-N-(3,3-dimethyl-10-oxo-2,3,4,10-tetrahydropyrimido[1,2-a]indol-8-yl)benzenesulfonamide;

N-(3,3-Dimethyl-10-oxo-2,3,4,10-tetrahydropyrimido[1,2-a]indol-8-yl)-3-(trifluoromethyl)benzenesulfonamide;

N-(3,3-Dimethyl-10-oxo-2,3,4,10-tetrahydropyrimido[1,2-a]indol-8-yl)-2-fluorobenzenesulfonamide;

N-(3,3-Dimethyl-10-oxo-2,3,4,10-tetrahydropyrimido[1,2-a]indol-8-yl)-4-methoxybenzenesulfonamide;

N-(3,3-Dimethyl-10-oxo-2,3,4,10-tetrahydropyrimido[1,2-a]indol-8-yl)-4-fluorobenzenesulfonamide;

4-Chloro-N-(3,3-dimethyl-10-oxo-2,3,4,10-tetrahydropyrimido[1,2-a]indol-8-yl)benzenesulfonamide;

2-Bromo-N-(3,3-dimethyl-10-oxo-2,3,4,10-tetrahydropyrimido[1,2-a]indol-8-yl)benzenesulfonamide;

N-(3,3-Dimethyl-10-oxo-2,3,4,10-tetrahydropyrimido[1,2-a]indol-8-yl)-3-methoxybenzenesulfonamide;

N-(3,3-Dimethyl-10-oxo-2,3,4,10-tetrahydropyrimido[1,2-a]indol-8-yl)-4-(trifluoromethoxy)benzenesulfonamide;

N-(3,3-Dimethyl-10-oxo-2,3,4,10-tetrahydropyrimido[1,2-a]indol-8-yl)-3,5-bis(trifluoromethyl)benzenesulfonamide;

3,3-Dimethyl-8-{[(2S)-2-(morpholin-4-ylmethyl)pyrrolidin-1-yl]sulfonyl}-3,4-dihydropyrimido[1,2-a]indol-10(2H)-one;

Ethyl 4-({(2S)-1-[(3,3-dimethyl-10-oxo-2,3,4,10-tetrahydropyrimido[1,2-a]indol-8-yl)sulfonyl]pyrrolidin-2-yl}methyl)piperazine-1-carboxylate;

8-({(2S)-2-[(Cyclopentylamino)methyl]pyrrolidin-1-yl}sulfonyl)-3,3-dimethyl-3,4-dihydropyrimido[1,2-a]indol-10(2H)-one;

3,3-Dimethyl-8-{[(2S)-2-(phenoxymethyl)pyrrolidin-1-yl]carbonyl}-3,4-dihydropyrimido[1,2-a]indol-10(2H)-one;

8-({(2S)-2-[(4-Methoxyphenoxy)methyl]pyrrolidin-1-yl}sulfonyl)-3,3-dimethyl-3,4-dihydropyrimido[1,2-a]indol-10(2H)-one;

8-({(2S)-2-[(4-Fluorophenoxy)methyl]pyrrolidin-1-yl}sulfonyl)-3,3-dimethyl-3,4-dihydropyrimido[1,2-a]indol-10(2H)-one;

8-({(2S)-2-[(4-Chlorophenoxy)methyl]pyrrolidin-1-yl}sulfonyl)-3,3-dimethyl-3,4-dihydropyrimido[1,2-a]indol-10(2H)-one;

3,3-Dimethyl-8-({(2S)-2-[(4-methylphenoxy)methyl]pyrrolidin-1-yl}sulfonyl)-3,4-dihydropyrimido[1,2-a]indol-10(2H)-one;

8-({(2S)-2-[(2-Chloro-4-methoxyphenoxy)methyl]pyrrolidin-1-yl}sulfonyl)-3,3-dimethyl-3,4-dihydropyrimido[1,2-a]indol-10(2H)-one;

8-({(2S)-2-[(2-Chloro-4-methylphenoxy)methyl]pyrrolidin-1-yl}sulfonyl)-3,3-dimethyl-3,4-dihydropyrimido[1,2-a]indol-10(2H)-one;

8-({(2S)-2-[(4-Acetyl-2-methylphenoxy)methyl]pyrrolidin-1-yl}sulfonyl)-3,3-dimethyl-3,4-dihydropyrimido[1,2-a]indol-10(2H)-one;

8-({(2S)-2-[(4-Tert-butylphenoxy)methyl]pyrrolidin-1-yl}sulfonyl)-3,3-dimethyl-3,4-dihydropyrimido[1,2-a]indol-10(2H)-one;

8-({(2S)-2-[(4-Acetylphenoxy)methyl]pyrrolidin-1-yl}sulfonyl)-3,3-dimethyl-3,4-dihydropyrimido[1,2-a]indol-10(2H)-one;

8-({(2S)-2-[(4-Fluoro-3-methylphenoxy)methyl]pyrrolidin-1-yl}sulfonyl)-3,3-dimethyl-3,4-dihydropyrimido[1,2-a]indol-10(2H)-one;

3,3-Dimethyl-8-[((2S)-2-{[3-(trifluoromethyl)phenoxy]methyl}pyrrolidin-1-yl)sulfonyl]-3,4-dihydropyrimido[1,2-a]indol-10(2H)-one;

8-(2,3-Dihydro-1H-indol-1-ylsulfonyl)-3,3-dimethyl-3,4-dihydropyrimido[1,2-a]indol-10(2H)-one;

8-{[(2S)-2-(Methoxymethyl)-2,3-dihydro-1H-indol-1-yl]sulfonyl}-3,3-dimethyl-3,4-dihydropyrimido[1,2-a]indol-10(2H)-one;

3,3-Dimethyl-8-{[(2S)-2-(phenoxymethyl)-2,3-dihydro-1H-indol-1-yl]sulfonyl}-3,4-dihydropyrimido[1,2-a]indol-10(2H)-one;

8-[((2S)-2-{[(2-Bromopyridin-3-yl)oxy]methyl}pyrrolidin-1-yl)sulfonyl]-3,3-dimethyl-3,4-dihydropyrimido[1,2-a]indol-10(2H)-one;

3,3-Dimethyl-8-({(2S)-2-[(pyridin-2-yloxy)methyl]pyrrolidin-1-yl}sulfonyl)-3,4-dihydropyrimido[1,2-a]indol-10(2H)-one;

8-[((2S)-2-{[(5-Chloropyridin-2-yl)oxy]methyl}pyrrolidin-1-yl)sulfonyl]-3,3-dimethyl-3,4-dihydropyrimido[1,2-a]indol-10(2H)-one;

8-[((2S)-2-{[(6-Chloropyridin-2-yl)oxy]methyl}pyrrolidin-1-yl)sulfonyl]-3,3-dimethyl-3,4-dihydropyrimido[1,2-a]indol-10(2H)-one;

3,3-Dimethyl-8-[((2S)-2-{[(6-methylpyridin-2-yl)oxy]
methyl}pyrrolidin-1-yl)sulfonyl]-3,4-dihydropyrimido
[1,2-a]indol-10(2H)-one;
3,3-Dimethyl-8-{[(2S)-2-({[5-(trifluoromethyl)pyridin-
2-yl]oxy}methyl)pyrrolidin-1-yl]sulfonyl}-3,4-dihy-
dropyrimido[1,2-a]indol-10(2H)-one;
8-[((2S)-2-{[(2-Chloropyridin-3-yl)oxy]
methyl}pyrrolidin-1-yl)sulfonyl]-3,3-dimethyl-3,4-di-
hydropyrimido[1,2-a]indol-10(2H)-one;
3,3-Dimethyl-8-[((2S)-2-{[(6-methylpyridin-3-yl)oxy]
methyl}pyrrolidin-1-yl)sulfonyl]-3,4-dihydropyrimido
[1,2-a]indol-10(2H)-one;
Methyl 5-({(2S)-1-[(3,3-dimethyl-10-oxo-2,3,4,10-tet-
rahydropyrimido[1,2-a]indol-8-yl)sulfonyl]pyrrolidin-
2-yl}methoxy)nicotinate;
8-[((2S)-2-{[(2-Iodo-6-methylpyridin-3-yl)oxy]
methyl}pyrrolidin-1-yl)sulfonyl]-3,3-dimethyl-3,4-di-
hydropyrimido[1,2-a]indol-10(2H)-one;
3,3-Dimethyl-8-({(2S)-2-[(pyridin-3-yloxy)methyl]pyr-
rolidin-1-yl}sulfonyl)-3,4-dihydropyrimido[1,2-a]in-
dol-10(2H)-one;
8-[((2S)-2-{[(5-Chloropyridin-3-yl)oxy]
methyl}pyrrolidin-1-yl)sulfonyl]-3,3-dimethyl-3,4-di-
hydropyrimido[1,2-a]indol-10(2H)-one;
3,3-Dimethyl-8-[((2S)-2-{[(2-methylpyridin-3-yl)oxy]
methyl}pyrrolidin-1-yl)sulfonyl]-3,4-dihydropyrimido
[1,2-a]indol-10(2H)-one;
3,3-Dimethyl-8-({(2S)-2-[(pyridin-2-yloxy)methyl]pyr-
rolidin-1-yl}sulfonyl)-3,4-dihydropyrimido[1,2-a]in-
dol-10(2H)-one;
8-({(2S)-2-[(Cyclohexylamino)methyl]pyrrolidin-1-
yl}sulfonyl)-3,3-dimethyl-3,4-dihydropyrimido[1,2-a]
indol-10(2H)-one;
3,3-Dimethyl-8-{[(2S)-2-(morpholin-4-ylmethyl)pyrroli-
din-1-yl]sulfonyl}-3,4-dihydropyrimido[1,2-a]indol-
10(2H)-one;
Ethyl 4-({(2S)-1-[(3,3-dimethyl-10-oxo-2,3,4,10-tetrahy-
dropyrimido[1,2-a]indol-8-yl)sulfonyl]pyrrolidin-2-
yl}methyl)piperazine-1-carboxylate;
8-({(2S)-2-[(Cyclopentylamino)methyl]pyrrolidin-1-
yl}sulfonyl)-3,3-dimethyl-3,4-dihydropyrimido[1,2-a]
indol-10(2H)-one;
3,3-Dimethyl-8-({(2S)-2-[(4-methylpiperazin-1-yl)me-
thyl]pyrrolidin-1-yl}sulfonyl)-3,4-dihydropyrimido[1,
2-a]indol-10(2H)-one;
N-(3,3-Dimethyl-10-oxo-2,3,4,10-tetrahydropyrimido[1,
2-a]indol-8-yl)benzenesulfonamide;
3-Bromo-N-(3,3-dimethyl-10-oxo-2,3,4,10-tetrahydropy-
rimido[1,2-a]indol-8-yl)benzenesulfonamide;
N-(3,3-Dimethyl-10-oxo-2,3,4,10-tetrahydropyrimido[1,
2-a]indol-8-yl)-4-methylbenzenesulfonamide;
3-Chloro-N-(3,3-dimethyl-10-oxo-2,3,4,10-tetrahydropy-
rimido[1,2-a]indol-8-yl)-4-fluorobenzenesulfonamide;
3,3-Dimethyl-8-{[(2S)-2-(phenoxymethyl)pyrrolidin-1-
yl]carbonyl}-3,4-dihydropyrimido[1,2-a]indol-10
(2H)-one;
N-(3,3-Dimethyl-10-oxo-2,3,4,10-tetrahydropyrimido[1,
2-a]indol-8-yl)-3-(trifluoromethyl)benzenesulfona-
mide;
8-{[(2S)-2-(Methoxymethyl)pyrrolidin-1-yl]carbonyl}-3,
3-dimethyl-3,4-dihydropyrimido[1,2-a]indol-10(2H)-
one;
3,3-Dimethyl-10-oxo-N-phenyl-2,3,4,10-tetrahydropy-
rimido[1,2-a]indole-8-carboxamide;
N-Cyclopentyl-3,3-dimethyl-10-oxo-2,3,4,10-tetrahydro-
pyrimido[1,2-a]indole-8-carboxamide;

3,3-Dimethyl-8-(pyrrolidin-1-ylcarbonyl)-3,4-dihydropy-
rimido[1,2-a]indol-10(2H)-one;
3,3-Dimethyl-8-(piperidin-1-ylcarbonyl)-3,4-dihydropy-
rimido[1,2-a]indol-10(2H)-one;
8-(2,3-Dihydro-1H-indol-1-ylcarbonyl)-3,3-dimethyl-3,
4-dihydropyrimido[1,2-a]indol-10(2H)-one;
3,3-Dimethyl-8-[(4-methylpiperazin-1-yl)carbonyl]-3,4-
dihydropyrimido[1,2-a]indol-10(2H)-one;
8-[(4-Acetylpiperazin-1-yl)carbonyl]-3,3-dimethyl-3,4-
dihydropyrimido[1,2-a]indol-10(2H)-one;
8'-{[(2S)-2-(Methoxymethyl)pyrrolidin-1-yl]
sulfonyl}spiro[cyclopentane-1,3'-pyrimido[1,2-a]in-
dol]-10'(2'H)-one;
8'-{[(2S)-2-(Methoxymethyl)pyrrolidin-1-yl]
sulfonyl}spiro[cyclohexane-1,3'-pyrimido[1,2-a]in-
dol]-10'(2'H)-one;
8'-{[(2S)-2-(Methoxymethyl)pyrrolidin-1-yl]
sulfonyl}spiro[cyclobutane-1,3'-pyrimido[1,2-a]in-
dol]-10'(2'H)-one;
8'-{[(2S)-2-(Phenoxymethyl)pyrrolidin-1-yl]
sulfonyl}spiro[cyclopentane-1,3'-pyrimido[1,2-a]in-
dol]-10'(2'H)-one;
8'-{[(2S)-2-(Phenoxymethyl)pyrrolidin-1-yl]
sulfonyl}spiro[cyclohexane-1,3'-pyrimido[1,2-a]in-
dol]-10'(2'H)-one;
8'-{[(2S)-2-(Phenoxymethyl)pyrrolidin-1-yl]
sulfonyl}spiro[cyclobutane-1,3'-pyrimido[1,2-a]in-
dol]-10'(2'H)-one;
8'-{[(2S)-2-(morpholin-4-ylmethyl)pyrrolidin-1-yl]
sulfonyl}spiro[cyclopentane-1,3'-pyrimido[1,2-a]in-
dol]-10'(2'H)-one;
8'-({(2S)-2-[(4-Methylpiperazin-1-yl)methyl]pyrrolidin-
1-yl}sulfonyl)spiro[cyclopentane-1,3'-pyrimido[1,2-a]
indol]-10'(2'H)-one;
8'-{[(2S)-2-(methoxymethyl)pyrrolidin-1-yl]
sulfonyl}spiro[cycloheptane-1,3'-pyrimido[1,2-a]in-
dol]-10'(2'H)-one;
2-Methyl-8-(pyrrolidin-1-ylsulfony)-3,4-dihydropy-
rimido[1,2-a'indol-10(2H)-one; or
pharmaceutically acceptable salts thereof.

22. A composition comprising the compound of claim 1 and one or more pharmaceutically acceptable carriers.

23. A method for treating a patient suffering from arthritis, myocardial infarction or stroke comprising the step of administering to the patient a therapeutically effective amount of a compound of claim 1.

24. A method comprising contacting a caspase with a compound of formula I:

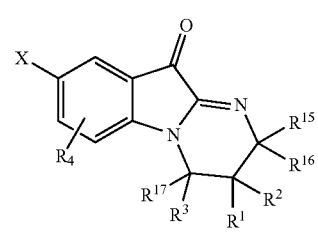

or a, stereoisomer, or pharmaceutically-acceptable salt thereof;
wherein:
$R^1$ and $R^2$ are independently hydrogen, halogen, alkyl, aryl, heteroaryl, or $R^1$ and $R^2$ together with the carbon atom to which they are attached, form a $C_3$-$C_7$ carbocyclyl or a $C_3$-$C_7$ heterocycle;

$R^3$ and $R^{17}$ are independently, hydrogen and alkyl;

$R^{15}$ and $R^{16}$ are independently hydrogen, alkyl, or aryl, provided that $R^{15}$ and $R^{16}$ are not both aryl;

$R^4$ is hydrogen, halogen, alkyl, nitro, nitrile, carboxyl, hydroxy, amino, $R^7R^8N$—, alkoxy, or perfluoroalkoxy;

X is nitro, cyano, alkyl, perfluoroalkoxy, halogen, $$R^5-S-, \quad R^5-\overset{O}{\underset{O}{\overset{\|}{S}}}-\overset{R^6}{\underset{}{N}}-, \quad R^5-\overset{O}{\overset{\|}{C}}-\overset{R^6}{\underset{}{N}}-, \quad R^5-\overset{O}{\overset{\|}{S}}-,$$

$$R^5-\overset{O}{\underset{O}{\overset{\|}{S}}}-, \quad R^5-\overset{O}{\overset{\|}{C}}-, \quad \overset{R^7}{\underset{R^8}{N}}-\overset{O}{\underset{O}{\overset{\|}{S}}}-, \quad \overset{R^7}{\underset{R^8}{N}}-\overset{O}{\overset{\|}{C}}- \quad \text{or}$$

$$R^9-O-\overset{O}{\overset{\|}{C}}-;$$

$R^5$ is alkyl, aryl, heteroaryl, heterocycle, or carbocyclyl;

$R^6$ is hydrogen or $C_1$-$C_3$ alkyl;

$R^7$ and $R^8$ are independently hydrogen, alkyl, aryl, heteroaryl, aralkyl, heteroaralkyl, alkanoyl, perfluoroalkanoyl, aroyl, heteroaroyl, aralkanoyl, heteroaralkanoyl, or $R^7$ and $R^8$ together with the nitrogen to which they are attached form a 5 to 10 member optionally substituted monocyclic or bicyclic ring system, which may further contain heteroatoms selected from oxygen, nitrogen or sulfur, provided that no ring may contain more than 3 heteroatoms; and $R^9$ is hydrogen, alkyl, aryl, heteroaryl, aralkyl, $C_4$-$C_{12}$ heteroaralkyl, or $C_3$-$C_{12}$ carbocyclyl.

25. The method of claim 24 further comprising determining the activity of said caspase.

26. The method of claim 25 wherein said determination is made before said contacting step.

27. The method of claim 25 wherein said determination is made after said contacting step.

28. A compound of formula II:

<br>

II or a prodrug, stereoisomer, or pharmaceutically-acceptable salt thereof;

wherein:

$R^1$ and $R^2$ are independently hydrogen, halogen, alkyl, aryl, heteroaryl, or $R^1$ and $R^2$ together with the carbon atom to which they are attached, form a $C_3$-$C_7$ carbocyclyl or a $C_3$-$C_7$ heterocycle;

$R^3$ and $R^{17}$ are independently hydrogen or alkyl;

$R^{15}$ and $R^{16}$ are independently, hydrogen, alkyl, or aryl, provided that $R^{15}$ and $R^{16}$ are not both aryl;

$R^4$ is hydrogen, halogen, alkyl, nitro, nitrile, carboxyl, hydroxy, amino, $R^7R^8N$—, alkoxy, or perfluoroalkoxy;

X is nitro, cyano, alkyl, perfluoroalkoxy, halogen, $$R^5-S-, \quad R^5-\overset{O}{\underset{O}{\overset{\|}{S}}}-\overset{R^6}{\underset{}{N}}-, \quad R^5-\overset{O}{\overset{\|}{C}}-\overset{R^6}{\underset{}{N}}-, \quad R^5-\overset{O}{\overset{\|}{S}}-,$$

$$R^5-\overset{O}{\underset{O}{\overset{\|}{S}}}-, \quad R^5-\overset{O}{\overset{\|}{C}}-, \quad \overset{R^7}{\underset{R^8}{N}}-\overset{O}{\underset{O}{\overset{\|}{S}}}-, \quad \overset{R^7}{\underset{R^8}{N}}-\overset{O}{\overset{\|}{C}}- \quad \text{or}$$

$$R^9-O-\overset{O}{\overset{\|}{C}}-;$$

$R^5$ is alkyl, aryl, heteroaryl, heterocycle, or carbocyclyl;

$R^6$ is hydrogen or $C_1$-$C_3$ alkyl;

$R^7$ and $R^8$ are independently hydrogen, alkyl, aryl, heteroaryl, aralkyl, heteroaralkyl, alkanoyl, perfluoroalkanoyl, aroyl, heteroaroyl, aralkanoyl, heteroaralkanoyl, or $R^7$ and $R^8$ together with the nitrogen to which they are attached form a 5 to 10 member optionally substituted monocyclic or bicyclic ring system, which may further contain heteroatoms selected from oxygen, nitrogen or sulfur, provided that no ring may contain more than 3 heteroatoms;

$R^9$ is hydrogen, alkyl, aryl, heteroaryl, aralkyl, $C_4$-$C_{12}$ heteroaralkyl, or $C_3$-$C_{12}$ carbocyclyl; and n is an integer of 0 or 1.

29. The compound according to claim 28, wherein the compound is:

8'-{[(2S)-2-(Methoxymethyl)pyrrolidinyl]sulfonyl}-3',4'-dihydrospiro(1,3-dioxane-2,10'(2'H)-pyrimido(1,2-a)indole)

8'-{[(2S)-2-(Phenoxymethyl)pyrrolidin-1-yl]sulfonyl}-3', 4'-dihydro-2'H-spiro[1,3-dioxane-2,10'-pyrimido[1,2-a]indole]

3',3'-Dimethyl-8'-{[(2S)-2-(phenoxymethyl)pyrrolidin-1-yl]sulfonyl}-3',4'-dihydro-2'H-spiro[1,3-dioxane-2,10'-pyrimido[1,2-a]indole];

8'-{[(2R)-2-(Methoxymethyl)pyrrolidin-1-yl]sulfonyl}-3',3'-dimethyl-3',4'-dihydro-2'H-spiro[1,3-dioxane-2, 10'pyrimido[1,2-a]indole];

N-Benzyl-N-methyl-3',4'-dihydrospiro[1,3-dioxane-2,10' (2'H)-pyrimido[1,2-alpha]-indole]-8'-sulfonamide;

8'-({(2S)-2-[(Benzyloxy)methyl]pyrrolidin-1-yl}sulfonyl)-3',3'-dimethyl-3',4'-dihydro -2'H-spiro[1, 3-dioxane-2,10'-pyrimido[1,2-a]indole];

3',3'-Dimethyl-8'-(pyrrolidin-1-ylsulfonyl)-3',4'-dihydro-2'H-spiro[1,3-dioxane-2,10'-pyrimido[1,2-a]indole];

3',4'-Dihydro-2'H-spiro[1,3-dioxane-2,10'-pyrimido[1,2-a]indol]-8'-amine;

N-3',4'-Dihydro-2'H-spiro[1,3-dioxane-2,10'-pyrimido[1,2-a]indol]-8'-ylbenzamide 3',3'-dimethyl-3',4'-dihydro-2'H-spiro[1,3-dioxane-2,10'-pyrimido[1,2-a]indole]-8'-carbonitrile;

{(2S)-1-[(3',3'-Dimethyl-3',4'-dihydro-2'H-spiro[1,3-dioxane-2,10'-pyrimido[1,2-a]indol]-8'-yl)sulfonyl]pyrrolidin-2-yl}methanol;

{(2S)-1-[(3',3'-Dimethyl-3',4'-dihydro-2'H-spiro[1,3-dioxane-2,10'-pyrimido[1,2-a]indol]-8'-yl)sulfonyl]pyrrolidin-2-yl}methyl 4-methylbenzenesulfonate;

3',3'-Dimethyl-3',4'-dihydro-2'H-spiro[1,3-dioxane-2,10'-pyrimido[1,2-a]indol]-8'amine;

N-(3',3'-Dimethyl-3',4'-dihydro-2'H-spiro[1,3-dioxane-2,10'-pyrimido[1,2-a]indol]-8'-yl)benzenesulfonamide;

8'-Bromo-3',3'-dimethyl-3',4'-dihydro-2'H-spiro[1,3-dioxane-2,10'-pyrimido[1,2-a]indole];

3',3'-Dimethyl-8'-vinyl-3',4'-dihydro-2'H-spiro[1,3-dioxane-2,10'-pyrimido[1,2-a]indole];

Methyl 3',3'-dimethyl-3',4'-dihydro-2'H-spiro[1,3-dioxane-2,10'-pyrimido[1,2a]indol]-8'-carboxylate;

3',3'-Dimethyl-3',4'-dihydro-2'H-spiro[1,3-dioxane-2,10'-pyrimido[1,2-a]indole]-8'-carboxylic acid;

2'-Methyl-8'-(pyrrolidin-1-ylsulfonyl)-3',4'-dihydro-2'H-spiro[1,3-dioxane-2,10'-pyrimido[1,2-a]indole];

8'-{[(2S)-2-(methoxymethyl)pyrrolidin-1-yl]sulfonyl}spiro[cycloheptane-1,3'-pyrimido[1,2-a]indol]-10'(2'H)-one;

or pharmaceutically acceptable salts thereof.

* * * * *

UNITED STATES PATENT AND TRADEMARK OFFICE
CERTIFICATE OF CORRECTION

| | | |
|---|---|---|
| PATENT NO. | : 7,256,198 B2 | Page 1 of 1 |
| APPLICATION NO. | : 11/06144 | |
| DATED | : August 14, 2007 | |
| INVENTOR(S) | : Paul Jeffrey Dollings et al. | |

It is certified that error appears in the above-identified patent and that said Letters Patent is hereby corrected as shown below:

Col. 123-234 Claim 28 Line 43
Delete claim 28 entirely

Col. 124 Claim 29 Line 33
Delete claim 29 entirely

Signed and Sealed this
Twenty-fifth Day of January, 2011

David J. Kappos
*Director of the United States Patent and Trademark Office*